(12) United States Patent
Gaston et al.

(10) Patent No.: US 9,701,714 B2
(45) Date of Patent: Jul. 11, 2017

(54) COMPOSITIONS AND METHODS FOR REGULATING ARTERIAL TONE

(71) Applicant: University of Virginia Patent Foundation, Charlottesville, VA (US)

(72) Inventors: Benjamin M. Gaston, Gates Mills, OH (US); Adam C. Straub, Pittsburgh, PA (US); Brant E. Isakson, Charlottesville, VA (US); Linda Columbus, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 35 days.

(21) Appl. No.: 14/437,548

(22) PCT Filed: Oct. 22, 2013

(86) PCT No.: PCT/US2013/066186
§ 371 (c)(1),
(2) Date: Apr. 22, 2015

(87) PCT Pub. No.: WO2014/066392
PCT Pub. Date: May 1, 2014

(65) Prior Publication Data
US 2015/0274779 A1  Oct. 1, 2015

Related U.S. Application Data

(60) Provisional application No. 61/716,846, filed on Oct. 22, 2012.

(51) Int. Cl.
| | |
|---|---|
| *A61K 38/00* | (2006.01) |
| *C07K 7/08* | (2006.01) |
| *C07K 14/805* | (2006.01) |
| *C07K 7/06* | (2006.01) |
| *C07K 16/00* | (2006.01) |
| *C07K 16/18* | (2006.01) |
| *C12N 15/113* | (2010.01) |

(52) U.S. Cl.
CPC ............ *C07K 7/08* (2013.01); *C07K 7/06* (2013.01); *C07K 14/805* (2013.01); *C07K 16/00* (2013.01); *C07K 16/18* (2013.01); *C12N 15/113* (2013.01); *A61K 38/00* (2013.01); *C07K 2317/76* (2013.01); *C07K 2319/10* (2013.01); *C12N 15/1137* (2013.01); *C12N 2310/14* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 6,645,501 B2 * | 11/2003 | Dowdy | C07K 14/005 424/192.1 |
| 8,586,006 B2 * | 11/2013 | Hood | G01N 33/6845 424/1.11 |
| 2002/0037839 A1 | 3/2002 | Stamler | |

FOREIGN PATENT DOCUMENTS

| | | |
|---|---|---|
| WO | WO-9921015 | 4/1999 |
| WO | 2014/160465 | * 10/2014 |

OTHER PUBLICATIONS

Machado et al Peptide Science vol. 88 p. 413 (2007).*
Hu et al, Accession No. ARR21709 (2007).*
Fogaca, Andrea C, "Antimicrobial Activity of a Bovine Hemoglobin Fragment in the Tick Boophilus miroplus", The Journal of Biological Chemistry, vol. 274, No. 36, (Sep. 1, 1999), 25330-25334.
Hobbs, Adrian J, "Haemoglobin: NO transporter, NO inactivator or NOne of the above?", Trends in Pharmological Sciences, vol. 23, No. 9, (Sep. 1, 2002), 406-411.
Machado, Alessandra, "Truncation of Amidated Fragment 33-61 of Bovine α—Hemoglobin: Effects on the Structure and Anticandidal Activity", Peptide Science, vol. 88, No. 3, (2007), 413-426.
Straub, Adam, "Cytochrome B 5 reductase 3 regulates nitric oxide signaling at the myoendothelial by controlling hemoglobin redox cycling", The FASEB Journal, 26, 853.25. <http://www.fasebj.org/cgi/content/meeting_abstract/26/1_MeetingAb, (2012), 1 pg.
Straub, Adam, "Endothelial cell expression of hemoglobin a regulates nitric oxide signaling", Abstracts/Nitric Oxide, 27. [Online]. <http://dx.doi.org/10.1016/j.niox.2012.04.048>, (Jan. 1, 2012), 513.
Straub, Adam, "Hemoglobin expression at the myoendothelial junction regulates nitric oxide scavenging and vasomotor tone", The FASEB Journal, 1057.28, 26. [Online]. <http://www.fasebj.org/cgi/content/metting_abstract/26/1_MeetingAB, (Jan. 1, 2012), 1 pg.

* cited by examiner

*Primary Examiner* — Sheela J Huff
(74) *Attorney, Agent, or Firm* — Rodney L. Sparks

(57) ABSTRACT

The present invention provides compositions and methods for regulating arterial tone based on the discovery herein of novel expression and regulation of hemoglobin alpha and cytochrome B5 reductase 3 and the effects on NO and NOS.

4 Claims, 57 Drawing Sheets

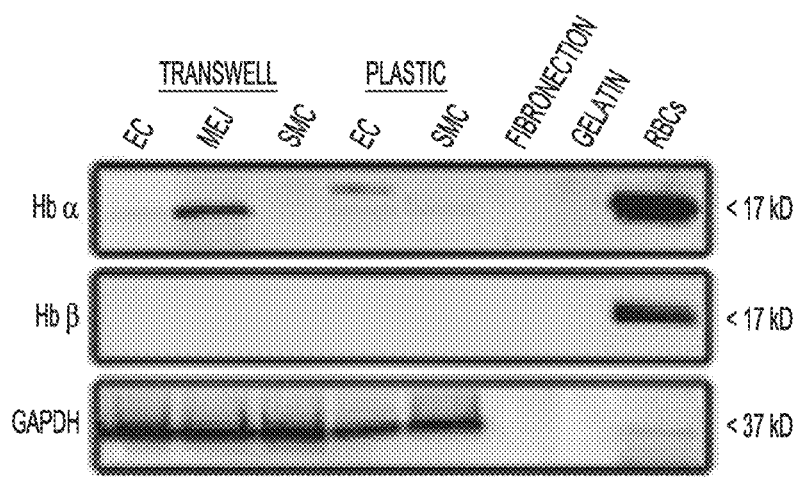
FIG. 1A1
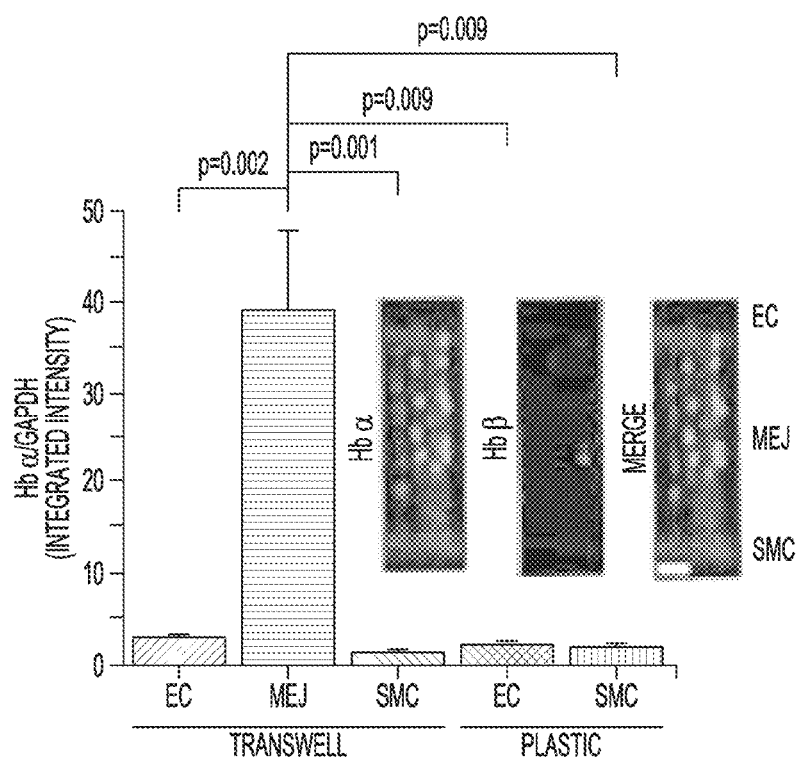
FIG. 1A2

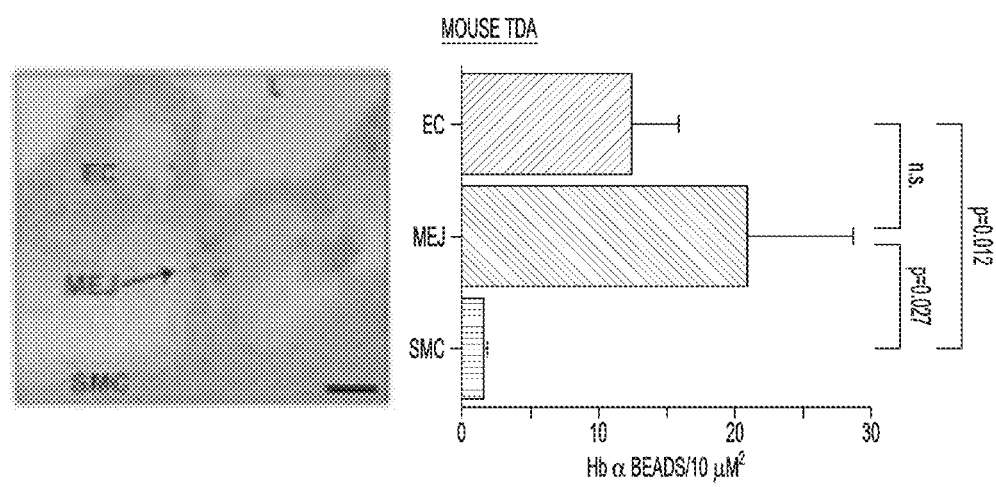
FIG. 1B1
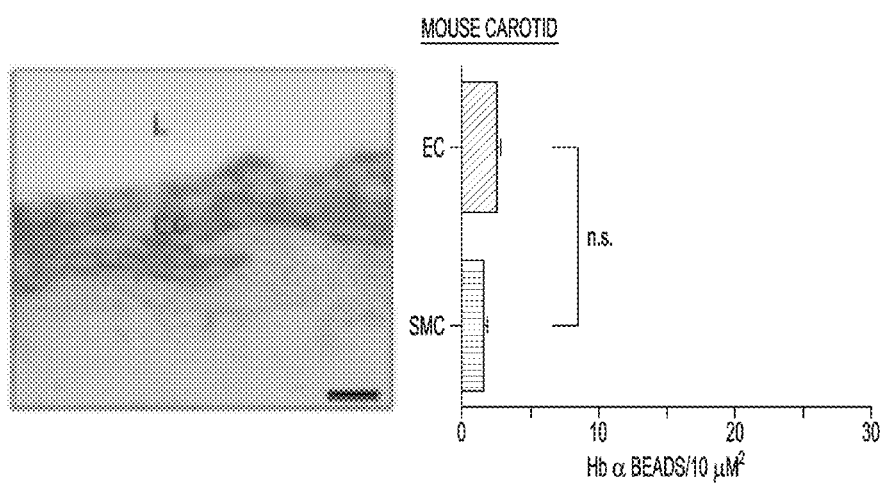
FIG. 1B2

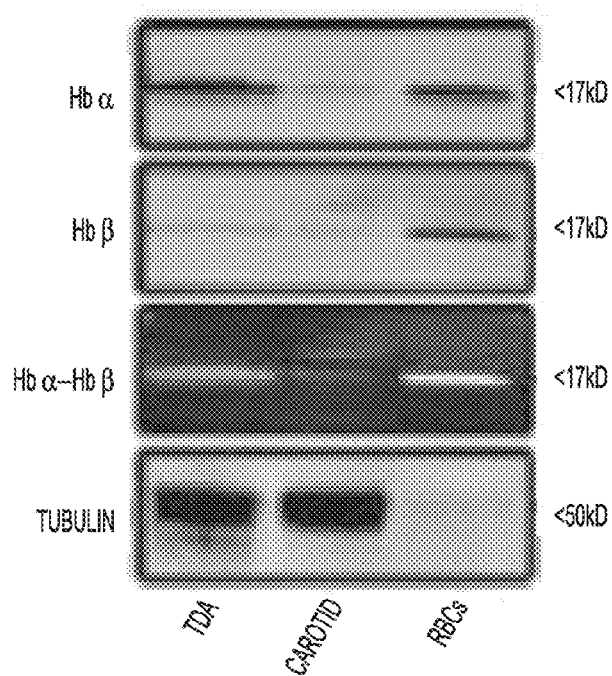
*FIG. 1C1*
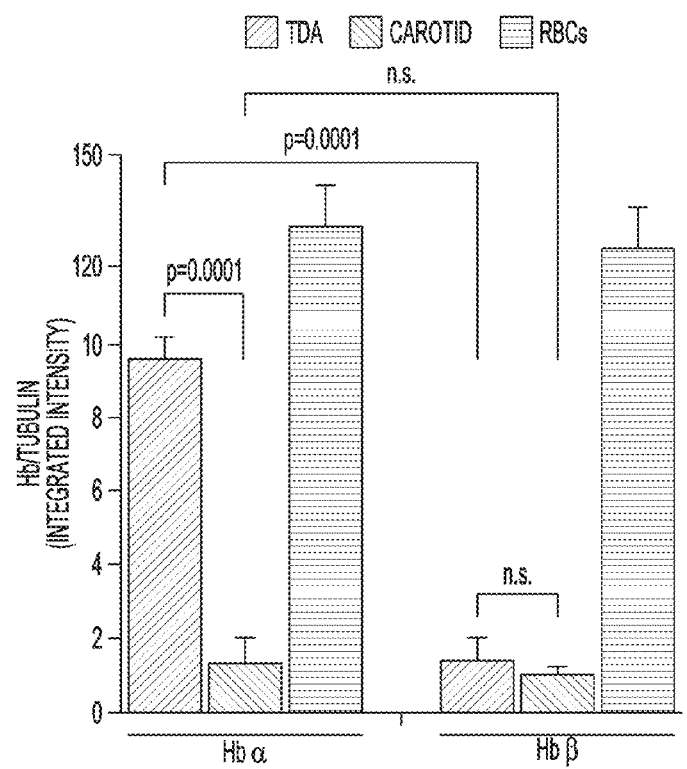
*FIG. 1C2*

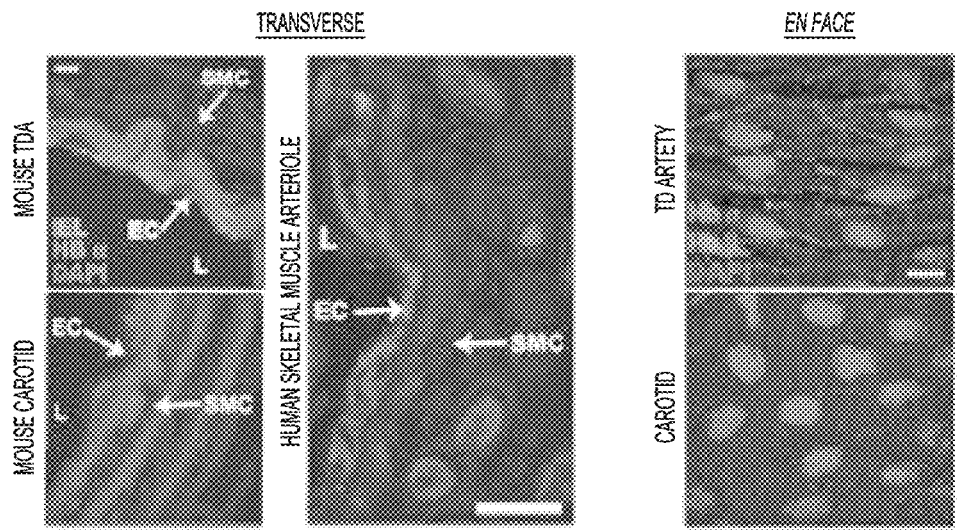
FIG. 1D  FIG. 1E
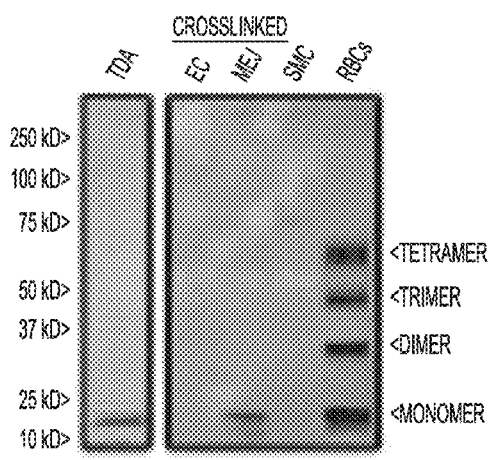
FIG. 1F1
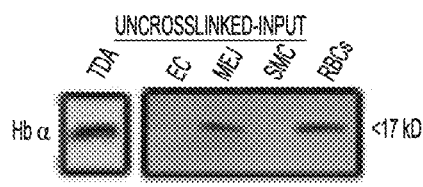
FIG. 1F2
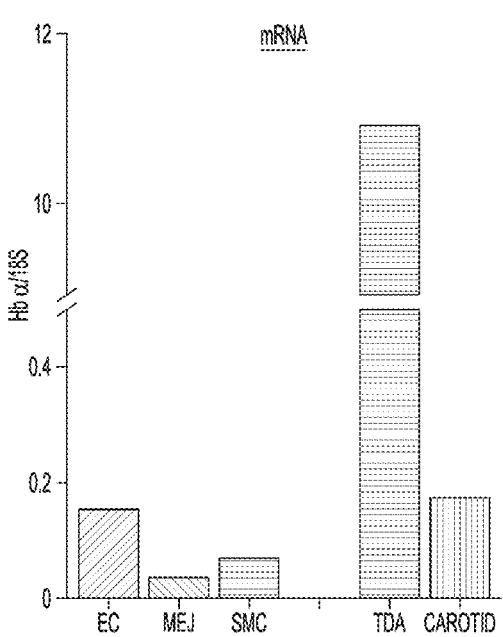
FIG. 1G

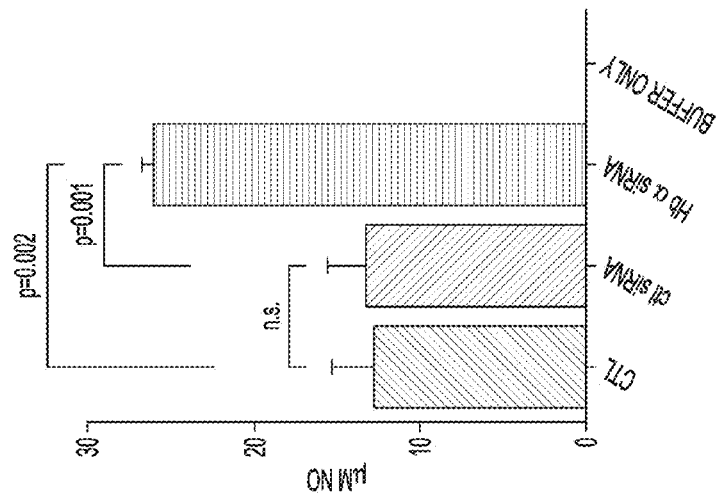
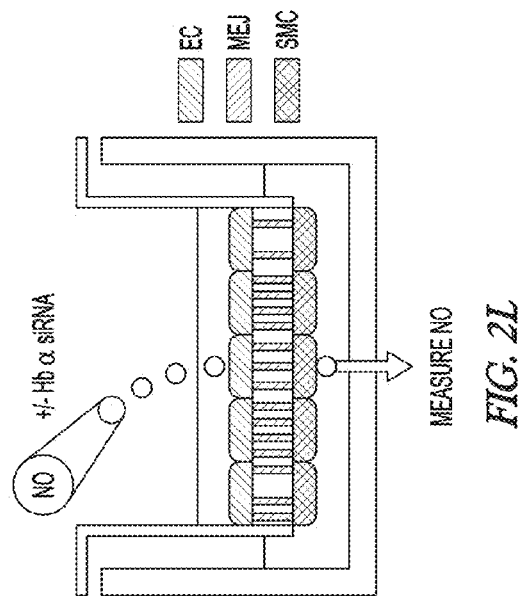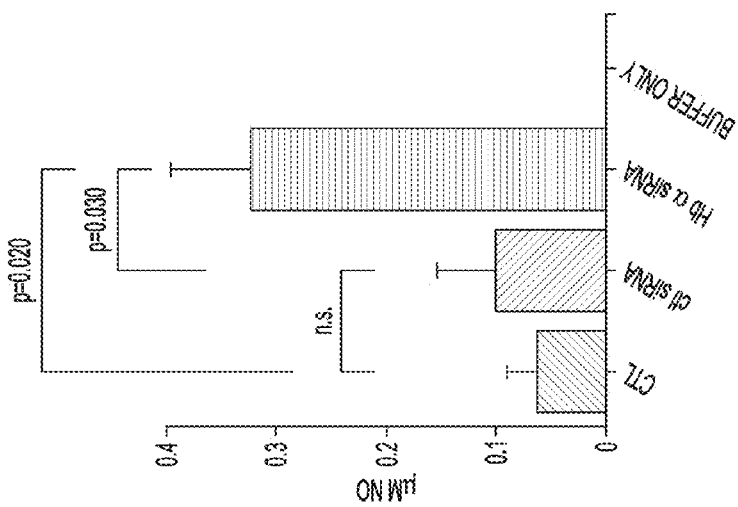

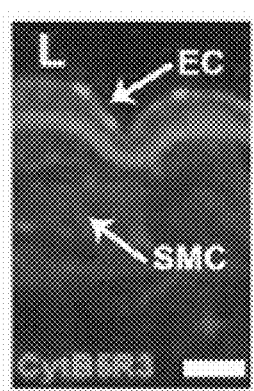 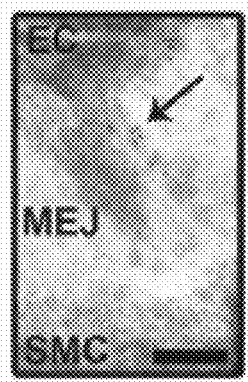 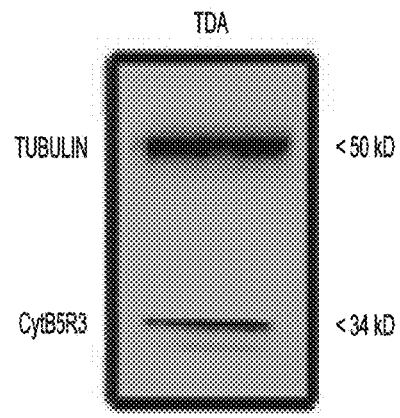
FIG. 4A  FIG. 4B  FIG. 4C
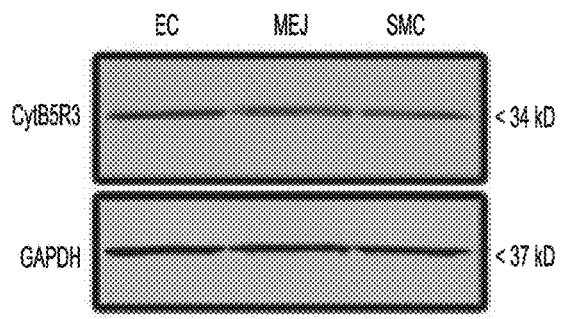 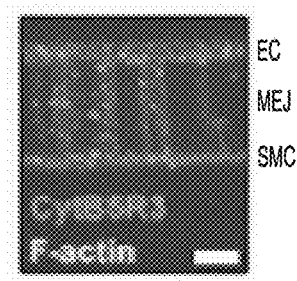
FIG. 4D  FIG. 4E
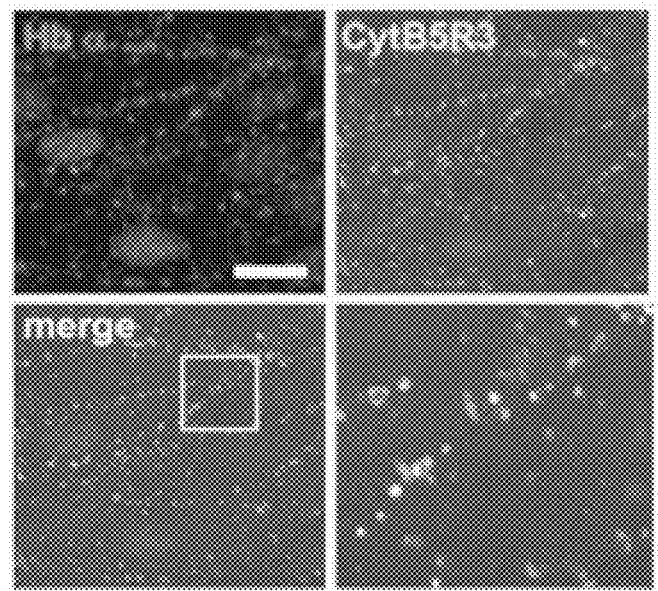
FIG. 4F

| Protein ID | Protein Name | Ratio: MEJ/EC | Ratio: MEJ/SMC |
|---|---|---|---|
| IPI00930226 | Gene_Symbol=ACTG1 cDNA FLJ57283, highly similar to Actin, cytoplasmic 2 | 0.3021 | 0.8553 |
| IPI00921118 | Gene_Symbol=ACTN1 Actinin alpha 1 isoform 3 | 1.1202 | 1.53215 |
| IPI00013808 | Gene_Symbol=ACTN4 Alpha-actinin-4 | 0.1604 | 0.3742 |
| IPI00953689 | Gene_Symbol=AHSG Alpha-2-HS-glycoprotein | 0.4277 | 0.38295 |
| IPI00796333 | Gene_Symbol=ALDOA 45 kDa protein | 0.61695 | 0.26935 |
| IPI00218918 | Gene_Symbol=ANXA1 Annexin A1 | 0.781 | 0.58165 |
| IPI00418169 | Gene_Symbol=ANXA2 Isoform 2 of Annexin A2 | 0.2099 | 0.35815 |
| IPI00872379 | Gene_Symbol=ANXA5 36 kDa protein | 1.51225 | 0.68485 |
| IPI00221226 | Gene_Symbol=ANXA6 Annexin A6 | 0.85925 | 0.51775 |
| IPI00790819 | Gene_Symbol=AQP2 14 kDa protein | 1.57145 | 1.72305 |
| IPI00004065 | Gene_Symbol=ART4 Ecto-ADP-ribosyltransferase 4 | 1.3193 | 1.8044 |
| IPI00014516 | Gene_Symbol=CALD1 Isoform 1 of Caldesmon | 1.19785 | 0.7489 |
| IPI00020599 | Gene_Symbol=CALR Calreticulin | 16.12175 | 2.011 |
| IPI00789155 | Gene_Symbol=CALU cDNA FLJ31776 fis, clone NT2RI2008141, highly similar to CALUMENIN | 1.0455 | 0.37955 |
| IPI00290462 | Gene_Symbol=CBR3 Carbonyl reductase [NADPH] 3 | 1.1872 | 0.77715 |
| IPI00956122 | Gene_Symbol=CD44 CD44 antigen isoform 1 precursor | 0.95525 | 2.39955 |
| IPI00012011 | Gene_Symbol=CFL1 Cofilin-1 | 0.3911 | 0.347 |
| IPI00141318 | Gene_Symbol=CKAP4 Isoform 1 of Cytoskeleton-associated protein 4 | 7.1652 | 13.77925 |
| IPI00010896 | Gene_Symbol=CLIC1 Chloride intracellular channel protein 1 | 1.3144 | 1.0537 |
| IPI00001960 | Gene_Symbol=CLIC4 Chloride intracellular channel protein 4 | 0.3467 | 0.38725 |
| IPI00022200 | Gene_Symbol=COL6A3 Isoform 1 of Collagen alpha-3(VI) chain | 1.3139 | 3.2104 |
| IPI00921090 | Gene_Symbol= Conserved hypothetical protein | 3.37085 | 2.33205 |
| IPI00017704 | Gene_Symbol=COTL1 Coactosin-like protein | 1.36565 | 0.3625 |
| IPI00021369 | Gene_Symbol=CRYAB Alpha-crystallin B chain | 13.90295 | 0.6069 |
| IPI00873991 | Gene_Symbol=DNAH8 537 kDa protein | 1.2594 | 1.44595 |
| IPI00257508 | Gene_Symbol=DPYSL2 Dihydropyrimidinase-related protein 2 | 0.27665 | 0.10515 |
| IPI00472724 | Gene_Symbol=EEF1A1;EEF1A1P5 Putative elongation factor 1-alpha-like 3 | 0.18885 | 0.4208 |
| IPI00465248 | Gene_Symbol=ENO1 Isoform alpha-enolase of Alpha-enolase | 0.6549 | 0.6858 |
| IPI00644576 | Gene_Symbol=FLNA Filamin A, alpha | 1.0704 | 1.3108 |
| IPI00413958 | Gene_Symbol=FLNC Isoform 2 of Filamin-C | 1.09735 | 1.1385 |
| IPI00747810 | Gene_Symbol=FSCN1 FSCN1 protein (Fragment) | 0.64905 | 2.53675 |

*FIG. 7A*

| | | | |
|---|---|---|---|
| IPI00219018 | Gene_Symbol=GAPDH Glyceraldehyde-3-phosphate dehydrogenase | 1.04795 | 0.50625 |
| IPI00026268 | Gene_Symbol=GNB1 Guanine nucleotide-binding protein G(I)/G(S)/G(T) subunit beta-1 | 0.23695 | 1.083 |
| IPI00022793 | Gene_Symbol=HADHB Trifunctional enzyme subunit beta, mitochondrial | 1.26155 | 0.73265 |
| IPI00410714 | Gene_Symbol=HADHB | | |
| IPI00657660 | Gene_Symbol=HBD Delta-globin B2 variant | 0.78065 | 0.81745 |
| IPI00166293 | Gene_Symbol=HIST3H2BB Histone H2B type 3-B | 0.13985 | 0.5219 |
| IPI00479191 | Gene_Symbol=HNRPH1 51 kDa protein | 0.05105 | 0.34365 |
| IPI00883857 | Gene_Symbol=HNRNPU Isoform Long of Heterogeneous nuclear ribonucleoprotein U | 1.95535 | 1.2112 |
| IPI00414676 | Gene_Symbol=HSP90AB1 Heat Shock protein HSP 90-beta | 0.2111 | 0.92995 |
| IPI00027230 | Gene_Symbol=HSP90B1 Endoplasmin | 0.6446 | 0.24505 |
| IPI00003362 | Gene_Symbol=HSPA5 HSPA5 protein | 4.06725 | 0.7068 |
| IPI00003865 | Gene_Symbol=HSPA8 Isoform 1 of Heat shock cognate 71 kDa protein | 0.4442 | 0.5696 |
| IPI00924436 | Gene_Symbol=HSPB1 20 kDa protein | 0.6741 | 0.3637 |
| IPI00032328 | Gene_Symbol=KNG1 Isoform HMW of Kininogen-1 | 0.9579 | 0.79675 |
| IPI00384444 | Gene_Symbol=KRT14 Keratin, type I cytoskeletal 14 | 5.7546 | 4.0181 |
| IPI00021304 | Gene_Symbol=KRT2 Keratin, type II cytoskeletal 2 epidermal | 1.24675 | 10.7588 |
| IPI00019359 | Gene_Symbol=KRT9 Keratin, type I cytoskeletal 9 | 8.56845 | 179.0202 |
| IPI00939286 | Gene_Symbol=LDHA L-lactate dehydrogenase | 0.21055 | 0.1404 |
| IPI00219219 | Gene_Symbol=LGALS1 Galectin-1 | 2.52295 | 0.5175 |
| IPI00644087 | Gene_Symbol=LMNA Progerin | 0.7282 | 0.5324 |
| IPI00935323 | Gene_Symbol=LOC100289504;LOC100293312 hypothetical protein XP_002343634 | 0.84845 | 0.78815 |
| IPI00888355 | Gene_Symbol=LOC389217 similar to SET translocation | 0.94265 | 2.1596 |
| IPI00411375 | Gene_Symbol=MAP4 microtubule-associated protein 4 isoform 2 | 0.7313 | 0.41315 |
| IPI00293276 | Gene_Symbol=MIF Macrophage migration inhibitory factor | 1.977 | 0.8166 |
| IPI00219365 | Gene_Symbol=MSN Moesin | 0.50445 | 0.81435 |
| IPI00019502 | Gene_Symbol=MYH9 Isoform 1 of Myosin-9 | 0.3237 | 3.17825 |
| IPI00335168 | Gene_Symbol=MYL6;MYL6B Isoform Non-muscle of Myosin light polypeptide 6 | 0.9728 | 1.23605 |
| IPI00604620 | Gene_Symbol=NCL Nucleolin | 1.0192 | 1.09715 |
| IPI00917728 | Gene_Symbol=NEB nebulin isoform 2 | 0.8756 | 1.9875 |
| IPI00853115 | Gene_Symbol=NEFM NEFM protein | 0.86665 | 0.10045 |
| IPI00304596 | Gene_Symbol=NONO Non-POU domain- | 0.2604 | 0.53905 |

*FIG. 7B*

|  | containing octamer-binding protein | | |
|---|---|---|---|
| IPI00549248 | Gene_Symbol=NPM1 Isoform 1 of Nucleophosmin | 1.0555 | 1.366 |
| IPI00010796 | Gene_Symbol=P4HB Protein disulfide-isomerase | 4.72045 | 0.66985 |
| IPI00298547 | Gene_Symbol=PARK7 Protein DJ-1 | 0.92995 | 0.35685 |
| IPI00025252 | Gene_Symbol=PDIA3 Protein disulfide-isomerase A3 | 4.09885 | 1.3825 |
| IPI00009904 | Gene_Symbol=PDIA4 Protein disulfide-isomerase A4 | 1.60935 | 1.10315 |
| IPI00007935 | Gene_Symbol=PDLIM5 PDZ and LIM domain protein 5 | 0.5297 | 0.6138 |
| IPI00216691 | Gene_Symbol=PFN1 Profilin-1 | 1.6524 | 1.43915 |
| IPI00218570 | Gene_Symbol=PGAM2 Phosphoglycerate mutase 2 | 1.1297 | 1.1091 |
| IPI00169383 | Gene_Symbol=PGK1 Phosphoglycerate kinase 1 | 0.8817 | 0.36755 |
| IPI00479186 | Gene_Symbol=PKM2 Isoform M2 of Pyruvate kinase isozymes M1/M2 | 0.57825 | 0.3297 |
| IPI00419585 | Gene_Symbol=PPIA Peptidyl-prolyl cis-trans isomerase A | 1.85905 | 1.13055 |
| IPI00000874 | Gene_Symbol=PRDX1 Peroxiredoxin-1 | 0.9869 | 0.8836 |
| IPI00176903 | Gene_Symbol=PTRF Isoform 1 of Polymerase I and transcript release factor | 0.8623 | 0.14845 |
| IPI00749512 | Gene_Symbol=RPS10 Ribosomal protein S10 variant (Fragment) | 0.3221 | 0.3281 |
| IPI00013917 | Gene_Symbol=RPS12 40S ribosomal protein S12 | 0.7751 | 0.89815 |
| IPI00026271 | Gene_Symbol=RPS14 40S ribosomal protein S14 | 1.12725 | 0.70475 |
| IPI00794659 | Gene_Symbol=RPS20 ribosomal protein S20 isoform 1 | 0.7689 | 0.61075 |
| IPI00218606 | Gene_Symbol=RPS23 40S ribosomal protein S23 | 0.84855 | 1.0108 |
| IPI00893703 | Gene_Symbol=RPS7 Putative uncharacterized protein RPS7 | 0.14635 | 0.2116 |
| IPI00032140 | Gene_Symbol=SERPINH1 Serpin H1 | 1.9216 | 1.9573 |
| IPI00853438 | Gene_Symbol=SGK2 Isoform 3 or Serine/threonine-protein kinase Sgk2 | 0.69835 | 0.75175 |
| IPI00955848 | Gene_Symbol=-SH3 domain binding glutamic acid-rich protein like 3, isoform CRA_a (Fragment) | 1.51345 | 0.66065 |
| IPI00815770 | Gene_Symbol=SNX3 Isoform 1 of Sorting nexin-3 | 0.47735 | 0.4475 |
| IPI00871508 | Gene_Symbol=SPHKAP Isoform 2 of A-kinase anchor protein SPHKAP | 1.4859 | 3.1046 |
| IPI00216138 | Gene_Symbol=TAGLN Transgelin | 1.94845 | 0.1591 |
| IPI00022463 | Gene_Symbol=TF Serotransferrin | 0.9018 | 1.0842 |
| IPI00294578 | Gene_Symbol=TGM2 Isoform 1 of Protein-glutamine gamma-glutamyltransferase 2 | 0.2218 | 0.755 |
| IPI00942979 | Gene_Symbol=TKT Transketolase | 0.4941 | 1.57705 |
| IPI00465028 | Gene_Symbol=TPI1;TPI1P1 triosephosphate | 1.05165 | 0.4987 |

*FIG. 7C*

| | isomerase 1 isoform 2 | | |
|---|---|---|---|
| IPI00010779 | Gene_Symbol=TPM4 Isoform 1 of Tropomyosin alpha-4 chain | 2.16005 | 3.68515 |
| IPI00550900 | Gene_Symbol=TPT1 Translationally-controlled tumor protein | 0.6064 | 0.34895 |
| IPI00759542 | Gene_Symbol=TTN Isoform 8 of Titin | 0.56735 | 1.05165 |
| IPI00794663 | Gene_Symbol=TUBA4A cDNA FLJ58687, highly similar to Tubulin alpha-4 chain | 0.0773 | 0.18545 |
| IPI00179330 | Gene_Symbol=UBB;RPS27A;UBC ubiquitin and ribosomal protein S27a precursor | 0.9952 | 2.00405 |
| IPI00018352 | Gene_Symbol=UCHL1 Ubiquitin carboxyl-terminal hydrolase isozyme L1 | 1.4872 | 0.34705 |
| IPI00418471 | Gene_Symbol=VIM Vimentin | 5.00405 | 0.30995 |
| IPI00798102 | Gene_Symbol=VPS29 26 kDa protein | 0.98785 | 1.4679 |
| IPI00873622 | Gene_Symbol=WDR1 Putative uncharacterized protein WDR1 | 1.19485 | 1.0797 |
| IPI00759832 | Gene_Symbol=YWHAB Isoform Short of 14-3-3 protein beta/alpha | 1.26145 | 1.1191 |
| IPI00793344 | Gene_Symbol=YWHAE 22 kDa protein | 0.9909 | 1.1377 |
| RRRRRnull | REVERSED Gene_Symbol=CACNA1H voltage-dependent T-type calcium channel subunit alpha-1H isoform b | 1.22075 | 0.814 |
| RRRRRnull | REVERSED Gene_Symbol=CKMT1B;CKMT1A Isoform 2 of Creatine kinase U-type, mitochondrial | 1.0916 | 1.8284 |
| RRRRRnull | REVERSED Gene_Symbol=RNF17 Isoform 1 of RING finger protein 17 | 1.5255 | 2.0484 |
| RRRRRnull | REVERSED Gene_Symbol=SPEG Isoform 4 of Striated muscle preferentially expressed protein kinase | 1.21155 | 0.7931 |
| RRRRRnull | REVERSED Gene_Symbol=TTN Titin, isoform CRA_a | 0.9 | 1.8803 |
| RRRRRnull | REVERSED Gene_symbol=VPS13D vacuolar protein sorting-associated protein 13D Isoform 1 | 1.6824 | 1.72955 |

*FIG. 7D*

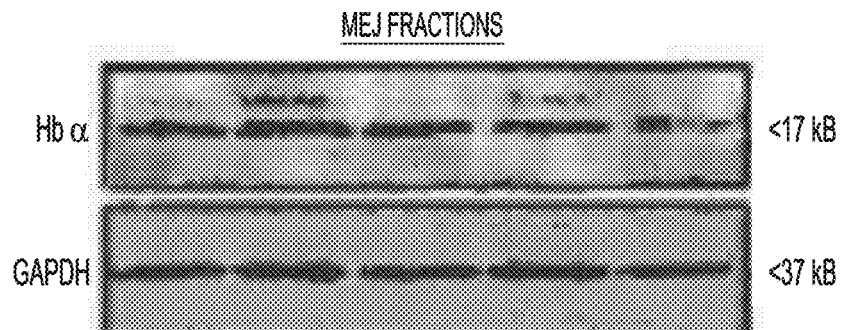
*FIG. 10A1*
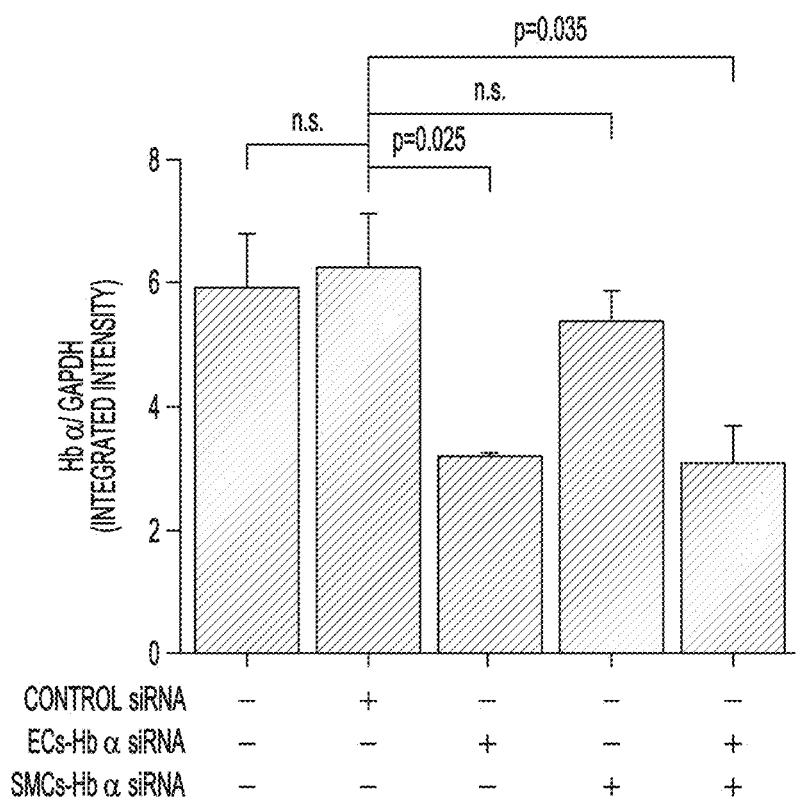
*FIG. 10A2*

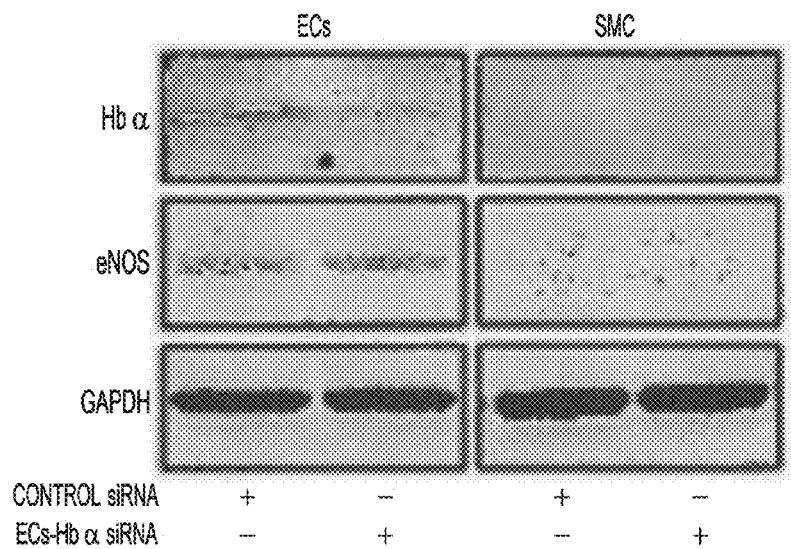
*FIG. 10B1*
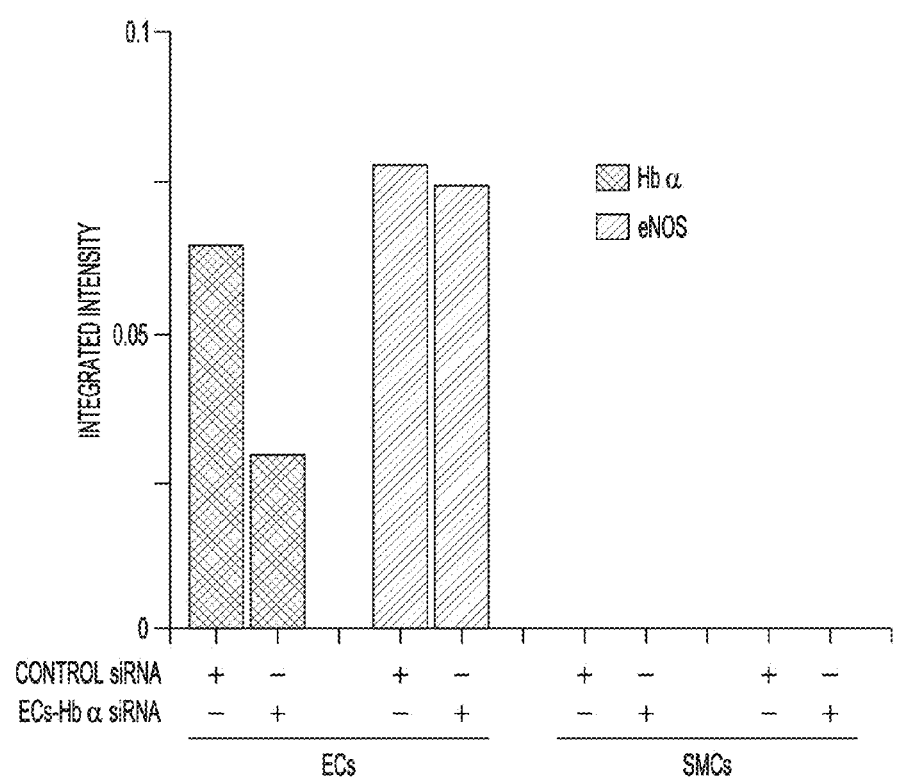
*FIG. 10B2*

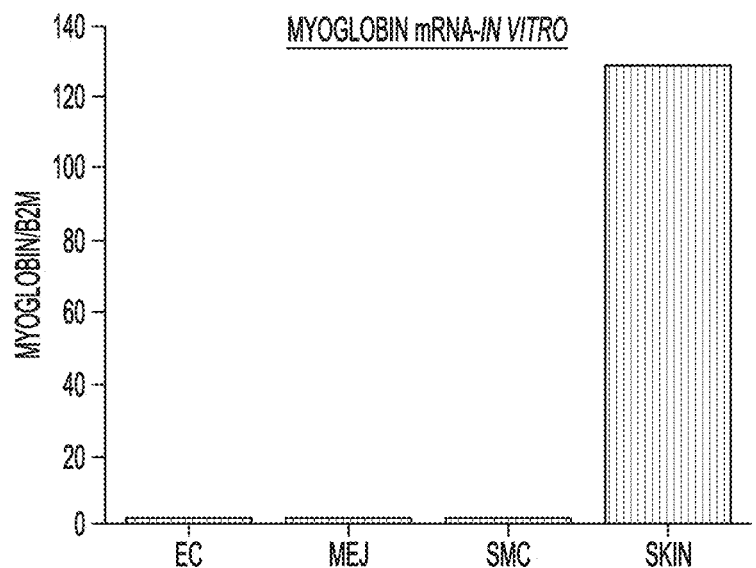
FIG. 12A1
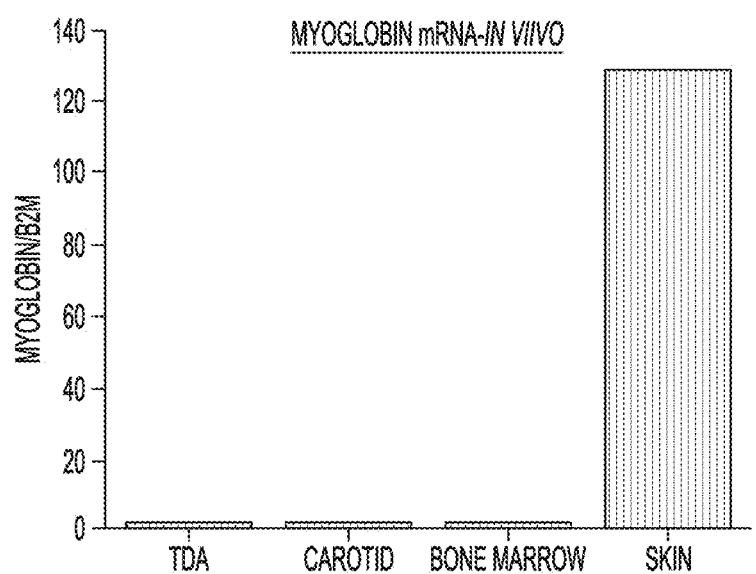
FIG. 12A2

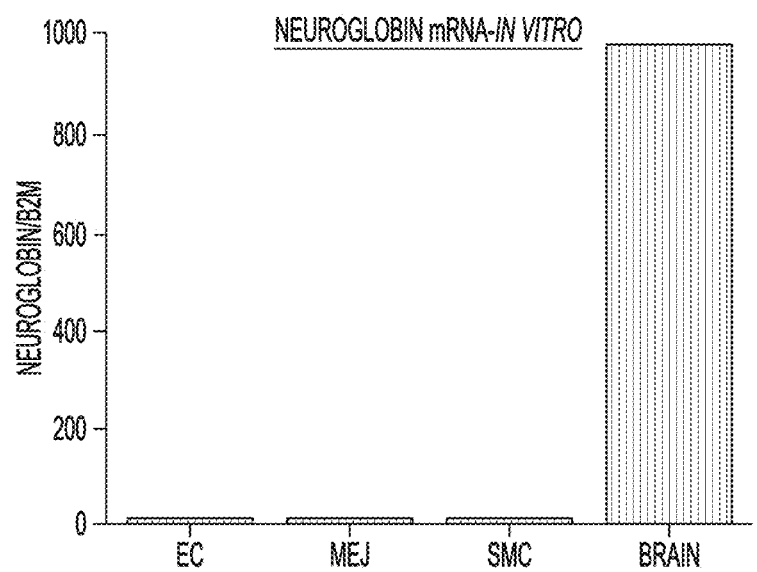
FIG. 12B1
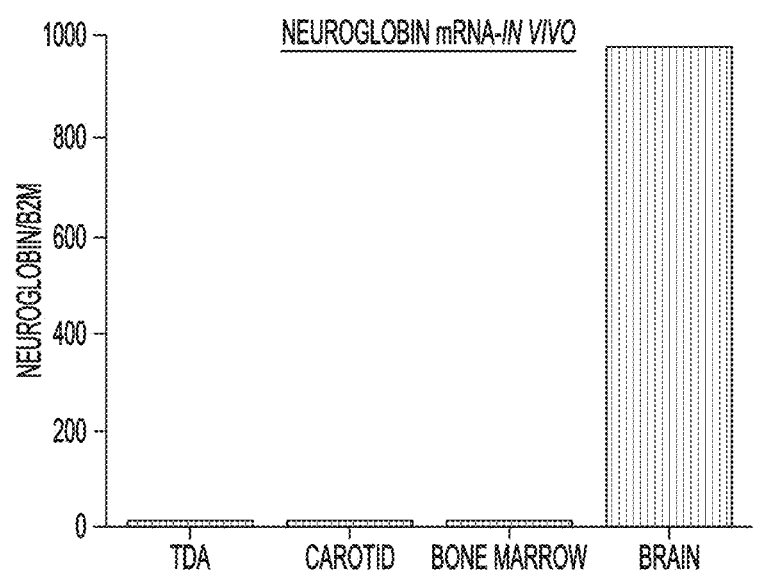
FIG. 12B2

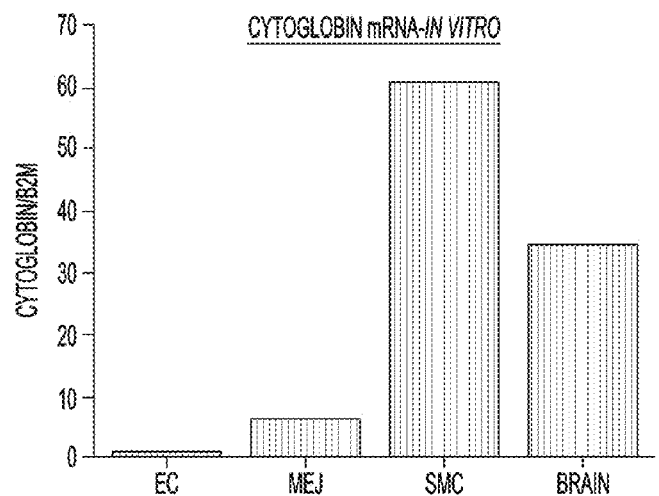
FIG. 12C1
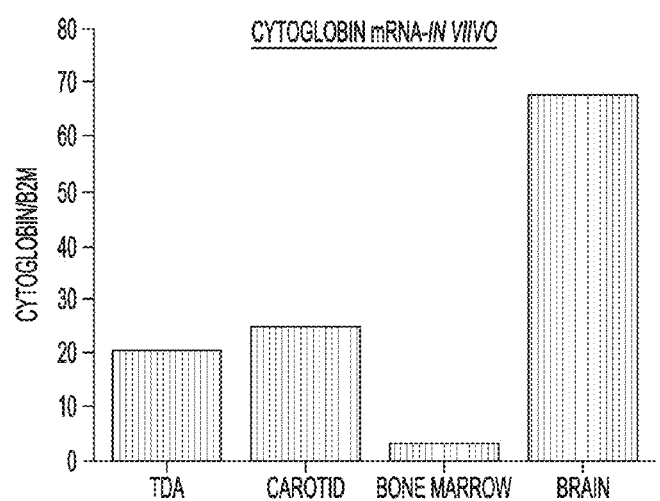
FIG. 12C2
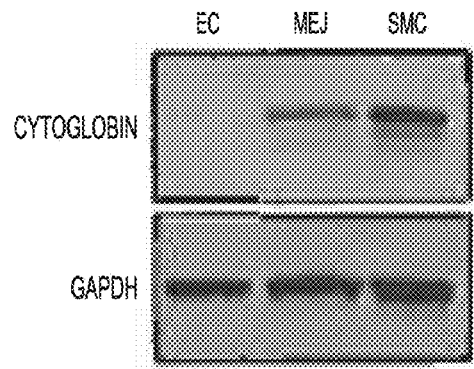
FIG. 12D

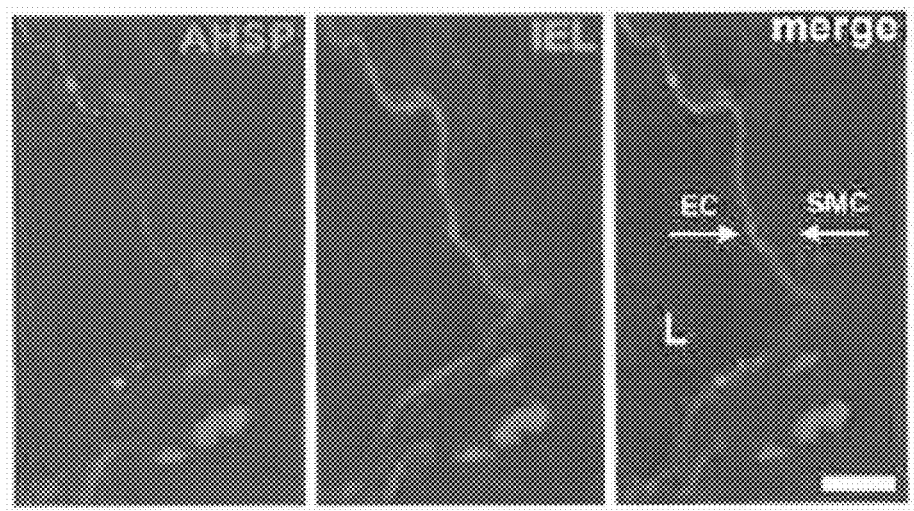
*FIG. 13A*
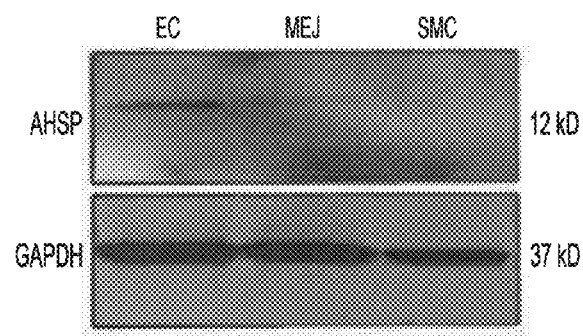
*FIG. 13B1*
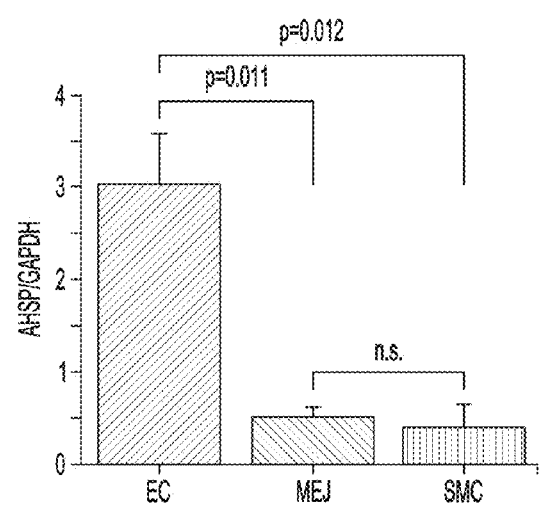
*FIG. 13B2*

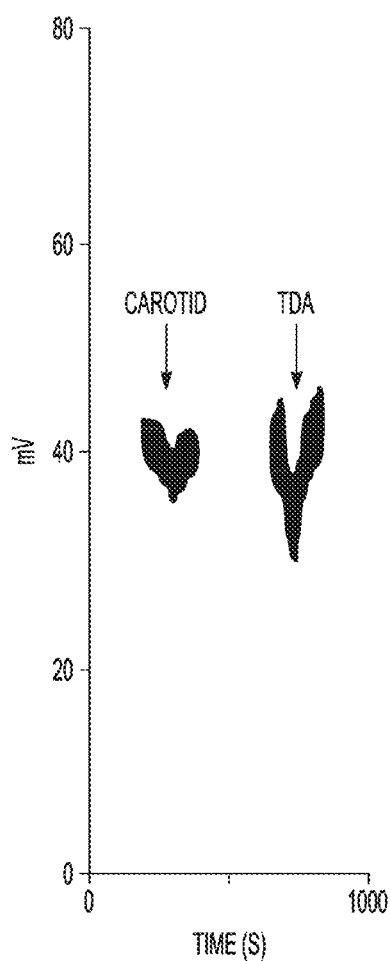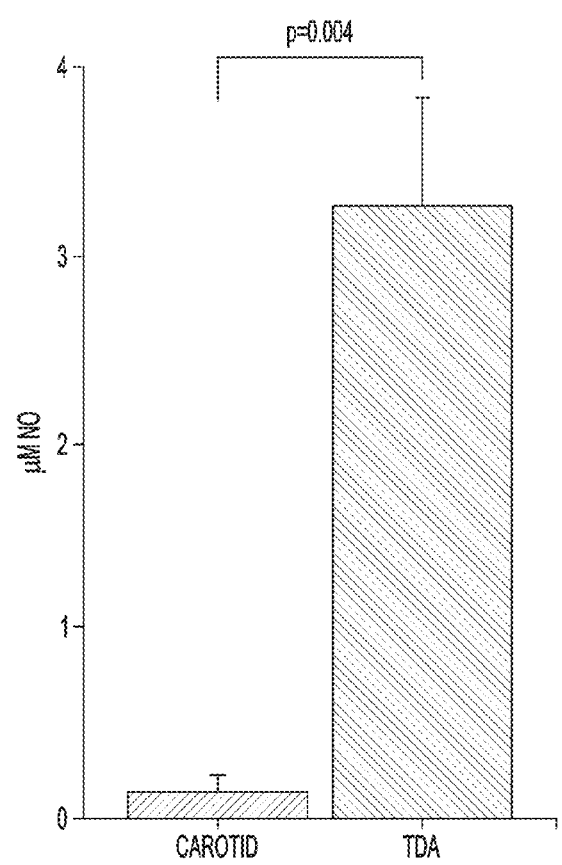
FIG. 16A1          FIG. 16A2

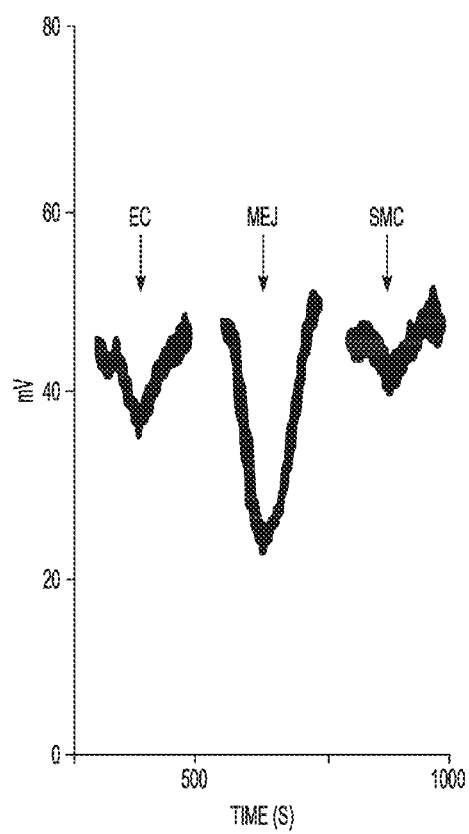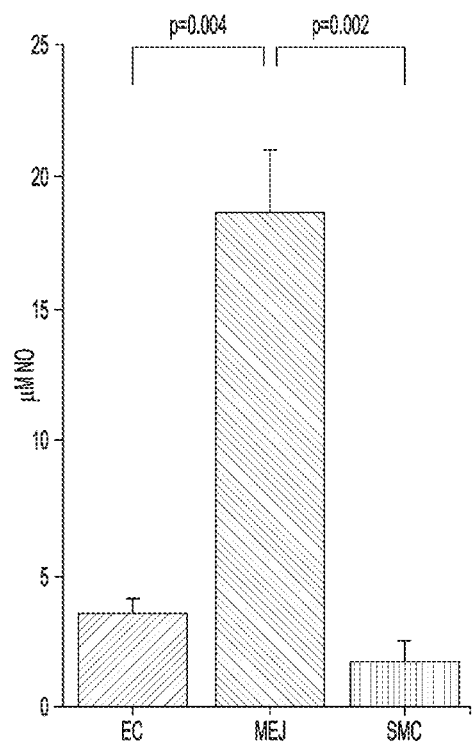
FIG. 16B1          FIG. 16B2

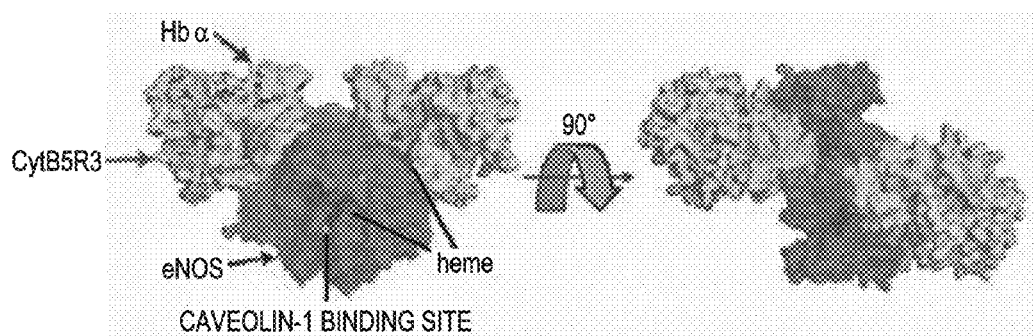
FIG. 19
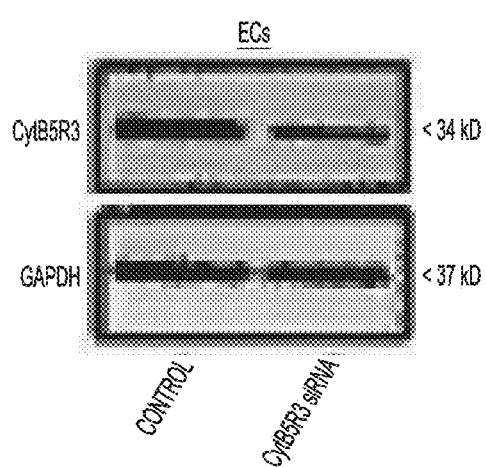
FIG. 20A1
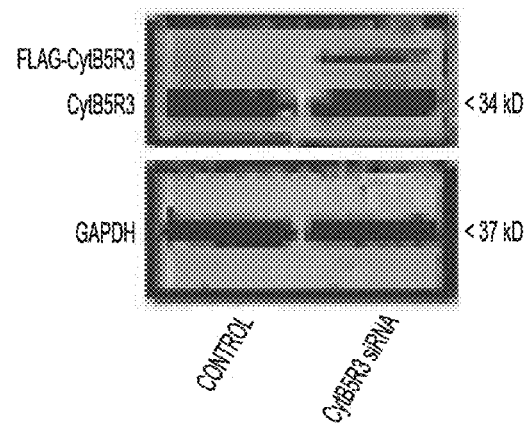
FIG. 20A2

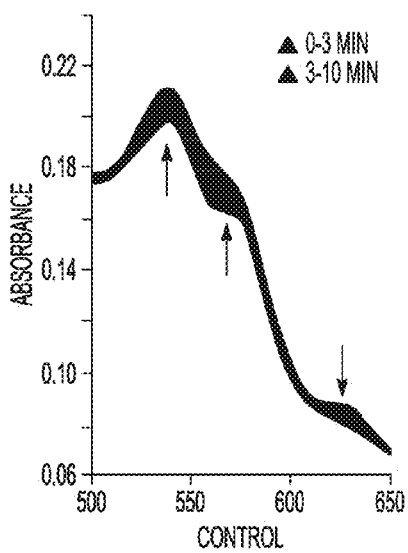
FIG. 20B1
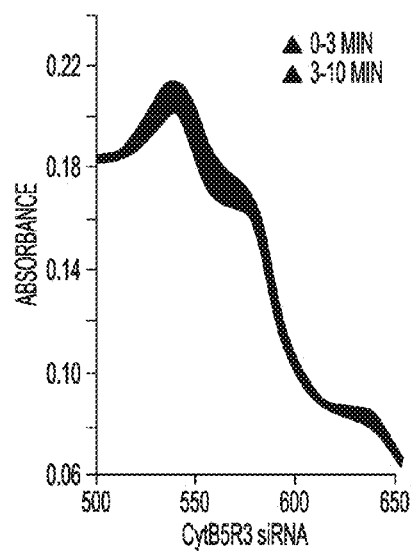
FIG. 20B2
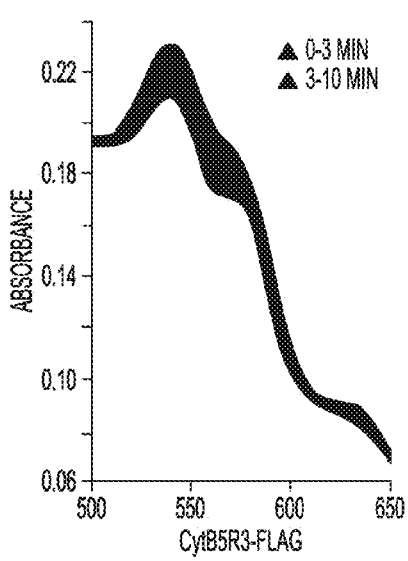
FIG. 20B3
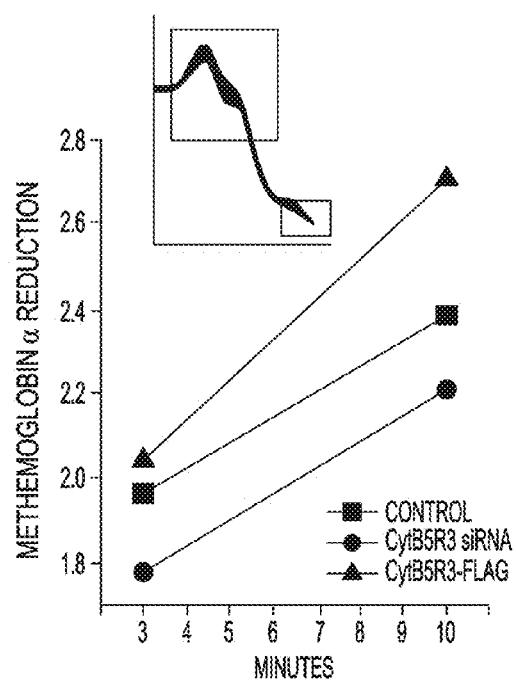
FIG. 20C

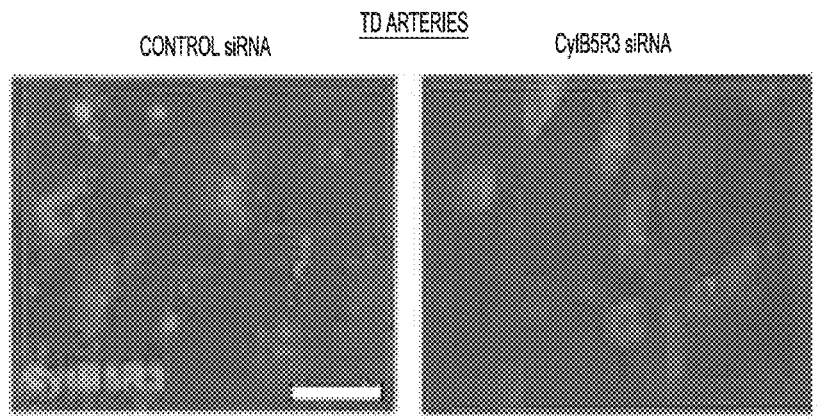
*FIG. 21A*
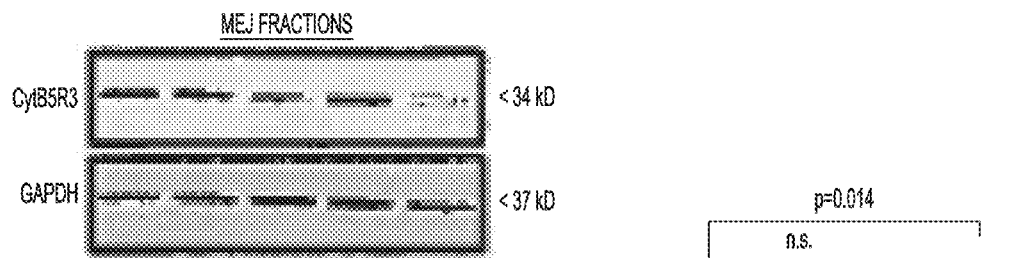
*FIG. 21B1*
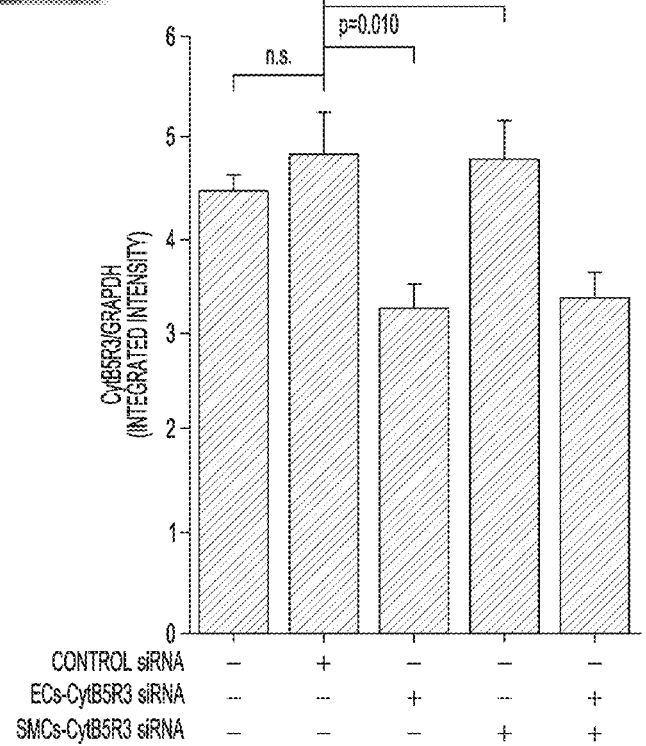
*FIG. 21B2*

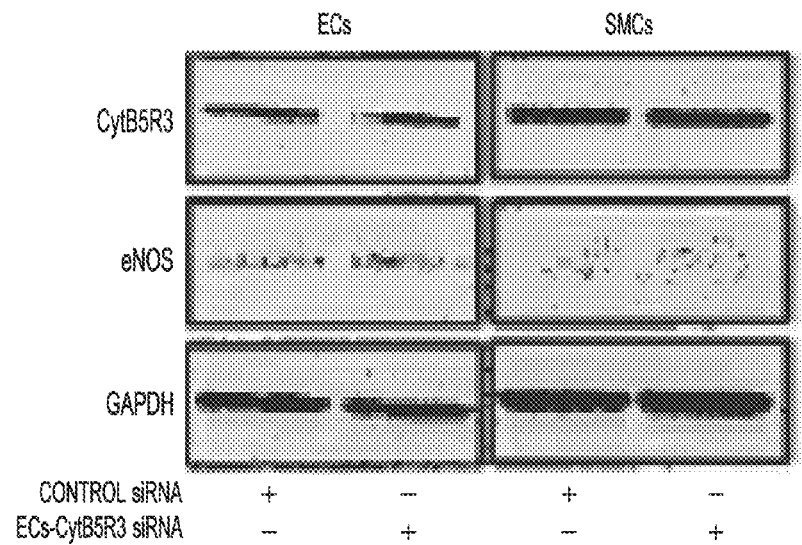
*FIG. 21C1*
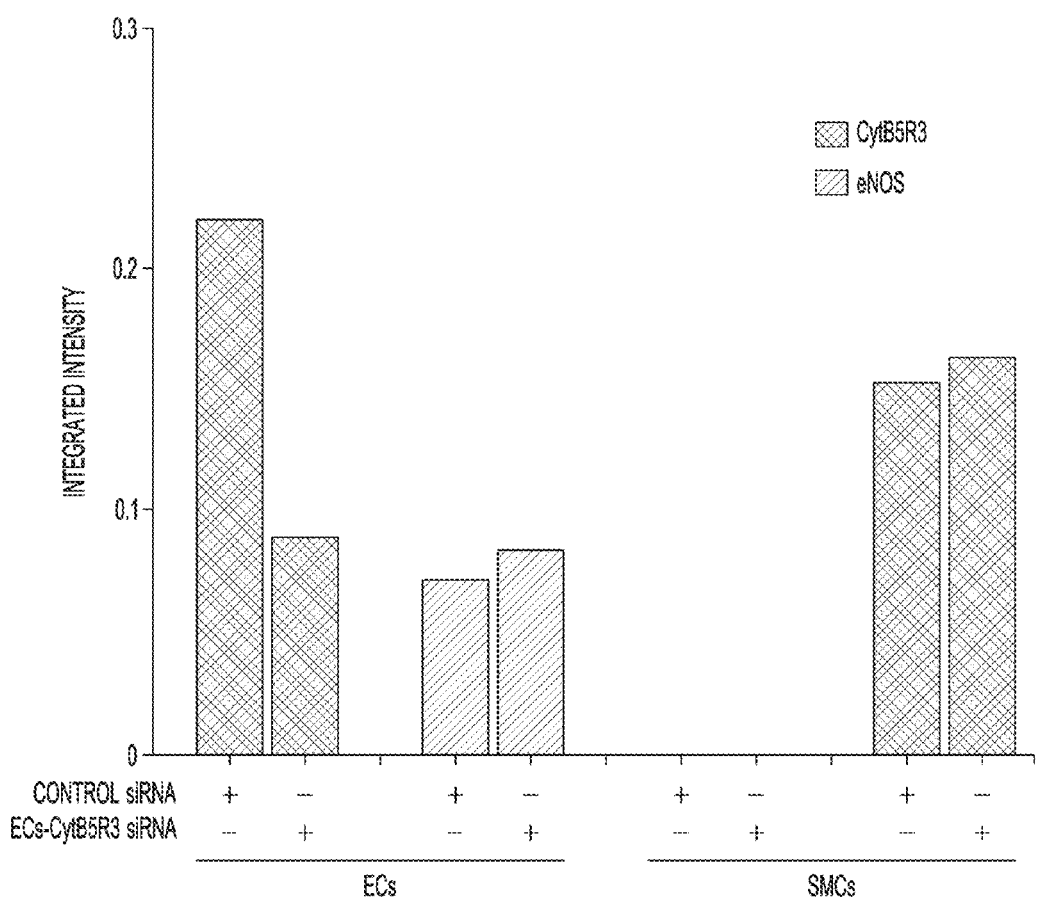
*FIG. 21C2*

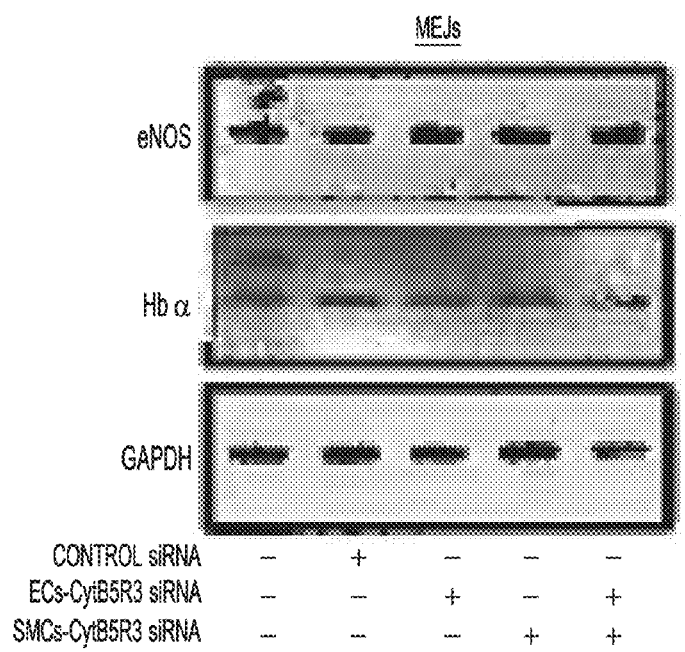
*FIG. 21D1*
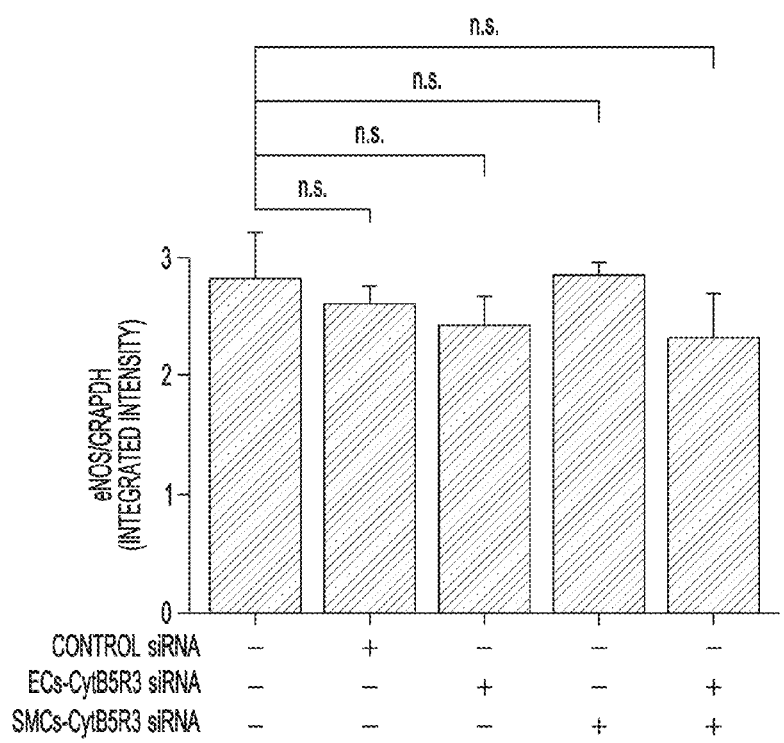
*FIG. 21D2*

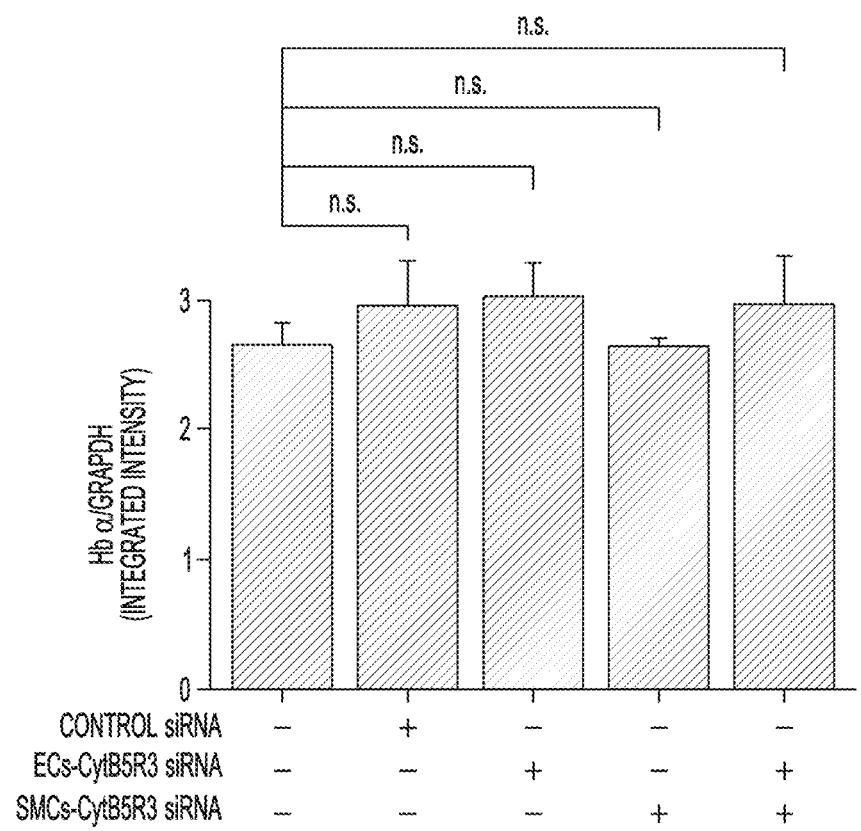
FIG. 21D3

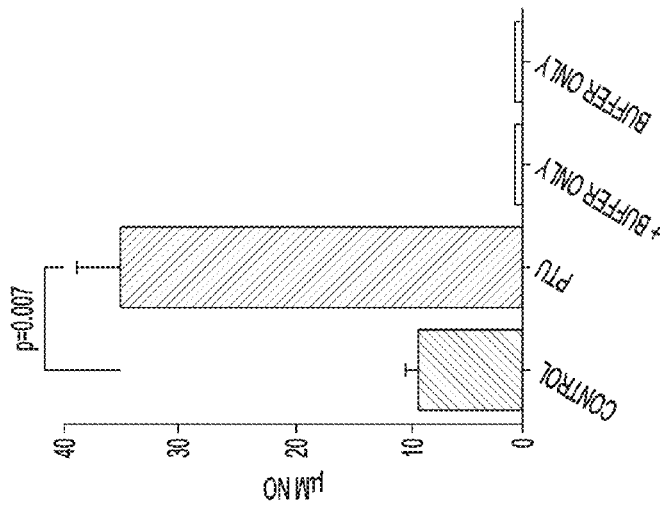
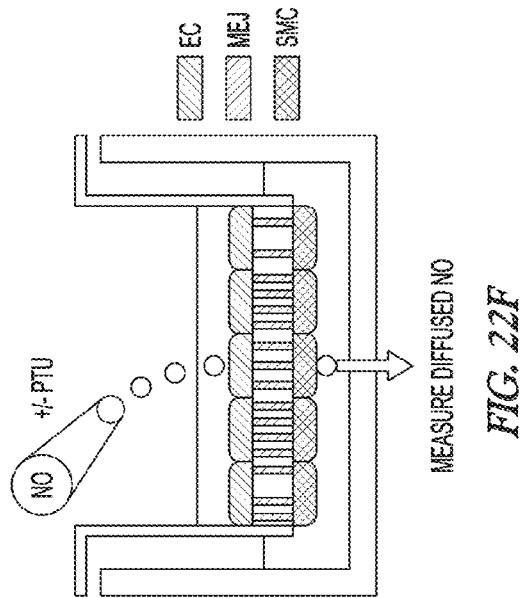
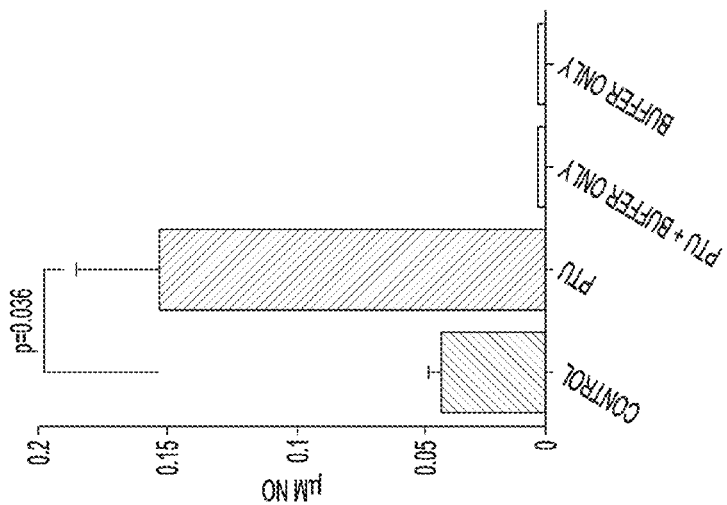
FIG. 22G
FIG. 22F
FIG. 22E

NH$_2$...LSFPTTKTYFPHFDLSHGSA...COOH

Bos taurus        LSFPTTKTYFPHFDLSHGSA (SEQ NO: 5)
Equus caballus    LGFPTTKTYFPHFDLSHGSA (SEQ NO: 6)
Homo sapiens      LSFPTTKTYFPHFDLSHGSA (SEQ NO: 7)
Mus musculus      ASFPTTKTYFPHFDVSHGSA (SEQ NO: 8)
Rattus norvegicus AAFPTTKTYFSHIDVSPGSA (SEQ NO: 9)

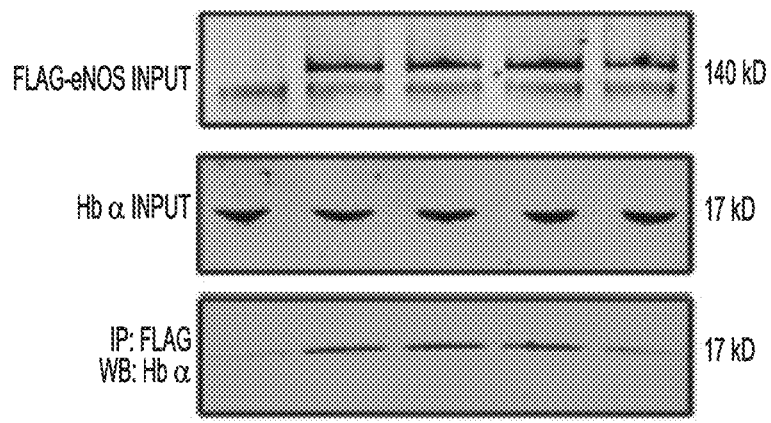
*FIG. 24B1*
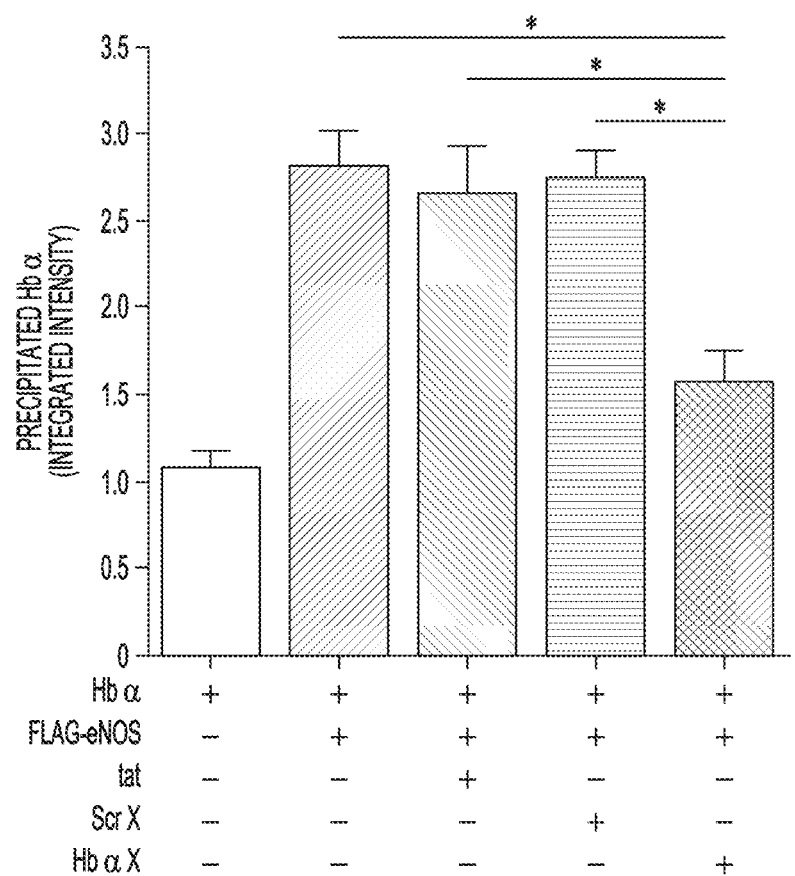
*FIG. 24B2*

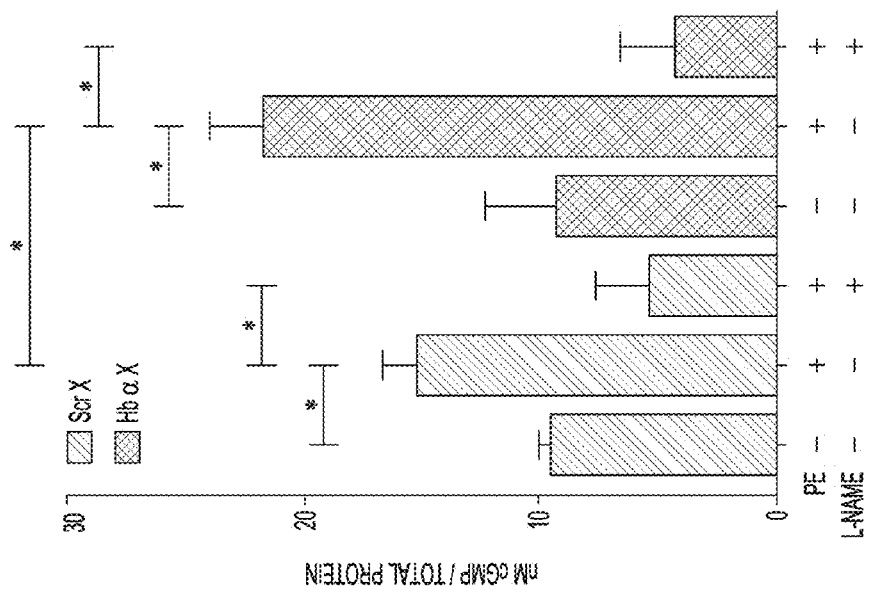
FIG. 26A
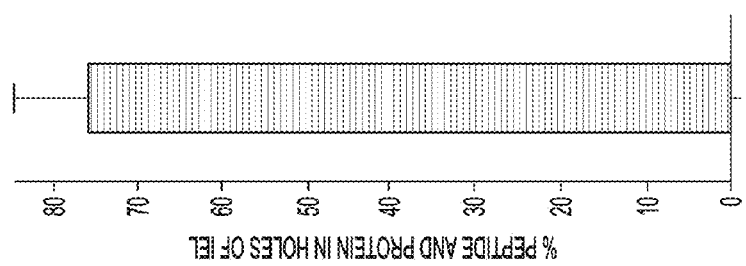
FIG. 25D2
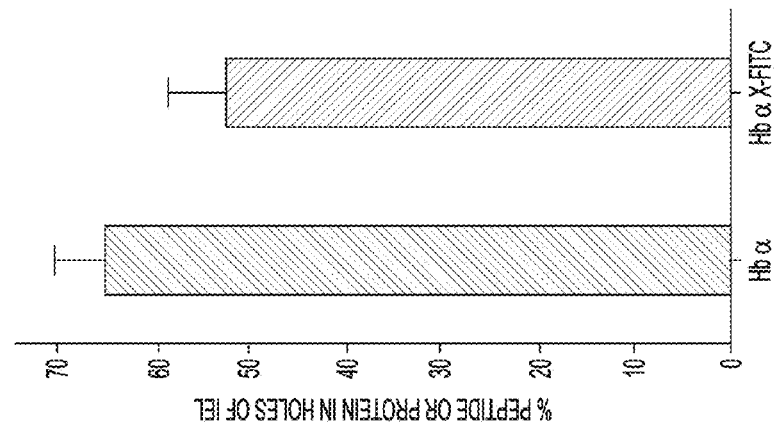
FIG. 25D1

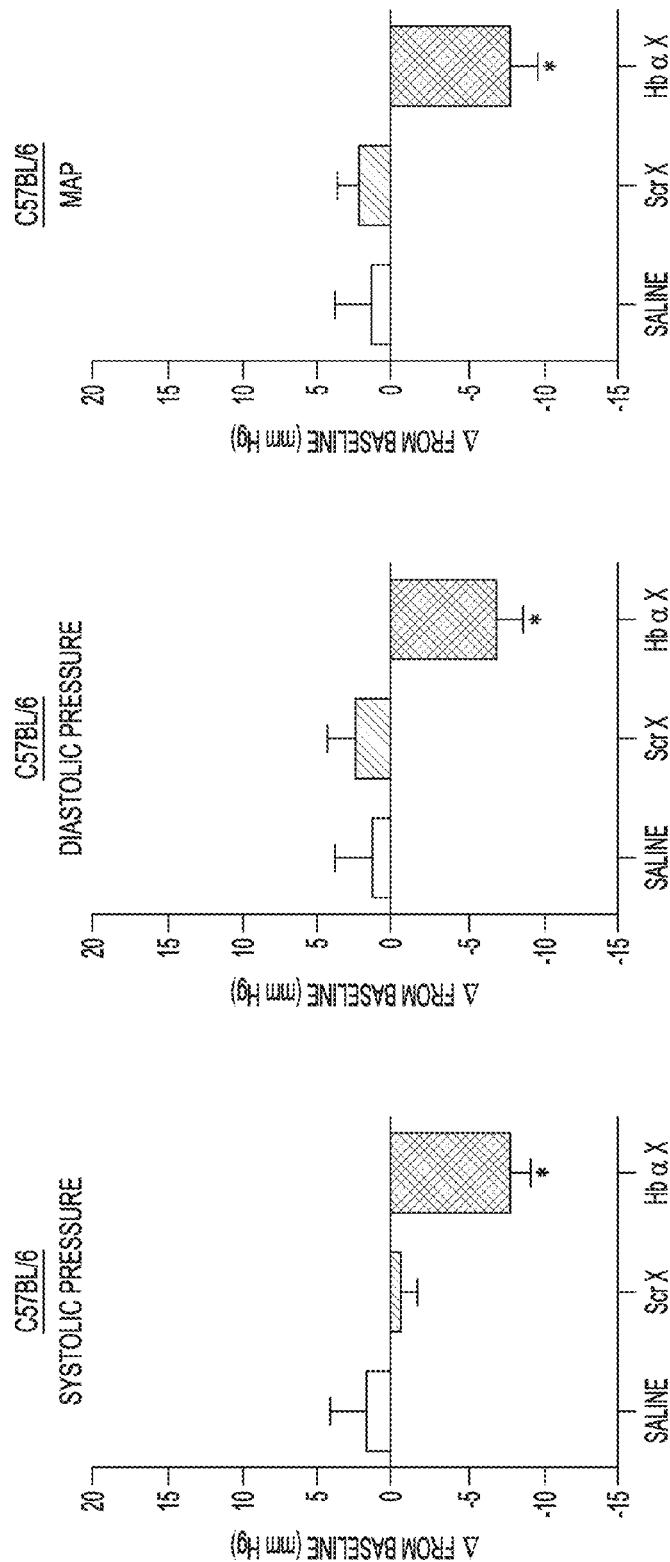

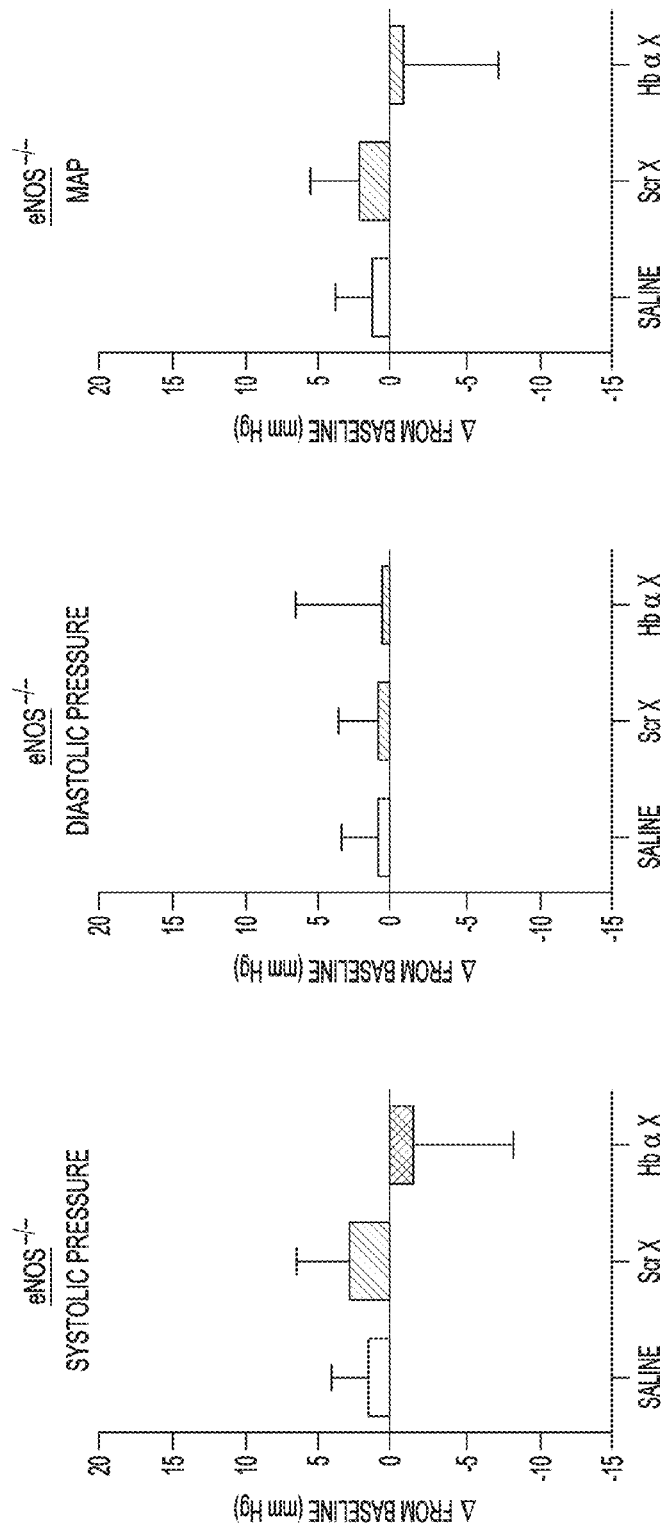

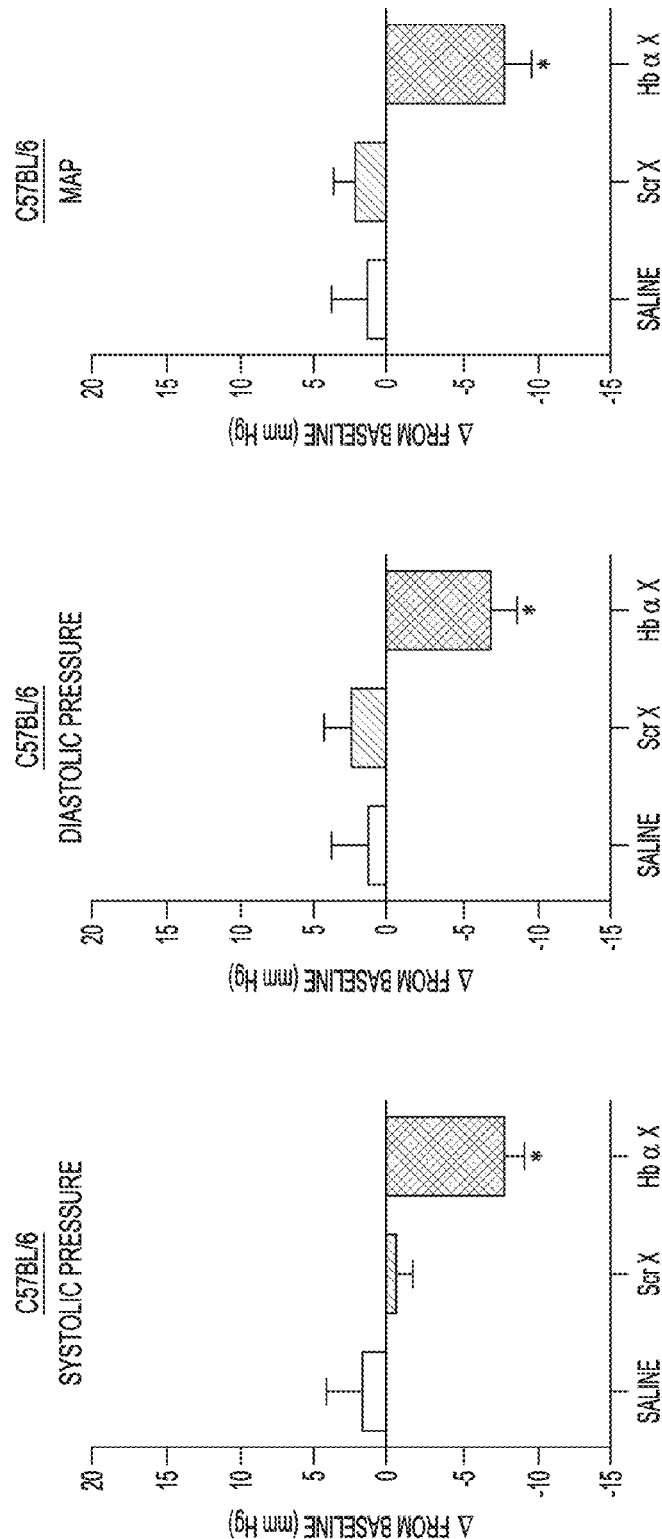
FIG. 30A1, FIG. 30A2, FIG. 30A3

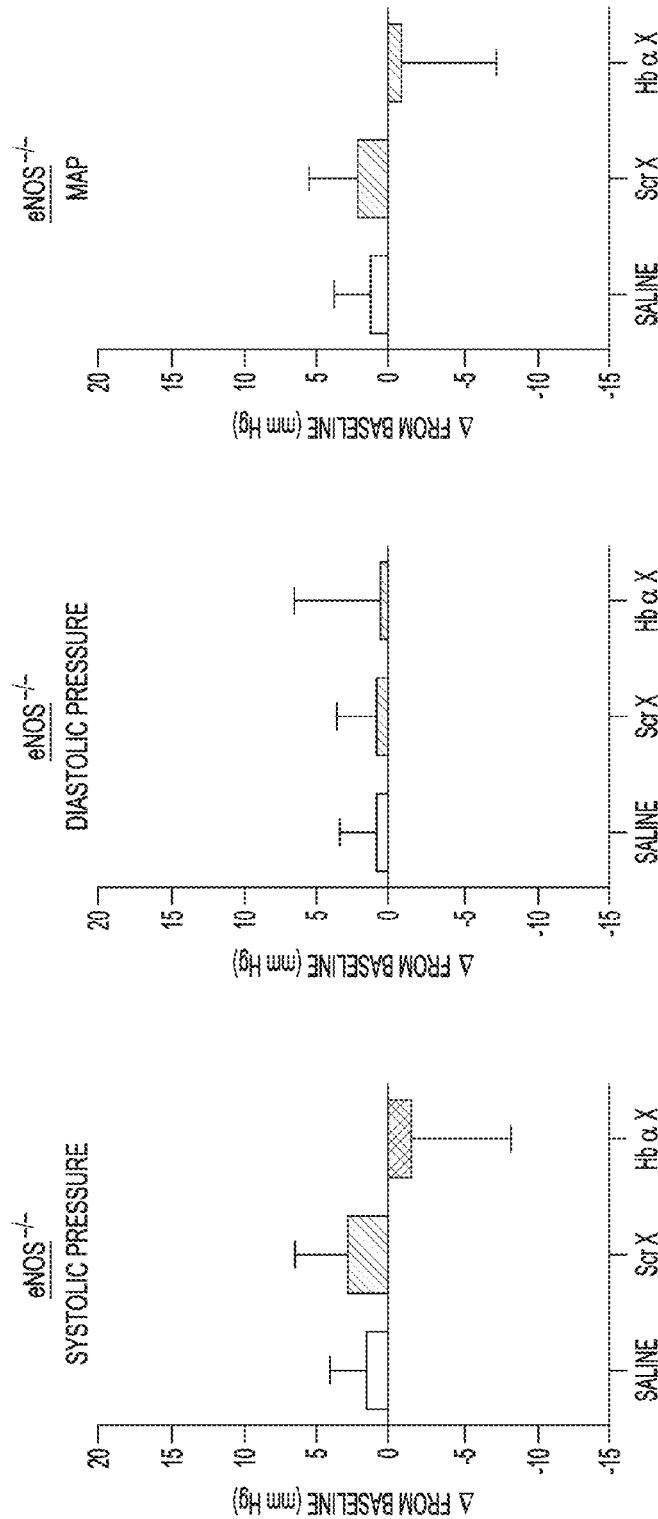

COMPOSITIONS AND METHODS FOR REGULATING ARTERIAL TONE

CROSS REFERENCE TO RELATED APPLICATIONS

This application is a national stage filing of International Application No. PCT/US2013/066186, filed Oct. 22, 2013, which is entitled to priority pursuant to 35 U.S.C. 119(e) to U.S. Provisional Patent Application Ser. No. 61/716,846, filed Oct. 22, 2012, the entire disclosures of which are herein incorporated by reference.

STATEMENT REGARDING FEDERALLY SPONSORED RESEARCH OR DEVELOPMENT

This invention was made with government support under Grant Nos. HL088554, HL112904, HL059337, and HL101871, awarded by The National Institutes of Health. The government has certain rights in the invention.

BACKGROUND

Models of unregulated nitric oxide (NO) diffusion do not consistently account for the biochemistry of NO synthase (NOS)-dependent signaling in many cell systems. For example, endothelial NOS (eNOS) controls blood pressure, blood flow and oxygen delivery through its effect on vascular smooth muscle tone, but the regulation of these processes is not adequately explained by simple NO diffusion from endothelium to smooth muscle.

Control of arteriolar smooth muscle tone is central to regulation of blood pressure, blood flow and oxygen delivery. Nitric oxide (NO) synthase (NOS) in endothelial cells helps to regulate arteriolar tone by signaling smooth muscle relaxation across the myoendothelial junction (MEJ). However, substantial evidence suggests that simple, unregulated NO diffusion does not account for the physiology and biochemistry of NOS-dependent signaling.

Endothelial NOS modulates blood vessel diameter in response to both vasodilators and vasoconstrictors. For example, it is known that during arterial constriction NO from endothelium feeds back on smooth muscle to control the magnitude of the response to a vasoconstrictor (e.g., phenylephrine (PE)). Heme iron oxidation state affects the chemistry of NO-hemoglobin interactions.

There is a long felt need in the art for compositions and methods for regulating the tone of reactive vessels. The present invention satisfies these needs.

SUMMARY OF THE INVENTION

Disclosed herein is a new paradigm in the regulation of NO signaling. The surprising result disclosed herein is that hemoglobin (Hb) α is expressed in arterial endothelial cells (ECs) and enriched at the myoendothelial junction (MEJ), where it regulates the effects of NO on vascular reactivity. It is disclosed herein that endothelial hemoglobin α regulates NOS-dependent cell signaling across the MEJ. Specifically, hemoglobin α is 1) expressed in arteriolar endothelial cells, 2) enriched at the MEJ, 3) in complex with endothelial NOS, and 4) plays a role in the regulation of vascular tone. These effects are specific for the α isoforms of hemoglobin and abrogated by its depletion. It is also disclosed herein that endothelial hemoglobin α heme in the $Fe^{3+}$ state enhances NOS bioactivity. Further, cytochrome B5 reductase 3 catalyzes the reduction of $Fe^{3+}$-state hemoglobin α in endothelial cells. Genetic and pharmacological inhibition of cytochrome B5 reductase 3 enhances NOS-dependent arteriolar relaxation. Thus, endothelial heme oxidation regulates the tone of resistance blood vessels.

One embodiment provides an amino acid sequence comprising LSFPTTKTYFPHFDLSHGSA (SEQ ID NO:1) and conservative amino acid substitutions thereof. In another embodiment, the amino acid sequence comprises LSFPTTKTYF (SEQ ID NO:2) and conservative amino acid substitutions thereof. In one embodiment, the amino acid sequence consists of LSFPTTKTYFPHFDLSHGSA (SEQ ID NO:1) or LSFPTTKTYF (SEQ ID NO:2). Another embodiment provides a plasma membrane permeability sequence. In one embodiment, the plasma membrane permeability sequence comprises an HIV-tat tag sequence of YGRKKRRQRRR (SEQ ID NO:3). Another embodiment provides a pharmaceutical composition comprising the amino acid sequences described herein and a physiologically acceptable carrier.

One embodiment provides a method to increase nitric oxide comprising administering to a subject in need thereof an effective amount of the amino acid sequence or pharmaceutical composition described herein, an antibody directed against Hb α, an antibody directed against SEQ ID NO: 1 or 2, or an inhibitor of Hb a or CytB5R3 activity or expression so as increase nitric oxide.

Another embodiment provides a method to inhibit or reduce vasoconstriction comprising administering to a subject in need thereof an effective amount of the amino acid sequence or pharmaceutical composition described herein, an antibody directed against Hb α, an antibody directed against SEQ ID NO: 1 or 2, or an inhibitor of Hb a or CytB5R3 activity or expression so as to inhibit or reduce vasoconstriction.

A further embodiment provides a method to decrease blood pressure comprising administering to a subject in need thereof an effective amount of the amino acid sequence or pharmaceutical composition described herein, an antibody directed against Hb α, an antibody directed against SEQ ID NO: 1 or 2, or an inhibitor of Hb a or CytB5R3 activity or expression so as to decrease blood pressure.

Another embodiment provides a method to prevent or treat a disease or condition comprising administering to a subject in need thereof an effective amount of the amino acid sequence or pharmaceutical composition described herein, an antibody directed against Hb α, an antibody directed against SEQ ID NO: 1 or 2, or an inhibitor of Hb a or CytB5R3 activity or expression so as to prevent or treat said condition or disease, wherein the disease or condition comprises hypertension, stroke, arteriosclerosis, hemoptysis (e.g., massive), gastrointestinal bleed, epistaxis, migraine headache (e.g., post-prodome) or musculoskeletal injuries (e.g., those in the acute phase), trauma, hemangioma repair (and other intraoperative causes of bleeding), bleeding diatheses, uterine hemorrhage, menorrhagia, septic shock, anaphylactic shock, erectile dysfunction, musculoskeletal/sport injuries (e.g., those in repair phase), or Raynaud's.

One embodiment provides a method to regulate blood pressure comprising administering to a subject in need thereof an effective amount of the amino acid sequence or pharmaceutical composition described herein, an antibody directed against Hb α, an antibody directed against SEQ ID NO: 1 or 2, or an inhibitor of Hb a or CytB5R3 activity or expression so as to regulate blood pressure.

Another embodiment provides a method to relax resistance arterioles comprising administering to a subject in need thereof an effective amount of the amino acid sequence or pharmaceutical composition described herein, an antibody directed against Hb α, an antibody directed against SEQ ID NO: 1 or 2, or an inhibitor of Hb a or CytB5R3 activity or expression so as to relax resistance arterioles.

In one embodiment, the administration is IP or oral. One embodiment further comprises administering inhaled oxygen (e.g., oxygen from an oxygen tank).

In one aspect, the HB α expressed by endothelial cells controls or regulates endothelial-smooth muscle cell communication. It is also disclosed herein that not all endothelial cell tested express Hb α. Surprisingly, this function is unique to Hb α and is abrogated by its genetic depletion. Also disclosed herein is CytB5R3 regulation of the effect of Hb α on nitric oxide bioactivity.

Mechanistically, endothelial Hb α heme iron in the $Fe^{3+}$ state permits NO signaling, and this signaling is shut off when Hb α is reduced to the $Fe^{2+}$ state by endothelial cytochrome B5 reductase 3 (CytB5R3). Genetic and pharmacological inhibition of CytB5R3 increases NO bioactivity in small arteries. These data reveal a novel mechanism by which the regulation of intracellular Hb α oxidation state controls NOS signaling in non-erythroid cells. This paradigm may be relevant to heme-containing globins in a broad range of NOS-containing somatic cells.

The present invention, based on the results disclosed herein, provides compositions and methods to regulate Hb α heme oxidation state in order to regulate both NO diffusion and bioactivation. The present invention further provides compositions and methods for regulating Hb α by modulating its interaction with CytB5R3, the interaction in endothelial cells being a surprising result disclosed herein. Additionally, the present invention provides compositions and methods for causing loss of CytB5R3 or decreased expression or activity levels to inhibit metHb α reduction. The present invention further provides compositions to stimulate CytB5R3 expression or levels or activity to enhance metHb α reduction. The compositions and methods useful for regulating CytB5R3 are also useful for regulating arterial tone.

The present invention encompasses the use of compositions and methods for inhibiting Hb α expression, levels, or activity to inhibit arterial reactivity to a PE type of stimulus but increased reactivity to a regulator such as Ach in the arteries being targeted, unless a NOS inhibitor is also administered. The present invention therefore also encompasses the use of different regulators, alone or in combination.

It is disclosed herein that Hb α interacts with eNOS and compositions and methods are provided for regulating this interaction. In one aspect, the interaction is enhanced, and in another it is inhibited. In one aspect, the compositions and methods of the invention are useful for regulating blood vessel tone by controlling NO diffusion, based on the Hb α interaction with eNOS.

The invention further encompasses compositions and methods useful for inhibiting Hb α expression, levels, or activity to stimulate or cause an increase in NO diffusion across the vessel wall. The invention further encompasses the use of compositions and methods where carbon monoxide ligated $Fe^{2+}$ heme results in increased NO diffusion.

The present invention further provides compositions and methods for regulating blood vessel tone by regulating the interaction of Hb α, eNOS and CytB5R3.

The present invention provides compositions and methods for regulating vascular reactivity and diameter of arteries. The compositions and methods of the invention are also useful for, inter alia, regulating blood pressure, arteriogenesis, anti-inflammatory signaling, and regulating redox signaling.

Useful compounds are disclosed herein, and others in the art can also be used to practice the invention. For example, PTU has been shown herein to regulate endothelial CytB5R3 and to alter vascular reactivity and NO diffusion.

In one embodiment, the composition and methods of the invention are useful for constricting resistance arterioles. In one aspect, administration of a pharmaceutical composition comprising an effective amount of at least one useful molecule of the invention can be used to decrease MEJ Hb oxidation.

The compositions and methods of the invention are useful, for example, in treating massive hemoptysis, GI bleeding, epistaxis, migraine headaches, (post-prodrome), musculoskeletal injuries in the acute phase, trauma, surgical injury, and hemangioma repair and other intraoperative causes of excessive bleeding, bleeding diatheses, uterine hemorrhage or menorrhagia, septic shock, and anaphylactic shock.

The present invention encompasses the use of more than one type of molecule to regulate an activity described herein, including, but not limited to, drugs, DNA, RNA, oligonucleotides, antisense oligonucleotides, siRNA, miRNA, proteins, antibodies, monoclonal antibodies, polyclonal antibodies, and fragments, derivatives, and homologs thereof. The methods further encompass the use of more than one of each type of molecule, alone or in combination.

The compositions and methods of the invention are also useful for increasing MEJ and endothelial Hb α expression, NO oxidation to nitrate and thiol oxidation to dithiols with high $FiO_2$ and $paO_2$.

The present invention further provides compositions and methods useful for relaxing resistance arterioles, as opposed to restricting the resistance arterioles as described above. Examples of specific therapies, compounds, and combinations include, but are not limited to, PTU or novel met reductase inhibitor, xanthine, nitroglycerine or nitrite and occupying Fe2+. This includes the use of local CO, local excess NO, increased NO+ transferred from ironIII: local or systemic "thiol" from the group via NAC, CoA, cyteine, cysteamine, GSH, homocysteine and NO released from Fe2+, light and laser therapies, and heat. The present embodiment can be used to achieve local vasodilation, systemic arteriolar dilation, and can be used in competing technologies.

The present invention also provides for regulating the signal transduction pathway disclosed herein by using molecules that are active in regulating various points in the pathway.

The present application provides pharmaceutical compositions comprising at least one compound of the invention. The present invention further provides for administering a pharmaceutical composition comprising an effective amount of a compound, drug, or molecule of the invention to a subject in need thereof.

The present application further discloses methods for identifying additional compounds useful for practicing the invention. The methods of the invention further encompass the use of molecules effective to practice the invention, including molecules found to be effective using the assays of the invention.

The present invention includes the use of kits comprising a pharmaceutical composition comprising an effective amount of a compound, drug, or molecule of the invention, an applicator, and an instructional material for the use thereof.

Various aspects and embodiments of the invention are described in further detail below.

BRIEF DESCRIPTION OF THE DRAWINGS

FIG. 1, comprising 1A1, 1A2, 1B1, 1B2, 1C1, 1C2, 1D, 1E, 1F1, 1F2, and 1G, —Monomeric Hb α is expressed in ECs and enriched at the MEJ. a, Quantitative Western blot (A1) analysis for Hb α and Hb β expression in coronary EC, MEJ or SMC lysates from cells plated on Transwells or plastic (n≥4), or in fibronectin and gelatin used to coat Transwells. (A2) Red blood cells served as a positive control and GAPDH was used as loading and normalization control for quantitation (bottom left). Immunofluorescence for Hb α (red) and Hb β (green) (bottom right). b, (B1) TEM analysis of Hb α expression in TD (top) or (B2) carotid (bottom) arteries visualized using 10 nm gold beads (black particles). Arrow indicates MEJ. Graphs on the right represent Hb α localization calculated by measuring the number of beads per $\mu m^2$ (n≥7). c, Quantitative Western blot (C1) analysis for Hb α and Hb β expression in isolated TD or carotid arteries. (C2) Tubulin served as a loading control and red blood cells were used as a positive control (n≥3). d, Immunofluorescence of transverse sections from mouse carotid or TD arteries or from a human skeletal muscle arteriole. In all images, red indicates Hb α expression, green shows internal elastic lamina autofluorescence, and blue specifies nuclei. White boxes in mouse TD and carotid artery in left panels indicate the region of interest magnified in the right panel. e, En face images of Hb α expression (red) and Hb β (green) expression in ECs from TD or carotid arteries. Blue staining represents nuclei. f, Western blot analysis of TD artery, EC, MEJ, SMC or red blood cell lysates that were chemically crosslinked (F1) using $BS_3$ to determine quaternary structure of Hb α or not cross-linked (F2). g, mRNA analysis from EC, MEJ and SMC lysates isolated from VCCC, TD and carotid arteries. 18S was used as a normalization factor. In a, b, c, and g open bars represent in vitro data and striped bars indicate ex vivo data. Scale bar in a is 2 μm, b is 0.5 μm, d indicates 30 (TD artery and carotid) or 10 (human skeletal muscle artery) μm and e signifies 10 μm. L is lumen (b, d) and n.s. indicates not significant (b, c). p values are shown for each comparison. All error bars represent s.e.m.

FIG. 7, comprising 7A to 7D—Results from iTRAQ analysis. List of proteins enriched at the MEJ determined by differences in the ratios of MEJ:EC and MEJ:SMC. The Protein ID column represents the specific identification for each of the proteins. The Protein Name indicates the specific protein that was identified and enriched at the MEJ. The Percent Coverage signifies how much of the total protein sequence was identified. The # of Distinct Peptides shows how many peptides were found during the analysis. The Ration of MEJ:EC or MEJ:SMC represents the ratiometric enrichment of each protein the MEJ. Highlighted in green is Hb α showing enrichment compared to EC or SMC monolayers. 7A. Protein ID numbers IPI00930226 to IPI00747810. 7B. Protein ID numbers IPI00219018 to IPI00304596. 7C. Protein ID numbers IPI00549248 to IPI00465028. 7D. Protein ID numbers IPI00010779 to RRRRRnull with protein name REVERSED Gene_symbol=VPs13D.

FIG. 10—The effect of cell type specific transfection of Hb α siRNA in the VCCC. Quantitative immunoblot analysis (10A1—Immunoblot; 10A2—Graph of quantitative results of A1) of Hb α expression in isolated MEJ fractions from VCCCs following cell-type specific knockdown of Hb α using siRNA. GAPDH served as a loading control ($n=3$). Western blot analysis (10B1 and 10B2) of Hb α and eNOS protein expression from ECs transfected with Hb α siRNA in VCCCs. GAPDH served as a loading control. 10B1—Western blot; 10B2—Graph of quantitative results of 10B1) p values are shown for each composition. All error bars represent s.e.m.

FIG. 12, comprising 12A1, 12A2, 12B1, 12B2, 12C1, 12C2, and 12D—mRNA analysis of myoglobin, neuroglobin and cytoglobin in vivo and in vitro and protein expression of cytoglobin in SMCs. mRNA expression of myoglobin in vitro (12A1) or in vivo (12A2); neuroglobin in vitro (12B1) and in vivo (12B2); and cytoglobin in VCCC and in arteries (12C1—cytoglobin in vitro; 12C2—cytoglobin in vivo). The skin or brain was used as a positive control. All samples were normalized to B2M. 12D—Western blot analysis of cytoglobin expression in the VCCC model. GAPDH served as a loading control.

FIG. 13—Hb α stabilizing protein expression in TD arteries and in the VCCC. 13A, Immunofluorescence analysis of AHSP expression (red) in TD arteries. Blue represents nuclei and green indicates autofluorescence from internal elastic lamina. L is lumen. Scale bar is 25 µm. Quantitative Western blot (13B1) of AHSP in the VCCC model depicted graphically in 13B2. GAPDH served as a loading control ($n=3$). p values are indicated for each comparison. n.s. indicates not significant. All error bars represent s.e.m.

FIG. 19—Molecular modeling of potential interaction sites of Hb α, eNOS and CytB5R3. Molecular model of potential docking sites based on the known crystal structures of Hb α (1Y01), CytB5R3 (1UMK) and eNOS (3NOS). The final model consists of a Hb α/CytB5R3 homodimer docked to the eNOS dimer and is represented as a low-resolution model surface representation so that the exact interfaces are not over interpreted.

FIG. 20—Loss-or-gain of CytB5R3 function in ECs alters methemoglobin α reduction. Immunoblots of lysates from transfected ECs with CytB5R3 siRNA (20A1) or CytB5R3-Flag (20A2). Measurements of met-Hb α reduction using ultraviolet-visible spectroscopy from control (20B1), CytB5R3 siRNA (20B2), or CytB5R3-Flag (20B3) transfect ECs. Arrows indicate the progression of the absorbance spectra over time. The absorbance area with light color represents 0-3 minute differences and the dark color shows 3-10 minute changes. (20C) The inset shows regions of interest for met-Hb α reduction. Met-Hb α differences were measured by calculating the change in area for 0-3 and 0-10 minutes for each condition. The graph represents met-Hb α reduction as a function of time.

FIG. 21—Knockdown efficiency of CytB5R3 in isolated arteries and the VCCC and the effects of CytB5R3 loss on eNOS and HB α protein expression. En face immunofluorescence (21A) or quantitative Western blot analysis of CytB5R3 expression in isolated MEJ fractions from VCCCs following cell type specific knockdown using siRNA (21B1—Western blot; 21B2—graphic depiction of quantitation of 21B1). GAPDH served as a loading and normalization control (n=3). Green indicates CytB5R3 expression and blue signifies nuclei. 21C1 shows immunoblots of CytB5R3 and eNOS expression in EC monolayers from the VCCC transfected with CytB5R3 siRNA which are graphically depicted in 21C2. 21D1 and 21D2—Western blot analysis of eNOS and Hb α protein expression at the MEJ from ECs, SMCs or both transfected with CytB5R3 siRNA in VCCCs (21D1) and are graphically depicted in 21D2 (eNOS) and 21D3 (Hbα). Scale bar is 10 µm. p values are shown for each comparison. All error bars represent s.e.m.

FIG. 27—Hb α X peptide does not change eNOS phosphorylation, NO release in untreated and treated coronary endothelial cells. Western blot analysis of pS1177 eNOS and total eNOS from human coronary endothelial cells incubated with Scr X or Hb α X (n=3) (27A1, 27A2, 27A3). Nitrite measurements from unstimulated and stimulated (10 µM bradykinin, 5 minutes) human coronary endothelial cells treated with Scr X or Hb α X (27B1, 27B2, 27B3). In a and b n=3.

FIG. 30—Hb α X peptide decreases blood pressure, but not in eNOS$^{-/-}$ mice. Radio telemetry measurements of systolic, diastolic and mean arterial blood pressure from mice injected with saline, Scr X or Hb α X peptide from C57BL/6 (30A1—Systolic Pressure; 30A2—Diastolic Pressure; 30A3—MAP) or eNOS$^{-/-}$ (30B1—Systolic; 30B2—Diastolic; 30B3—MAP) mice. Significant differences are indicated with * and analyzed by a 1-way ANOVA followed by a Bonferroni's post-hoc test. n≥4 mice for all conditions; error bars indicate s.e.m.

DETAILED DESCRIPTION

Abbreviations and Acronyms

Figure 2A:
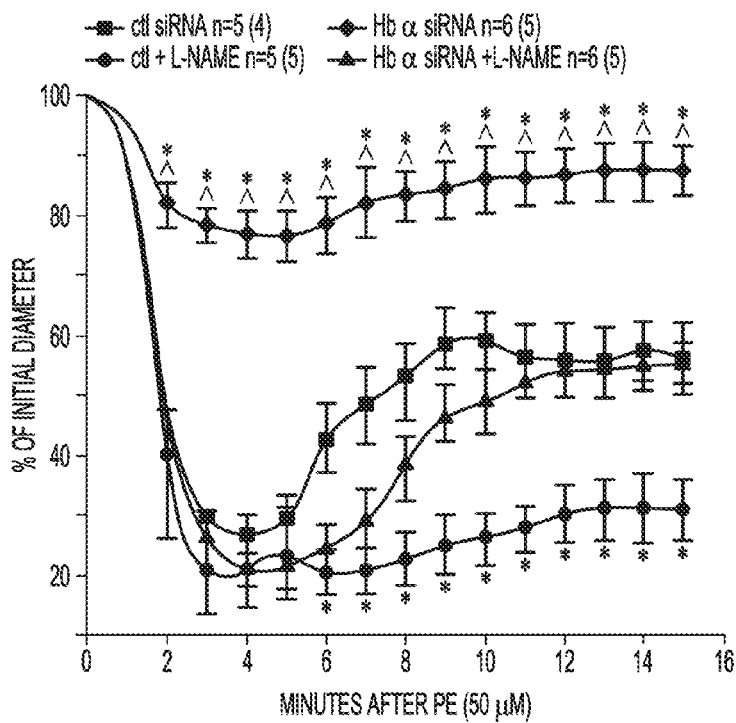
FIG. 2—Hb α regulates vessel tone, NO diffusion and associates with eNOS. a, Time course to 50 μM PE, b dose response to PE and c dose response to Ach on TD arteries treated with control or Hb α siRNA in the presence or absence of L-NAME. In a-c, n indicates the number of arteries; value in parenthesis shows number of mice. d, En face view of a dual immunofluorescence of a mouse TD artery showing Hb α (red) and eNOS (green). The white box in the merge panel indicates the region of interest magnified in the right panel. e, Proximity ligation assay for Hb α and eNOS (red punctuates) in transverse mouse TD artery sections. Inset shows the negative control. f, Western blot analysis from samples co-immunoprecipitated for Hb α and blotted for eNOS from isolated TD and carotid arteries. g, Dual immunofluorescence for Hb α and eNOS on transverse section from a VCCC. Red indicates Hb α and green shows eNOS. h, Co-immunoprecipitation of Hb α Western blotted for eNOS on VCCC lysates. i, Co-immunoprecipitation of purified eNOS-FLAG protein blotted for Hb α. j, Schematic diagram of experimental design illustrating a cannulated vessel with transfected Hb α siRNA showing NO diffusion as a readout. k, NO diffusion results from mouse TD arteries transfected with control or Hb α siRNA (n≥5). 1, Illustration of experimental setup for VCCC experiments. m, NO diffusion results from VCCCs transfected with control or Hb α siRNA. (n≥4). In k striped bars represent ex vivo data and in m open bars indicate in vitro data. In a-c, * shows significance between control siRNA vs. Hb α siRNA, ˆ indicates significance between Hb α siRNA vs. Hb α siRNA+L-NAME and ♦ represents significance between control vs. control+L-NAME. In d-e scale bar is 10 μm and in g 1 μm. In k and m n.s indicates not significant. In e, L indicates the lumen. p values are shown for each comparison. All error bars represent s.e.m.

5-HT—5-hydroxytryptamine
AHSP—alpha hemoglobin stabilizing protein
Ach—acetylcholine
CCRC—cumulative concentration response curves
CO—carbon monoxide
CtyB5R3—cytochrome B5 reductase 3
DETA NONOate—(Z)-1-[2-(2-Aminoethyl)-N-(2-ammonioethyl)amino]diazen-1-ium-1,2-diolate (an NO donor)
EC—endothelial cell (in some experiments it stands for human coronary ECs)
$EC_{50}$—50% of maximal effective concentration
eNOS—endothelial NOS
Hb—hemoglobin
Hb α—hemoglobin alpha
HUVEC—human umbilical vein endothelial cell
HUVSMC—human umbilical vein smooth muscle cell
IBMX—3-isobutyl-1-methylxanthine
IF—immunofluorescence
IP—immunoprecipitation
iTEM—immuno TEM
iTRAQ—isobaric tags for relative and absolute quantitation
L-NAME—L-N$^G$-nitroarginine methyl ester (a NOS inhibitor)
MEJ—myoendothelial junction
NO—nitric oxide
NOA—NO analyzer
NOS—NO synthase
PE—phenylephrine
PLA—proximity ligation assay
PTU—propylthiouracil
siRNA—small interfering RNA
SMC—smooth muscle cell
SNO-NAC—S-nitrosylated N-Acetyl cysteine
TD—thoracodorsal
TEM—transmission electron microscopy
VCCC—vascular cell co-culture
WB—western blot Definitions In describing and claiming the invention, the following terminology will be used in accordance with the definitions set forth below. Unless defined otherwise, all technical and scientific terms used herein have the commonly understood definition by one of ordinary skill in the art to which the invention pertains. Other methods and materials similar or equivalent to those described herein may be useful in the practice or testing of the present invention.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of 20%.

The terms "additional therapeutically active compound" or "additional therapeutic agent," as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As use herein, the terms "administration of" and or "administering" a compound should be understood to mean providing a compound of the invention or a prodrug of a compound of the invention to a subject in need of treatment.

As used herein, an "agonist" is a composition of matter which, when administered to a mammal such as a human, enhances or extends a biological activity attributable to the level or presence of a target compound or molecule of interest in the subject.

As used herein, "alleviating a disease or disorder symptom," means reducing the severity of the symptom or the frequency with which such a symptom is experienced by a subject, or both.

As used herein, an "analog," or "analogue" of a chemical compound is a compound that, by way of example, resembles another in structure but is not necessarily an isomer (e.g., 5-fluorouracil is an analog of thymine).

An "antagonist" is a composition of matter which when administered to a mammal such as a human, inhibits a biological activity attributable to the level or presence of a compound or molecule of interest in the subject.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

An "aptamer" is a compound that is selected in vitro to bind preferentially to another compound (for example, the identified proteins herein). Often, aptamers are nucleic acids or peptides because random sequences can be readily generated from nucleotides or amino acids (both naturally occurring or synthetically made) in large numbers but of course they need not be limited to these.

As used herein, the term "attach," or "attachment," or "attached," or "attaching," used herein interchangeably with "bind," or "binding" or "binds" or "bound" refers to any physical relationship between molecules that results in forming a stable complex, such as a physical relationship between a ligand, such as a peptide or small molecule, with a "binding partner" or "receptor molecule." The relationship may be mediated by physicochemical interactions including, but not limited to, a selective noncovalent association, ionic attraction, hydrogen bonding, covalent bonding, Van der Waals forces or hydrophobic attraction.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biological sample," as used herein, refers to samples obtained from a subject, including, but not limited to, sputum, CSF, blood, serum, plasma, gastric aspirates, throat swabs, skin, hair, tissue, blood, plasma, serum, cells, sweat and urine.

As used herein, the term "carrier molecule" refers to any molecule that is chemically conjugated to the antigen of interest that enables an immune response resulting in antibodies specific to the native antigen.

A "chamber", as used herein, refers to something to which a solution can be added, such as a tube or well of a multiwell plate, etc.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In one embodiment, the first region comprises a first portion and the second region comprises a second portion, whereby, when the first and second portions are arranged in an antiparallel fashion, at least about 50%, including at least about 75%, at least about 90%, or at least about 95% of the nucleotide residues of the first portion are capable of base pairing with nucleotide residues in the second portion. In one embodiment, all nucleotide residues of the first portion are capable of base pairing with nucleotide residues in the second portion.

A "compound," as used herein, refers to any type of substance or agent that is commonly considered a drug, or a candidate for use as a drug, as well as combinations and mixtures of the above. When referring to a compound of the invention, and unless otherwise specified, the term "compound" is intended to encompass not only the specified molecular entity but also its pharmaceutically acceptable, pharmacologically active analogs, including, but not limited to, salts, polymorphs, esters, amides, prodrugs, adducts, conjugates, active metabolites, and the like, where such modifications to the molecular entity are appropriate.

A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

The term "delivery vehicle" refers to any kind of device or material which can be used to deliver compounds in vivo or can be added to a composition comprising compounds administered to a plant or animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of H by an alkyl, acyl, or amino group.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used herein, the term "effector domain" refers to a domain capable of directly interacting with an effector molecule, chemical, or structure in the cytoplasm which is capable of regulating a biochemical pathway.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

As used herein, an "essentially pure" preparation of a particular protein or peptide is a preparation wherein at least about 95%, including at least about 99%, by weight, of the protein or peptide in the preparation is the particular protein or peptide.

As used in the specification and the appended claims, the terms "for example," "for instance," "such as," "including" and the like are meant to introduce examples that further clarify more general subject matter. Unless otherwise specified, these examples are provided only as an aid for understanding the invention, and are not meant to be limiting in any fashion.

The terms "formula" and "structure" are used interchangeably herein.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, including at least about 100 to about 200 nucleotides, including at least about 200 nucleotides to about 300 nucleotides, including at least about 300 to about 350, including at least about 350 nucleotides to about 500 nucleotides, including at least about 500 to about 600, including at least about 600 nucleotides to about 620 nucleotides, including at least about 620 to about 650, and including the embodiment wherein the nucleic acid fragment will be greater than about 650 nucleotides in length.

As used herein, a "functional" molecule is a molecule in a form in which it exhibits a property or activity by which it is characterized. A functional enzyme, for example, is one that exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The term "inhibit," as used herein, refers to the ability of a compound, agent, or method to reduce or impede a described function, level, activity, rate, etc., based on the context in which the term "inhibit" is used. In one embodiment, inhibition is by at least 10%. The term "inhibit" is used interchangeably with "reduce" and "block."

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

The term "inhibitor" as used herein, refers to any compound or agent, the application of which results in the inhibition of a process or function of interest, including, but not limited to, differentiation and activity. Inhibition can be inferred if there is a reduction in the activity or function of interest.

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

The term "modulate", as used herein, refers to changing the level of an activity, function, or process. The term "modulate" encompasses both inhibiting and stimulating an activity, function, or process.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "physiologically acceptable" ester or salt means an ester or salt form of the active ingredient which is compatible with any other ingredients of the pharmaceutical composition, which is not deleterious to the subject to which the composition is to be administered.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

As used herein, the tem "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

As used herein, the tem "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The term "regulate" refers to either stimulating or inhibiting a function or activity of interest.

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (e.g., covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. "Standard" can also refer to an "internal standard", such as an agent or compound which is added at known amounts to a sample and which is useful in determining such things as purification or recovery rates when a sample is processed or subjected to purification or extraction procedures before a marker of interest is measured. Internal standards are often but are not limited to, a purified marker of interest which has been labeled, such as with a radioactive isotope, allowing it to be distinguished from an endogenous substance in a sample.

The term "stimulate" as used herein, means to induce or increase an activity or function level such that it is higher relative to a control value. The stimulation can be via direct or indirect mechanisms. In one aspect, the activity or function is stimulated by at least 10% compared to a control value, including by at least 25%, including by at least 50%. The term "stimulator" as used herein, refers to any composition, compound or agent, the application of which results in the stimulation of a process or function of interest, including, but not limited to, wound healing, angiogenesis, bone healing, osteoblast production and function, and osteoclast production, differentiation, and activity.

A "subject" of analysis, diagnosis, or treatment is an animal. Such animals include mammals, such as a human.

As used herein, a "subject in need thereof" is a patient, animal, mammal, or human, who will benefit from the method of this invention.

As used herein, a "substantially homologous amino acid sequences" includes those amino acid sequences which have at least about 95% homology, including at least about 96% homology, including at least about 97% homology, including at least about 98% homology, and including at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. In one embodiment, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M $NaPO_4$, 1 mM EDTA at 50° C. with washing in 2× standard saline citrate (SSC), 0.1% SDS at 50° C.; such as in 7% (SDS), 0.5 M $NaPO_4$, 1 mM EDTA at 50° C. with washing in 1×SSC, 0.1% SDS at 50° C.; such as 7% SDS, 0.5 M $NaPO_4$, 1 mM EDTA at 50° C. with washing in 0.5×SSC, 0.1% SDS at 50° C.; including in 7% SDS, 0.5 M $NaPO_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215:3: 403-10; Altschul et al., 1997 Nucleic Acids Res. 25:3389-3402). The default settings provided with these programs are suitable for determining substantial similarity of nucleic acid sequences for purposes of the present invention.

The term "substantially pure" describes a compound, e.g., a protein or polypeptide that has been separated from components which naturally accompany it. Typically, a compound is substantially pure when at least 10%, including at least 20%, including at least 50%, including at least 60%, including at least 75%, including at least 90%, and including at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

As used herein, the term "treating" can include prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term to "treat," as used herein, means reducing the frequency with which symptoms are experienced by a patient or subject or administering an agent or compound to reduce the frequency with which symptoms are experienced.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Embodiments

Peptide Modification and Preparation

Peptide preparation is described in the Examples. It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamic, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring or non-standard synthetic amino acids. The peptides of the invention are not limited to products of any of the specific exemplary processes listed herein.

The invention includes the use of beta-alanine (also referred to as β-alanine, β-Ala, bA, and βA, having the structure:

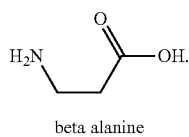

beta alanine

Sequences are provided herein which use the symbol "βA", but in a Sequence Listing "βA" can be provided as "Xaa" and reference in the text of the Sequence Listing indicates that Xaa is beta alanine.

Peptides useful in the present invention, such as standards, or modifications for analysis, may be readily prepared by standard, well-established techniques, such as solid-phase peptide synthesis (SPPS) as described by Stewart et al. in *Solid Phase Peptide Synthesis,* 2nd Edition, 1984, Pierce Chemical Company, Rockford, Ill.; and as described by Bodanszky and Bodanszky in *The Practice of Peptide Synthesis,* 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenyl esters.

Examples of solid phase peptide synthesis methods include the BOC method which utilized tert-butyloxcarbonyl as the α-amino protecting group, and the FMOC method which utilizes 9-fluorenylmethyloxycarbonyl to protect the α-amino of the amino acid residues, both methods of which are well-known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being affected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide may be purified to remove contaminants. In this regard, it will be appreciated that the peptide will be purified so as to meet the standards set out by the appropriate regulatory agencies. Any one of a number of conventional purification procedures may be used to attain the required level of purity including, for example, reversed-phase high performance liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

As discussed, modifications or optimizations of peptide ligands of the invention are within the scope of the application. Modified or optimized peptides are included within the definition of peptide binding ligand. Specifically, a peptide sequence identified can be modified to optimize its potency, pharmacokinetic behavior, stability and/or other biological, physical and chemical properties.

Amino Acid Substitutions

In certain embodiments, the disclosed methods and compositions may involve preparing peptides with one or more substituted amino acid residues.

In various embodiments, the structural, physical and/or therapeutic characteristics of peptide sequences may be optimized by replacing one or more amino acid residues.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-,3- or 4-aminophenylalanine, 2-,3- or 4-chlorophenylalanine, 2-,3- or 4-methylphenylalanine, 2-,3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3',- or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopropionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2, within +/−1, and within +/−0.5 are included in an embodiment.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5);

tryptophan (−3.4). Replacement of amino acids with others of similar hydrophilicity is provided in one embodiment.

Other considerations include the size of the amino acid side chain. For example, it would generally not be desired to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

Linkers

Additionally, modifications encompassed by the invention include introduction of linkers or spacers between the targeting sequence of the binding moiety or binding polypeptide and the detectable label or therapeutic agent. For example, use of such linkers/spacers can improve the relevant properties of the binding peptides (e.g., increase serum stability, etc.). These linkers can include, but are not restricted to, substituted or unsubstituted alkyl chains, polyethylene glycol derivatives, amino acid spacers, sugars, or aliphatic or aromatic spacers common in the art.

For example, suitable linkers include homobifunctional and heterobifunctional cross-linking molecules. The homobifunctional molecules have at least two reactive functional groups, which are the same. The reactive functional groups on a homobifunctional molecule include, for example, aldehyde groups and active ester groups. Homobifunctional molecules having aldehyde groups include, for example, glutaraldehyde and subaraldehyde.

Homobifunctional linker molecules having at least two active ester units include esters of dicarboxylic acids and N-hydroxysuccinimide. Some examples of such N-succinimidyl esters include disuccinimidyl suberate and dithio-bis-(succinimidyl propionate), and their soluble bis-sulfonic acid and bis-sulfonate salts such as their sodium and potassium salts.

Heterobifunctional linker molecules have at least two different reactive groups. Some examples of heterobifunctional reagents containing reactive disulfide bonds include N-succinimidyl 3-(2-pyridyl-dithio)propionate (Carlsson et al., 1978. Biochem. J., 173:723-737), sodium S-4-succinimidyloxycarbonyl-alpha-methylbenzylthiosulfate, and 4-succinimidyloxycarbonyl-alpha-methyl-(2-pyridyldithio)toluene. N-succinimidyl 3-(2-pyridyldithio)propionate is provided in one embodiment. Some examples of heterobifunctional reagents comprising reactive groups having a double bond that reacts with a thiol group include succinimidyl 4-(N-maleimidomethyl)cyclohexahe-1-carboxylate and succinimidyl m-maleimidobenzoate. Other heterobifunctional molecules include succinimidyl 3-(maleimido) propionate, sulfosuccinimidyl 4-(p-maleimido-phenyl)butyrate, sulfosuccinimidyl 4-(N-maleimidomethyl-cyclohexane)-1-carboxylate, maleimidobenzoyl-5N-hydroxy-succinimide ester.

Furthermore, linkers that are combinations of the molecules and/or moieties described above, can also be employed to confer special advantage to the properties of the peptide. Lipid molecules with linkers may be attached to allow formulation of ultrasound bubbles, liposomes or other aggregation based constructs. Such constructs could be employed as agents for targeting and delivery of a diagnostic reporter, a therapeutic agent (e.g., a chemical "warhead" for therapy), or a combination of these.

Constructs employing dimers, multimers, or polymers of one or more peptide ligands of the invention are also contemplated. Indeed, there is ample literature evidence that the binding of low potency peptides or small molecules can be substantially increased by the formation of dimers and multimers. Thus, dimeric and multimeric constructs (both homogeneous and heterogeneous) are within the scope of the instant invention. The polypeptide sequences in the dimeric constructs can be attached at their N- or C-terminus or the N-epsilon nitrogen of a suitably placed lysine moiety (or another function bearing a selectively derivatizable group such as a pendant oxyamino or other nucleophilic group), or can be joined together via one or more linkers (e.g., those discussed herein) employing the appropriate attachment chemistry. This coupling chemistry can include amide, urea, thiourea, oxime, or aminoacetylamide (from chloro- or bromoacetamide derivatives, but is not so limited). For example, methods to prepare dimeric or multimeric constructs of Plec1 binding polypeptides of the invention include at least those discussed below.

Linkers can also be used for attachment to a chelating agent.

Therapeutic Agents

In other embodiments, therapeutic agents, including, but not limited to, cytotoxic agents, anti-angiogenic agents, pro-apoptotic agents, antibiotics, hormones, hormone antagonists, chemokines, drugs, prodrugs, toxins, enzymes or other agents may be used as adjunct therapies when using the agents described herein. Drugs useful in the invention may, for example, possess a pharmaceutical property selected from the group consisting of antimitotic, antikinase, alkylating, antimetabolite, antibiotic, alkaloid, anti-angiogenic, pro-apoptotic agents and combinations thereof.

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

Antibodies and their Preparation

Antibodies directed against proteins, polypeptides, or peptide fragments thereof of the invention may be generated using methods that are well known in the art. For instance, U.S. patent application Ser. No. 07/481,491, which is incorporated by reference herein in its entirety, discloses methods of raising antibodies to peptides. For the production of antibodies, various host animals, including but not limited to rabbits, mice, and rats, can be immunized by injection with a polypeptide or peptide fragment thereof. To increase the immunological response, various adjuvants may be used depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

For the preparation of monoclonal antibodies, any technique which provides for the production of antibody molecules by continuous cell lines in culture may be utilized. For example, the hybridoma technique originally developed by Kohler and Milstein (1975, *Nature* 256:495-497), the trioma technique, the human B-cell hybridoma technique (Kozbor et al., 1983, *Immunology Today* 4:72), and the EBV-hybridoma technique (Cole et al., 1985, in *Monoclonal Antibodies and Cancer Therapy*, Alan R. Liss, Inc., pp. 77-96) may be employed to produce human monoclonal antibodies. In another embodiment, monoclonal antibodies are produced in germ-free animals.

In accordance with the invention, human antibodies may be used and obtained by utilizing human hybridomas (Cote et al., 1983, *Proc. Natl. Acad. Sci. U.S.A.* 80:2026-2030) or by transforming human B cells with EBV virus in vitro (Cole et al., 1985, in *Monoclonal Antibodies and Cancer Therapy*, Alan R. Liss, Inc., pp. 77-96). Furthermore, techniques developed for the production of "chimeric antibodies" (Morrison et al., 1984, *Proc. Natl. Acad. Sci. U.S.A.* 81:6851-6855; Neuberger et al., 1984, *Nature* 312:604-608; Takeda et al., 1985, *Nature* 314:452-454) by splicing the genes from a mouse antibody molecule specific for epitopes of SLLP polypeptides together with genes from a human antibody molecule of appropriate biological activity can be employed; such antibodies are within the scope of the present invention. Once specific monoclonal antibodies have been developed, the preparation of mutants and variants thereof by conventional techniques is also available.

In one embodiment, techniques described for the production of single-chain antibodies (U.S. Pat. No. 4,946,778, incorporated by reference herein in its entirety) are adapted to produce protein-specific single-chain antibodies. In another embodiment, the techniques described for the construction of Fab expression libraries (Huse et al., 1989, *Science* 246:1275-1281) are utilized to allow rapid and easy identification of monoclonal Fab fragments possessing the desired specificity for specific antigens, proteins, derivatives, or analogs of the invention.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment; the Fab fragments which can be generated by treating the antibody molecule with papain and a reducing agent; and Fv fragments.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, *Blood*, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

A nucleic acid encoding the monoclonal antibody obtained using the procedures described herein may be cloned and sequenced using technology which is available in the art, and is described, for example, in Wright et al. (1992, *Critical Rev. in Immunol.* 12(3,4):125-168) and the references cited therein. Further, the antibody of the invention may be "humanized" using the technology described in Wright et al., (supra) and in the references cited therein, and in Gu et al. (1997, *Thrombosis and Hematocyst* 77(4):755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art.

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222:581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

In the production of antibodies, screening for the desired antibody can be accomplished by techniques known in the art, e.g., ELISA (enzyme-linked immunosorbent assay). Antibodies generated in accordance with the present invention may include, but are not limited to, polyclonal, monoclonal, chimeric (i.e., "humanized"), and single chain (recombinant) antibodies, Fab fragments, and fragments produced by a Fab expression library.

Aptamers

The present invention is also directed to useful aptamers. In one embodiment, an aptamer is a compound that is selected in vitro to bind preferentially to another compound (in this case the identified proteins). In one aspect, aptamers are nucleic acids or peptides, because random sequences can be readily generated from nucleotides or amino acids (both naturally occurring or synthetically made) in large numbers but of course they need not be limited to these. In another aspect, the nucleic acid aptamers are short strands of DNA that bind protein targets. In one aspect, the aptamers are oligonucleotide aptamers. Oligonucleotide aptamers are oligonucleotides which can bind to a specific protein sequence of interest. A general method of identifying aptamers is to start with partially degenerate oligonucleotides, and then simultaneously screen the many thousands of oligonucleotides for the ability to bind to a desired protein. The bound oligonucleotide can be eluted from the protein and sequenced to identify the specific recognition sequence. Transfer of large amounts of a chemically stabilized aptamer into cells can result in specific binding to a polypeptide of interest, thereby blocking its function. [For example, see the following publications describing in vitro selection of aptamers: Klug et al., Mol. Biol. Reports 20:97-107 (1994); Wallis et al., Chem. Biol. 2:543-552 (1995); Ellington, Curr. Biol. 4:427-429 (1994); Lato et al., Chem. Biol. 2:291-303 (1995); Conrad et al., Mol. Div. 1:69-78 (1995); and Uphoff et al., Curr. Opin. Struct. Biol. 6:281-287 (1996)].

Aptamers offer advantages over other oligonucleotide-based approaches that artificially interfere with target gene function due to their ability to bind protein products of these genes with high affinity and specificity. However, RNA aptamers can be limited in their ability to target intracellular proteins since even nuclease-resistant aptamers do not efficiently enter the intracellular compartments. Moreover, attempts at expressing RNA aptamers within mammalian cells through vector-based approaches have been hampered by the presence of additional flanking sequences in expressed RNA aptamers, which may alter their functional conformation.

The idea of using single-stranded nucleic acids (DNA and RNA aptamers) to target protein molecules is based on the ability of short sequences (20 mers to 80 mers) to fold into unique 3D conformations that enable them to bind targeted proteins with high affinity and specificity. RNA aptamers have been expressed successfully inside eukaryotic cells, such as yeast and multicellular organisms, and have been shown to have inhibitory effects on their targeted proteins in the cellular environment.

In binding assays, the interaction is binding and the complex formed can be isolated or detected in the reaction mixture. In a particular embodiment, one of the peptides of the complexes described herein, or the test compound or drug candidate is immobilized on a solid phase, e.g., on a microtiter plate, by covalent or non-covalent attachments. Non-covalent attachment generally is accomplished by coating the solid surface with a solution of the peptide and drying. Alternatively, an immobilized antibody, e.g., a monoclonal antibody, specific for the peptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

The present invention also encompasses pharmaceutical and therapeutic compositions comprising the multimeric peptide ligand complexes of the present invention. More particularly, such compounds can be formulated as pharmaceutical compositions using standard pharmaceutically acceptable carriers, fillers, solubilizing agents and stabilizers known to those skilled in the art.

The present invention further provides a pharmaceutical preparation comprising one or more of the compounds, drugs, or molecules of the invention that are active as described herein.

The concentration of compounds, drugs, or molecules in the pharmaceutical composition can vary widely, i.e., from less than about 0.1% by weight, usually being at least about 1% by weight to as much as 20% by weight or more.

The composition may comprise a pharmaceutically acceptable carrier in addition to the active ingredient. The pharmaceutical carrier can be any compatible, non-toxic substance suitable to deliver the peptides o to the patient. For polypeptides, sterile water, alcohol, fats, waxes, and inert solids may be used as the carrier. Pharmaceutically acceptable adjuvants, buffering agents, dispersing agents, and the like, may also be incorporated into the pharmaceutical compositions.

Methods of producing pharmaceutical compositions comprising polypeptides are described in U.S. Pat. Nos. 5,789,543 and 6,207,718. The form used depends on the intended mode of administration and therapeutic application.

Pharmaceutical Compositions and Administration

The invention is also directed to methods of administering the compounds of the invention to a subject.

Pharmaceutical compositions comprising the present compounds are administered to a subject in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

In accordance with one embodiment, a method of treating a subject in need of such treatment is provided. The method comprises administering a pharmaceutical composition comprising at least one compound of the present invention to a subject in need thereof. Compounds identified by the methods of the invention can be administered with known compounds or other medications as well.

The pharmaceutical compositions useful for practicing the invention may be administered to deliver a dose of between 1 ng/kg/day and 100 mg/kg/day.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if desirable, shaping or packaging the product into a desired single- or multi-dose unit.

It will be understood by the skilled artisan that such pharmaceutical compositions are generally suitable for administration to animals of all sorts. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys. The invention is also contemplated for use in contraception for nuisance animals such as rodents.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically, dosages of the compound of the invention which may be administered to an animal, such as a human, range in amount from 1 μg to about 100 g per kilogram of body weight of the animal. While the precise dosage administered will vary depending upon any number of factors, including but not limited to, the type of animal and type of disease state being treated, the age of the animal and the route of administration. In one embodiment, the dosage of the compound will vary from about 1 mg to about 10 g per kilogram of body weight of the animal. In one embodiment, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type of cancer being diagnosed, the type and severity of the condition or disease being treated, the type and age of the animal, etc.

Suitable preparations include injectables, either as liquid solutions or suspensions, however, solid forms suitable for solution in, suspension in, liquid prior to injection, may also be prepared. The preparation may also be emulsified, or the polypeptides encapsulated in liposomes. The active ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants.

The invention also includes a kit comprising the composition of the invention and an instructional material which describes adventitially administering the composition to a cell or a tissue of a subject. In another embodiment, this kit comprises a (e.g., sterile) solvent suitable for dissolving or suspending the composition of the invention prior to administering the compound to the subject.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of using the compositions for diagnostic or identification purposes or of alleviation the diseases or disorders in a cell or a tissue of a mammal. The instructional material of the kit of the invention may, for example, be affixed to a container which contains the multimeric peptide of the invention or be shipped together with a container which contains the peptide. Alternatively, the instructional material may be shipped separately from the container with the intention that the instructional material and the compound be used cooperatively by the recipient.

Other techniques known in the art may be used in the practice of the present invention.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out several embodiments of the present invention, and are not to be construed as limiting in any way the remainder of the disclosure. Therefore, the examples should be construed to encompass any and all variations which become evident as a result of the teaching provided herein.

Additional therapeutic agents may also be administered, including, but not limited to, anti-inflammatory agents, anti-microbial agents, etc.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if desirable, shaping or packaging the product into a desired single- or multi-dose unit.

The compounds of the invention may be administered to, for example, a cell, a tissue, or a subject by any of several methods described herein and by others which are known to those of skill in the art.

The relative amounts of the active ingredient, the pharmaceutically acceptable carrier, and any additional ingredients in a pharmaceutical composition of the invention will vary, depending upon the identity, sex, age, size, and condition of the subject treated and further depending upon the route by which the composition is to be administered.

In addition to the active ingredient, a composition of the invention may further comprise one or more additional pharmaceutically active or therapeutic agents. Particularly contemplated additional agents include anti-emetics and scavengers such as cyanide and cyanate scavengers.

Controlled- or sustained-release formulations of a composition of the invention may be made using conventional technology.

The source of active compound to be formulated will generally depend upon the particular form of the compound. Small organic molecules and peptidyl or oligo fragments can be chemically synthesized and provided in a pure form suitable for pharmaceutical/cosmetic usage. Products of natural extracts can be purified according to techniques known in the art. Recombinant sources of compounds are also available to those of ordinary skill in the art.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts.

The present invention encompasses biologically active analogs, homologs, derivatives, and modifications of the compounds of the invention. Methods for the preparation of such compounds are known in the art.

Liquid derivatives and natural extracts made directly from biological sources may be employed in the compositions of this invention in a concentration (w/w) from about 1 to about 99%. Fractions of natural extracts and protease inhibitors may have a different rage, from about 0.01% to about 20% including from about 1% to about 10% of the composition. Of course, mixtures of the active agents of this invention may be combined and used together in the same formulation, or in serial applications of different formulations.

EXAMPLES

Example 1

Material and Methods

Summary

Human coronary ECs and SMCs were co-cultured and fractionated as previously described. iTRAQ proteomic screening was used to identify and quantify proteins enriched at the MEJ as previously demonstrated. Protein was analyzed using Western blot, immunofluorescence, and immuno TEM, while mRNA was measured using real-time-PCR. Isolated TD arteries were cannulated, pressurized and stimulated with PE or Ach as previously shown or perfused with anaerobic aqueous nitric oxide.

Animals.

Wildtype C57Bl/6 male mice (Taconic) were 8-12 weeks of age. Mice were housed and used in accordance with University of Virginia Animal Care and Use Committee guidelines.

Antibodies.

All antibodies source, application, concentration, and company purchased from are listed in Table below Blood Vessel Isolation.

Mice were sacrificed with $CO_2$ asphyxiation followed by thoracodorsal (TD) artery, mesenteric artery, epigastric abdominal feed artery, carotid artery and aorta isolation. As described in[1], isolated arteries were placed into a Krebs-HEPES buffer supplemented with 1% BSA and washed extensively abluminally and luminally using vessel cannulation to remove red blood cells. Arteries for immunolabeling were isolated from mice that were sacrificed with $CO_2$ and perfused transcardially with 5 mL of heparinized phosphate-buffered saline followed by 5 mL of 4% paraformaldehyde, or 0.5% glutaraldehyde/4% paraformaldehyde for immuno transmission electron microscopy (iTEM). Arteries were then isolated and fixed for an additional 30 minutes.

Vascular Cell Co-Culture (VCCC) Construction.

Human primary coronary endothelial cells (ECs) and smooth muscle cells (SMCs) (Lonza) were co-cultured as previously described[2,3]. Briefly, ECs were cultured in MCDB 131 (Gibco) supplemented with an EGM-2MV bullet kit (Lonza) plus 2 mM L-glutamine (Gibco). SMCs were cultured in DMEM/F12 (Gibco) supplemented with a SMGM-2 bullet kit (Lonza). Human umbilical vein ECs (HUVEC) or SMCs (HUVSMCs) (Cell Applications Inc.) were grown in M199 media supplemented with 10% fetal bovine serum (Gibco), 2 mM L-glutamine (Gibco), and penicillin (2 mM)/streptomycin (50 U/mL) (Gibco). In addition, EC media was supplemented with endothelial growth supplement (5 µg/mL, BD Biosciences) and 5 µg/mL of sodium heparin (Fisher Scientific). Following cell propagation, $9 \times 10^4$ SMCs were plated on a single Transwell (24 mm) for 24 hours, followed by the addition of $3.6 \times 10^5$ ECs plated on the opposite side of the same Transwell. For 12 mm Transwells, $1.9 \times 10^4$ SMCs and $9 \times 10^4$ ECs were plated. Cells were co-cultured for an additional 72 hours.

VCCC Transfections.

VCCCs were constructed as described above. Following 24 hours post EC-SMC co culture, 2.5 µL of siPORT™ NeoFX™ (Ambion) and 100 nmol/L of siRNA or control non-targeting siRNA (ThermoFisher) (See Table below) were mixed in a 1 mL of Opti-MEM (Gibco). siRNA was added to EC only, SMC only or both for 48 hours. Samples were harvested for knockdown efficiency or used for NO assays.

In Vitro VCCC Fractionation.

In vitro EC, myoendothelial junction (MEJ) or SMC lysates were isolated from VCCCs as previously described[3].

cGMP Assay.

Isolated arteries or VCCCs were pretreated 30 minutes prior to PE stimulation with the phosphodiesterase inhibitor 3-isobutyl-1-methylxanthine (IBMX-0.5 mM) and 100 µM L-Nitro-Arginine Methyl Ester L-NAME. Following PE stimulation (50 µM), samples were isolated and lysed in buffer provided in the cGMP XP® Assay kit (Cell Signaling) and the procedure was performed according to manufacturer instructions. A standard curve of known cGMP concentrations was used to determine the cGMP concentrations in the experimental samples. Results were then normalized to protein concentration.

Isobaric Tag for Relative and Quantitation Proteomics (iTRAQ).

The EC, MEJ, and SMC protein lysates were isolated as described above. Samples were frozen and shipped to the Yale Proteomics Facility (Yale University, New Haven, Conn.) and detailed procedures were performed as previously described[4]. Briefly, 25 µg of each of the lysates were reduced and cysteines blocked as described in iTRAQ™ kit (Applied Biosciences). Samples were trypsin digested overnight, followed by labeling the N-terminus of lysine residues with iTRAQ labels 113, 115, and 117. Samples were pooled and purified using a strong cation exchange and separated into 20 fractions. Samples were subjected to electrospray ionization using an Applied Biosystems API QSTAR XL mass spectrometer. Results generated were processed using Mascot Distiller and the database was searched using Mascot Server. Protein validation was then confirmed using ProteinProphet. iTRAQ quantitation was performed using Paragon™ search algorithm in ProteinProphet software. Proteins in the MEJ fractions enriched compared to the EC or SMC lysates were considered positive.

Western Blot.

TD or carotid arteries, VCCC fractions or red blood cells were isolated and homogenized in ice cold lysis buffer containing 50 mM Tris-HCL, 150 mM NaCl, 5 mM EDTA, 1% deoxycholate, 1% NP-40 in phosphate buffered saline and pH adjusted to 7.4. Samples were sonicated and subjected to protein electrophoresis using 4-12% Bis-Tris gels (Invitrogen) and transferred to nitrocellulose. Blots were incubated with primary antibodies (see Table below) overnight at 4° C. followed by washing. Protein was detected using Licor secondary antibodies (see Table below), visualized and quantitated using Licor Odyssey as previously described[5].

Immuno TEM (ITEM).

Isolated TD arteries or carotid arteries were fixed as described above, embedded in LR White as previously described[3] and labeled with primary and secondary antibodies (see Table below). Images were taken on a Joel 1220 electron microscope and gold bead quantitation was performed by as previously described[3].

Immunostaining.

Immunostaining on paraffin sections from VCCC or isolated arteries was performed as previously described[1,3]. For en face staining, TD and carotid arteries were cut longitudinally before the immunostaining procedure. Antibodies used are in Table below. All images were acquired using a Fluoview 1000 confocal microscope (Olympus).

Realtime PCR.

Total RNA from arteries was extracted using Trizol (Invitrogen) whereas total RNA from cells was extracted using an RNeasy Mini Kit spin column (Qiagen). RNA purity and concentration was quantified with a NanoDrop spectrophotometer. cDNA synthesis (iScript cDNA Synthesis Kit—BioRad) and subsequent quantitative real-time reverse-transcription polymerase chain reaction (RT-PCR) analysis was performed using SYBR Green (BioRad), as previously described[6]. Gene-specific RT-PCR primers were designed using Primer3 (MIT) (see Table below) and corresponding products were sequenced for validation. Quantitative RT-PCR reactions were run in duplicates and RNA abundance was normalized to beta-2-microglobulin (B2M) or 18S ribosomal RNA.

Chemical Crosslinking.

Fractions from VCCCs, isolated TD arteries or red blood cells were lysed as described above and immediately placed on ice. Samples were dounced for 1 minute using approximately 30 strokes and spun at 10 g at 4° C. Supernatants were removed and final concentration of 5 mM $BS_3$ (ThermoFisher) was added to samples. After 30 minutes, 1 M Tris was added to each sample to quench the $BS_3$ followed by Western blot analysis for quaternary structure determination.

Vasoreactivity.

TD arteries (maximal internal diameter 261.7±4.2 µm) were isolated, cannulated in a pressure myograph (Danish MyoTechnology) and secured with 10.0 nylon sutures as described in[7]. The TD arteries were placed in a circulating bath of Krebs-HEPES and perfused with Krebs-HEPES supplemented with 1% BSA. Arteries were maintained in a no flow state and pressurized at 80 mmHg as previously described'. After 30 minutes of equilibration, phenylephrine (PE, 50 µM) was added to the bath solution and the contractile response was recorded for 15 minutes as described in[8]. Acetylcholine (1 µM) was added to the bath to verify the integrity of the endothelium. Dose response curves were generated by adding cumulative concentrations of PE ($1E^{-9}$-$1E^{-2}$M). For Ach dose responses, vessels were preconstricted with 5-hydroxytryptamine (5-HT, $5\times10^{-8}$ M) followed by cumulative concentrations of Ach ($1E^{-10}$-$3E^{-4}$ M). At the end of the experiments, the solution was replaced by a calcium-free Krebs supplemented with 2 mM ethylen-bis-(oxyethylenenitrolo) tetra-acetic acid (EGTA) and 10 µM sodium nitroprussiate in order to measure the maximal diameter. When indicated, propylthiouracil (PTU 50 µM) or the nitric oxide synthase inhibitor L-NAME (100 µM; Sigma) were added to the bath and intraluminally during the equilibration period. Internal diameters were calculated and results are expressed as a percentage of initial inner diameter (for PE dose responses) or percent dilation (for Ach dose responses). $EC_{50}$ and $E_{max}$ values were calculated as previously described in[9].

TD Artery Endothelium Transfection.

The TD arteries were isolated and cannulated as described above. The vessel lumen was perfused with Krebs-HEPES buffer supplemented with 1% BSA to flush out red blood cells and 100 µL of Nucleofector transfection reagent (HCAEC Nucleofector kit, Lonza) containing 10 nM control, Hb a or CytB5R3 siRNAs (see Table below) was perfused into the lumen. Arteries were then removed from the cannula and the ends ligated with 10-0 nylon sutures to maintain the transfection reagent and siRNA in the blood vessel lumen. Ligated arteries were then transferred to a transfection cuvette (Lonza) containing 100 µL Nucleofector transfection reagent and electroporated using the Nucleofector II Device (Lonza) using setting A-034. Transfected TDA were removed from cuvettes, re-cannulated and perfused with RPMI media+1% BSA to remove residual transfection reagent and siRNA. Arteries were cultured for 15-18 hours at 37° C. in RPMI+1% BSA and used for vasoreactivity studies or processed for immunofluorescence microscopy. To eliminate variability of transfection efficiency and vessel viability, one control siRNA vessel and one Hb α/CytBSR3 vessel were transfected daily.

Generation of Anaerobic Nitric Oxide.

Anaerobic aqueous NO was generated by bubbling 100% helium into a beaker containing deionized water. Following 30 minutes, 99.5% NO. gas was bubbled for an additional 40 minutes giving a final saturated concentration of approximately 1.7 mM.

Nitric Oxide Diffusion Assay.

Both ECs and SMCs were cultured on 12 mm Transwells as described above. After three days of co-culture, media was removed and replaced with 500 µL of Krebs buffer on each side of the Transwells and cells were allowed to equilibrate for 15 minutes. Next, 100 µL of anaerobic aqueous NO was added to the 500 µLs of Kreb's buffer on the EC side of the Transwell. After 5 minutes, 100 µL of Krebs buffer was immediately removed and injected into a Seivers Nitric Oxide Analyzer (NOA). Data was quantified using Origin Pro 6.0 by calculating the area under the peak over time. Differences between samples were expressed as µM change. For experiments on ex vivo samples, TD arteries were cannulated (as described above) in puddle of 100 µL of Krebs buffer created by parafilm. Using two pieces of tubing, one piece connected to a manometer and an air tight 25 mL bottle and another tube connected to the air tight bottle and to a glass cannula where the TD artery is mounted, 300 µL of anaerobic NO was added to 3 mL of Kreb's buffer into the air tight bottle. The bottle was pressurized to 80 mmHg allowing for a constant flow of through the lumen of the artery (flow rate was approximately 100 µL/minute). After 8 minutes of flow through the vessel, Krebs's buffer on the abluminal side of the vessel was injected into the NOA. Data was quantified using Origin Pro 6.0 by calculating the area under the peak over time. Differences between samples were expressed as µM change.

Nitric Oxide Consumption Assay.

The EC, MEJ, and SMC lysates or TD arteries and carotid arteries were isolated as described above. Samples were assayed for NO consumption as previously described[10]. Briefly, a 40 mM stock solution of the NO donor (Z)-1-[2-(2-Aminoethyl)-N-(2-ammonioethyl)amino]diazen-1-ium-1,2-diolate (DETA NONOate) in PBS was added to a glass vessel continuously purged with helium. This allowed for a continuous liberation of NO inducing a signal of approximately 50 mV due to decay DETA NONOate decay. Once the signal stabilized, 100 µg of each sample was injected. Measurements of decreased NO signal were recorded and quantified using Origin Pro 6.0 by calculating the area under the peak over time. NO gas standards were used to generate a standard curve used determine the NO consumed in each sample.

UV-Visible Spectrometry.

Isolated protein from VCCC fractions (500 µg) or TD arteries (500 µg) were placed in to a 96 well plate using a volume of 250 µL. Freshly isolated human blood or methemoglobin (Sigma) were used as standards. Samples were read using a FLUOstar Omega star plate reader (BMG Labtech) by measuring the absorbance from 220-800 nm. Data was plotted in Origin Pro 6.0 to generate curves and to compare samples.

Met-Hb α Reduction Assay.

Figures 4G, 4H:
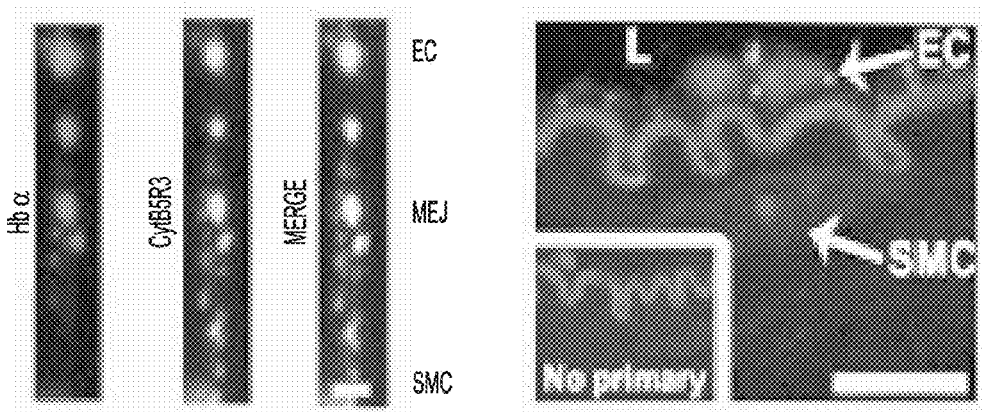
FIG. 4—CytB5R3 expression and activity play a role in vasomotor tone and NO diffusion. a, Immunofluorescence of CytB5R3 expression (red) and nuclei (blue). Green represents autofluorescence from internal elastic lamina. b, TEM analysis of CytB5R3 expression at the MEJ (black particles) in vivo. c, Western blot analysis of CytB5R3 in TD arteries and d in VCCC. e, Immunofluorescence of CytB5R3 expression in the VCCC. Red shows CytB5R3 and green indicates F-actin. f, En face view of a dual immunofluorescence labeling of a mouse TD artery showing Hb α (red) and CyB5R3 (green) in upper panels. White box in the merge image in the lower left panel shows the region of interest magnified in the lower right panel. g, Colocalization of CytB5R3 (red) and Hb α (green) on a transverse section from the VCCC. h, Proximity ligation assay for Hb α and CytB5R3 (red punctuates) on transverse mouse TD artery sections. Inset shows the negative control. Green shows internal elastic lamina autofluorescence. i, Western blot analysis from samples co-immunoprecipitated for Hb α and blotted for CytB5R3 from isolated TD and carotid arteries, VCCC or purified proteins. j, Time course to 50 μM PE, k dose response to PE and 1 dose response to Ach on TD arteries treated with control or Hb α siRNA in the presence or absence of L-NAME. In j-l, n indicates the number of arteries; value in parenthesis shows number of mice. m, Schematic of experimental setup for NO diffusion assay in a cannulated artery that was transfected with CytB5R3 siRNA. n, Results from NO diffusion experiment in mouse TD arteries with genetic knockdown of CytB5R3 expression (n≥3). o, Illustration showing the experimental setup for VCCC experiments. p, NO diffusion results from VCCCs transfected with control or CytB5R3 siRNA (n=4). In n striped bars indicate ex vivo data and in p open bars represent in vitro data. In j-l * shows significance between control siRNA vs. CytB5R3 siRNA, ˆ indicates significance between CytB5R3 siRNA and CytB5R3 siRNA+L-NAME and ♦ represents significance between control vs. control+L-NAME. a, Scale bar is 10 μm, b is 0.25 μm, e is 5 μm, f, h are 10 μm and g is 1 μm. In a and h L indicates lumen. p values are indicated for each comparison. All error bars represent s.e.m.

Human coronary ECs were seeded in 100 mm dishes and grown to approximately 80% confluency. ECs were then transfected with CytB5R3 siRNA (see Table below) or CytB5R3-Flag tagged plasmid (5 µg, Origene) using Lipofectamine 2000 (Life Sciences) according to manufacturer directions. After 24 hours, ECs were stimulated with the calcium ionophore A23187 (1 µM) for 1 minute to maximize CytB5R3 activity. ECs were then lysed, protein concentrations were measured and transfection efficiency was assessed via Western blot analysis as described above. Using a total of 300 µg of protein, EC lysates were mixed with purified Hb α chains (25 µg/µl final concentration—isolated as described above), normalized to equal volumes with lysis buffer and placed immediately on ice. Just before the spectral reading, 50 μM NADH (required for CytB5R3 activity) was mixed with each sample and the full UV-visible spectrum (220-700) was measured at 0, 3 and 10 minutes. Changes in met-Hb α reduction was calculated by measuring the area between the 510-575 and 610-650 nm peaks for the 0, 3, and 10 minute time points as shown in FIG. 4s (inset) using Origin Pro statistical software. Areas between 510-575 and 610-650 nm were summed for each time point and the sum area at time 0 minute was subtracted from the area at 3 and 10 minutes in order to quantify the change in met-Hb α reduction.

Iron Oxidation State Assay.

Isolated protein from TD arteries (200 μg) or VCCC (100 μg) were divided into three tubes: one tube containing an untreated lysate, another with 20 mM of ascorbic acid, and one with 0.6 mM potassium ferricyanide. Samples were incubated for 30 minutes at room temperature. After 30 minutes, 10 mM of Ferene S, which only binds $Fe^{2+}$, was added, and incubated for 1 hr at 37° C. followed by measuring absorbance of Ferene S at 595 nm. A standard curve was generated using the ascorbic acid and potassium ferricyanide values. Untreated samples were calculated using the standard curve and expressed as a % of $Fe^{2+}$ and $Fe^{3+}$. The specificity for hemoglobin was determined by knocking down Hb α with siRNA.

Co-Immunoprecipitation.

Co-immunoprecipitations were performed as described in[1]. Briefly, protein fractions were incubated with primary antibodies (see Table below) overnight at 4° C. The following day, Dynabeads® were added to samples for 2 hours at room temperature. Next, a magnet was used to isolate beads with the protein complexes. Laemmli sample buffer was added to beads and boiled for 1 minute. Beads were isolated and the proteins were subjected to Western blot analysis as described above.

For purified proteins, Hb α chains were isolated as previously described with modifications[11,12]. Lyophilized hemoglobin (Sigma) was brought up to a final concentration of 50 mg/mL in 10 mM Tris, pH 8.0 at 4° C. Hemoglobin was passed through a DEAE Hi Trap column (GE Healthcare) using high pressure flow chromatograph at a flow rate of 1 mL/minute and Hb α chains were collected as the flow through whereas β chains and tetramers remained bound to the column. Purified FLAG-tagged eNOS and CytB5R3 were purchased from Origene. For immunoprecipitation experiments, 1 μg of each protein was mixed and incubated at 37° C. for 1 hr. Following incubation, anti-FLAG magnetic beads (Sigma) were added to the purified proteins for 1 hr and complexes were precipitated and analyzed using Western blot as described above.

Proximity Ligation Assay (PLA).

Duolink® II fluorescence assay kit (Olink Bioscience) was used according to manufacturer instructions. Briefly, deparaffinized TD artery sections were incubated with primary antibodies (see Table below) overnight at 4° C. The next day, secondary antibodies conjugated with oligonucleotides (PLA probe PLUS and MINUS) were added to the sections and washed. Next, a ligation solution containing a ligase and two oligonucleotides was added to the tissue allowing for the PLA probe hybridization, only if both PLA probes were less than 30 nm apart. Lastly, an amplification solution consisting of nucleotides and fluorescently labeled oligonucleotides was added along with a polymerase. Rolling-circle amplification was then initiated and fluorescently labeled oligonucleotides were hybridized to the amplification product. Arteries were then imaged using an Olympus Fluoview 1000 confocal microscope.

$NO_x$ Measurements.

Total NO metabolites (NOx) were assayed as described[8]. Briefly, samples were injected in a purged glass vessel heated to 95° C. containing a solution of vanadium (III) chloride (50 mM) in hydrochloric acid (1 mM), with a continuous purged stream of helium. NO signal was measured by chemiluminescence using a NO analyzer.

Measurement of S-nitrosylated N-acetyl Cysteine (SNO-NAC).

Experimental setup was performed similarly as describe above in Nitric oxide diffusion assay. Isolated arteries were cannulated and placed into a puddle of 150 μl NAC (1 μM) on the ablumenal side, which served as a S-nitrosothiol bait reactant[13]. Next, using a manometer connected to a pressurized bottle (described above), a solution of DETA NONOate (100 μM) was passed through the lumen of the vessel for 1 hr. The puddle of NAC was then subjected to the copper/cysteine assay to measure SNO-NAC described in[14]. For VCCCs, 1 μM NAC in KREBs was placed on the SMCs of the VCCC and a solution of DETA NONOate (100 04) in Krebs was then added to the EC side of Transwell. After 1 hr, the buffer was measured for total SNO-NAC by the copper/cysteine assay.

Modeling of Hb α, CytB5R3, and eNOS.

The crystal structures of Hb α (1Y01) and eNOS (3NOS) had small regions of the proteins not built into the crystal structure model. SWISS-MODEL[15,16] was used to build in the missing regions using the original structure as the template. The GRAMM-X server[17,18,19] was used to generate 20 poses of Hb α and CytB5R3 (1UMK). Of the 20 poses, two poses were removed as possibilities because the dimer interface had the least buried surface area. The remaining 18 poses were evaluated based on the accessibility of three CytB5R3 residues (K41, K125, and K162) identified as essential for binding to CytB5[20]. The remaining 18 poses were analyzed based on frequency of the interaction with face of Hb α and the sampling of orientations with respect to the face of Hb α. Nine poses remained which clustered into six groups based on the interaction face of Hb α; three groups with a single pose (which were not used for further analysis) and three groups each with two poses (clusters). The poses in one of the three clusters had very different CytB5R3 interactions with Hb α and; therefore, were not further analyzed. In the remaining two clusters, two pose were very similar in the orientation of CytB5R3 with respect to the face of Hb α and two poses interacted with the same surface of Hb α, but the orientation of CytB5R3 were 180° rotated with respect to each other. A representative Hb α/CytB5R3 homodimer from each of these two clusters was docked to the eNOS dimer. Of the 40 poses (20 poses for each Hb α/CytB5R3 docked), 27 docked to an interface between the two eNOS monomers. The poses had many orientations at the interface; however, there was a significant bias to the interface. To generate the final model, the symmetry mate was generated such that the other docking site of eNOS was occupied and the stoichiometry was 1:1:1. The low-resolution model shown is only one of the poses and is shown in surface representation so that the exact interfaces are not over-interpreted.

Statistics.

Statistics were performed using Origin Pro 6.0 software. For multiple comparisons, statistics were performed using a one-way by pairwise analysis. A Student's t-test was used for individual comparisons if normally distributed. For vascular reactivity cumulative concentration response curves, a two ANOVA was performed followed by a Bonferroni post-hoc test using GraphPad Prism 5.

TABLE 3

Table 3 - Catalog of Antibodies.

| Antibody | Species | Application | Conc. | Company | Cat. Number |
|---|---|---|---|---|---|
| Hb α | rabbit | WB, IF, IP, iTEM | 1:1000, 1:500, 1:50 1:50 | Abcam | ab102758 |
| Hb α | goat | PLA | 1:500, 1:100 | Santa Cruz | sc-31109 |
| Hb β | goat | WB | 1:1000 | Santa Cruz | sc-31116 |
| Hb β | mouse | WB | 1:1000 | Santa Cruz | sc-21757 |
| AHSP | rat | IF | 1:500 | Gift from Mitchell Weiss | N/A |
| AHSP | rabbit | WB | 1:1000 | Gift from Mitchell Weiss | N/A |
| Cytoglobin | rabbit | WB | 1:1000 | Proteintech | 13317-1-AP |
| CyB5R3 | rabbit | WB, IF, IP, PLA, iTEM | 1:1000, 1:500, 1:50 1:100, 1:50 | Proteintech | 10894-1-AP |
| eNOS | mouse | WB, IF | 1:1000, 1:500 | BD Biosciences | 610296 |
| eNOS | rabbit | PLA | 1:100 | Sigma | N 3893 |
| tubulin | rabbit | WB | 1:10,000 | Sigma | T 2200 |
| GAPDH | mouse | WB | 1:10,000 | Invitrogen | 39-8600 |
| Alexa488 | mouse | IF | 1:500 | Invitrogen | A-21442 |
| Alexa594 | rabbit | IF | 1:500 | Invitrogen | A-21202 |
| Licor 700 | mouse | WB | 1:5000 | Licor | 926-32220 |
| Licor 800 | rabbit | WB | 1:5000 | Licor | 926-32211 |
| Gold beads (10 nm) | rabbit | iTEM | 1:50 | Electron Microscopy Services | 25109 |

Lists are the antibodies used, the species the antibody was produced in, application for the antibody, the concentration of antibody used for each application respectively, the company where the antibody was produced and the catalog number.
WB—Western blot,
IP-immunoflourescence,
IP—immunoprecipitation,
iTEM—immuno transmission microscopy,
PLA—proximity ligation assay.

TABLE 4

| Gene (Accession number) | Primer Sequence (5'-3') | Product Size (bp) |
|---|---|---|
| h-Hb α (NM_000558.3) | (F) TGGACCCGGTCAACTTCAA (R) GAGGCTCCAGCTTAACGGTAT | 160 |
| m-Hb α (NM_001218.2) | (F) TGCTCTCTGGGGAAGACAAA (R) GAGCCCTGCCTTACATCAA | 154 |
| h, m-Cytoglobin (NM_134268.4, NM_030206.4) | (F) tcggccaagcagtacttcag (R) ACCTCCAGAATGACCCCAGA | 239 |
| b-Neuroglobin (NM_021257.3) | (F) TCCTGGACCACATCAGGAAG (R) TCACCCACTGTCGAGAAGGA | 151 |
| m-Neuroglobin (NM_022414.2) | (F) TCCTGGACCACATCAGGAAG (R) CAGGCACTTCTCCAGCATGT | 182 |
| h-Myoglobin (NM_005368.2) | (F) GGCTCTTTAAGGGTCACCCA (R) GGGGCTTAATCTCTGCCTCA | 174 |
| m-Myoglobin (NM_001164047.1) | (F) CTGAATGTCTGGGGGAAGGT (R) TTGGGCTAGAGGCTGGATCT | 243 |

The left side lists the gene name and accession number in which primers were designed.
The middle column shows the forward and reverse 5'-3' primer sequences.
The right column indicates the approximate base pair size of each product.
h-human,
m-mouse.

TABLE 5

| siRNA | siRNA ID (Ambion) | Sense (5'-3') | Anti-sense (5'-3') | Application | Conc. |
|---|---|---|---|---|---|
| m-Hb-α | S67374 | GCAUGCCUCUC UGGACAAATT (SEQ NO: 24) | UUUGUCCAGAG AGGGAUGCAC (SEQ NO: 25) | vessel transfection | 10 nM |
| m-Hb-α | S67376 | GACCUACUUCC CUCACUUUTT (SEQ NO: 26) | AAAGUGAGGGA AGUAGGUCTT (SEQ NO: 27) | vessel transfection | 10 nM |
| h-Hb-α | S194496 | CAAAUACCGUU AAGCUGGATT (SEQ NO: 28) | UCCAGCUUAAC GGUAUUUGGA (SEQ NO: 29) | VCCC transfection | 100 nM |
| h-Hb-α | S194498 | ACUUCAAGCUC CUAAGCCATT (SEQ NO: 30) | UGGCUUAGGAG CUUGAAGUTG (SEQ NO: 31) | VCCC transfection | 100 nM |

TABLE 5-continued

| siRNA | siRNA ID (Ambion) | Sense (5'-3') | Anti-sense (5'-3') | Application | Conc. |
|---|---|---|---|---|---|
| m-CytB5R3 | S99607 | AGGGCUUCGUG AAUGAGGAUU (SEQ NO: 32) | UCCUCAUUCAC GAAGCCCUCC (SEQ NO: 33) | vessel transfection | 10 nM |
| m-CytB5R3 | S99606 | GGACACCCAUC CCAAGUUUUU (SEQ NO: 34) | AAACUUGGGAU GGGUGUCCUU (SEQ NO: 35) | vessel transfection | 10 nM |
| h-CytB5R3 | S4087 | GGAGGAACUCA GGAACAAAUU (SEQ NO: 36) | UUUGUUCCUGA GUUCCUCCAG (SEQ NO: 37) | VCCC transfection | 100 nM |
| h-CytB5R3 | S4088 | GACAAAAGUC CAACCCUAUU (SEQ NO: 38) | UAGGGUUGGAC UUUUUGUCAG (SEQ NO: 39) | VCCC transfection | 100 nM |

List of siRNA sequences.
The siRNA shows the gene target of interest, the siRNA ID indicates the catalog identification code from Ambion, the targeting sequence shows the sense (5-3') and antisense (3'-5'), the application lists the experiment in which the siRNA was used and the concentration shows how much siRNA was used for each application.
h-human, m-mouse.

Figure 6:
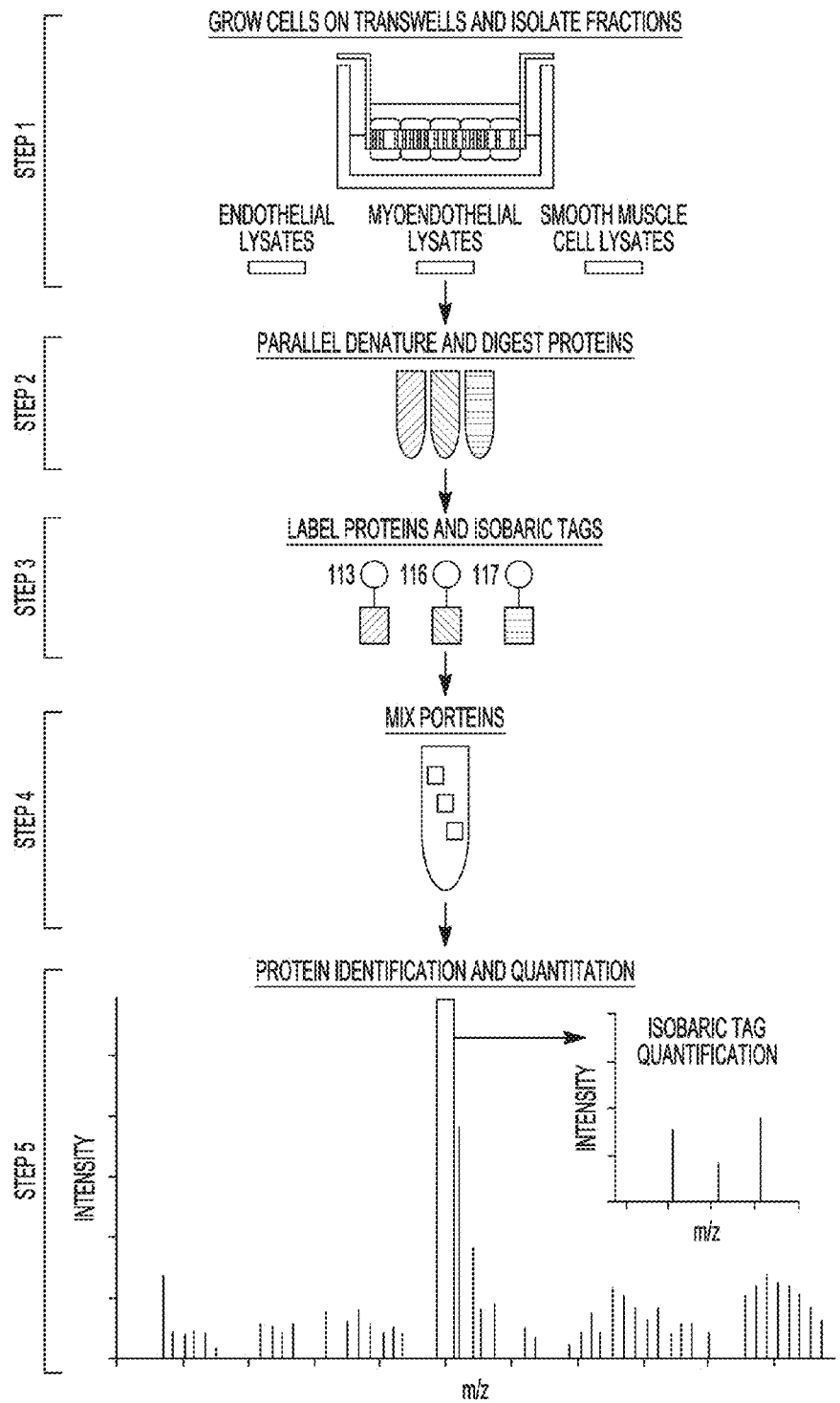
FIG. 6—Flow chart representing the proteomic screen of VCCC lysates using iTRAQ. Step 1, EC and SMC cells were grown on Transwells and EC, MEJ, and SMC fractions were isolated according to materials and methods. Step 2, 25 µgs of EC MEJ and SMC protein were separately reduced and cysteines were blocked as described in the iTRAQ™ kit (Applied Biosystems). Step 3, after overnight trypsin digestion, samples were labeled on the N-terminal amino group and epsilon amino group of lysine residues with iTRAQ tags as follows: EC-iTRAQ 113, MEF-iTRAQ 115 and SMC-iTRAQ 117. The labeled samples were pooled together and subjected to a strong cation exchange column separating the samples into 20 fractions (Step 4). Step 5, samples were subjected to QSTAR XL LC-MS/MS analysis and data was collected by electrospray ionization using an Applied Biosystems API QSTAR XL mass spectrometer. Results generated were processed using Mascot Distiller and the database was searched using Mascot Server, and protein validation was confirmed using ProteinProphet. iTRAQ quantitations performed using Paragon™ search algorithm in ProteinProphet software, Peptide fragments (gray show over peak) and simultaneous quantification of reporter ions (isobaric tags-inset) were used for determination of enriched proteins at the MEJ. Proteins in the MEJ fraction enriched compared to the EC or SMC lysates were considered positive.

PE stimulation of thoracodorsal (TD) arteries ex vivo—and of primary human ECs and vascular smooth muscle cells (SMCs) in the vascular cell co-culture (VCCC) model—reproduced classical NOS- and cGMP-dependent changes in SMC biology (FIG. 5a-d). However, NO did not diffuse into the extracellular space (FIG. 5e-h), consistent with previous work showing compartmentalized NOS signaling at the MEJ, the EC-SMC contact point in the TD and other small arteries and arterioles. Therefore, MEJ proteins that could contribute to local regulation of NO diffusion and biochemistry were studied. A proteomic analysis of MEJs isolated from VCCCs using the isobaric tags for relative and absolute quantitation (iTRAQ) system was performed (FIG. 6). Surprisingly, Hb α was abundant at the MEJ (FIG. 7). Without wishing to be bound by any particular, it was hypothesized that Hb can regulate NO diffusion and biochemistry at the MEJ and the experiments and results directed to that hypothesis are provide below.

Figure 8A:
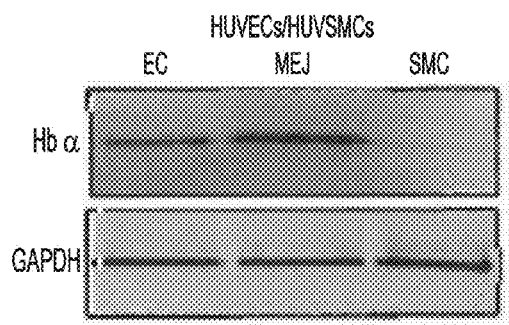
FIG. 8—Hb α is enriched at the MEJ in co-cultured HUVECs and HUVSMCs. 8A Quantitative Western blot analysis of EC, MEJ, and SMC lysates for Hb α. GAPDH was used as a loading and normalization control for 8B, quantitation. ($n=4$). P values are indicated for each comparison. All error bars represent s.e.m.
Figure 8B:
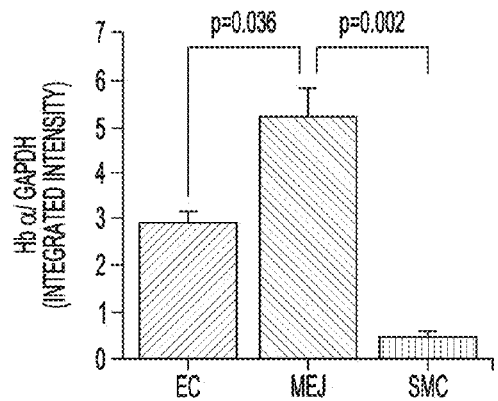
Figure 9:
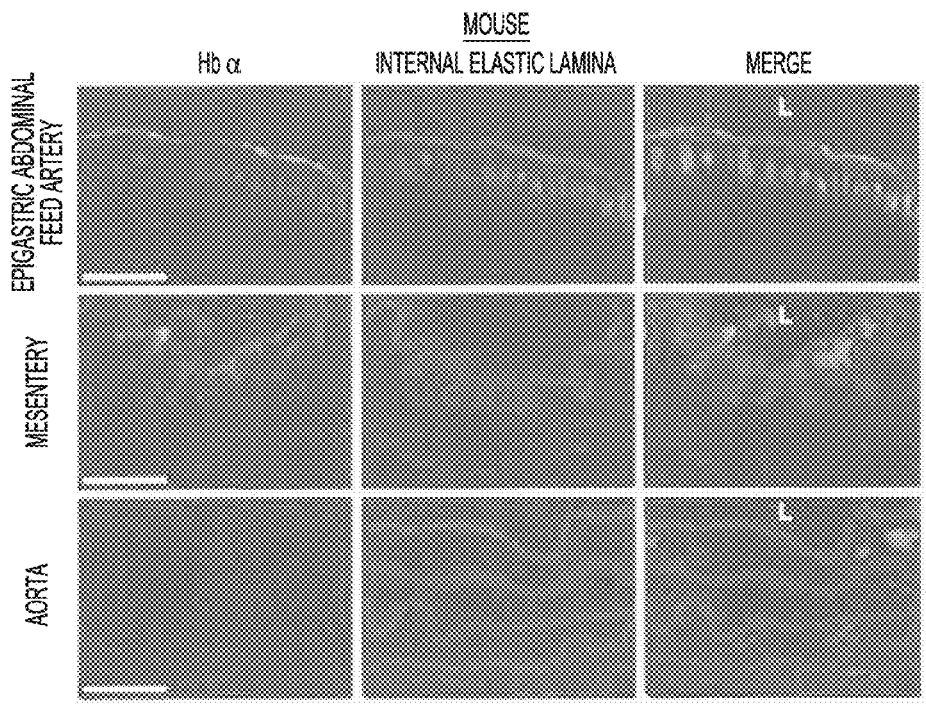
FIG. 9—Expression of Hb α in multiple vascular beds. Immunofluorescence analysis of Hb α expression (red) in mouse epigastric abdominal feed artery, mesenteric artery and aorta. Blue represents nuclei and green indicates autofluorescence from internal elastic lamina. L is lumen. Scale bar is 25 µm.
Figure 11A:
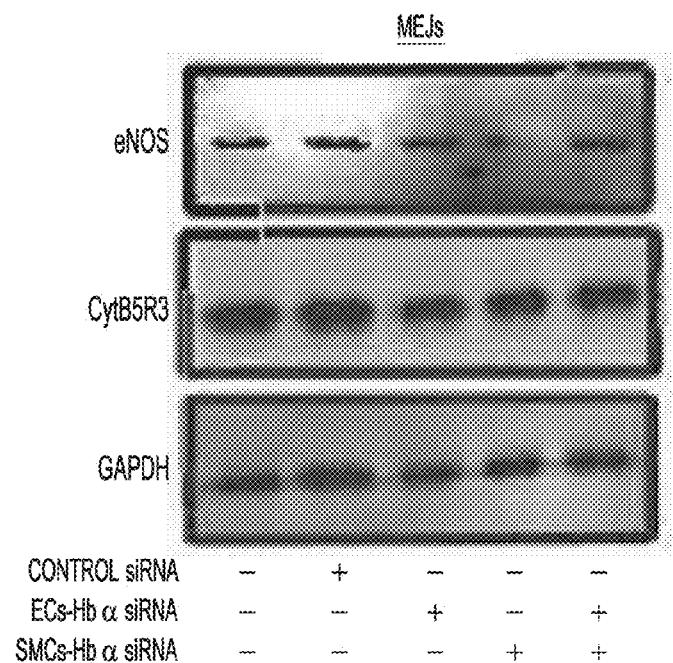
FIG. 11—Effects of decreased Hb α protein on eNOS and CytB5R3 protein expression at the MEJ. Western blot analysis (11A) of CytB5R3 (depicted graphically in 11C) and eNOS (depicted graphically in 11B) protein expression at the MEJ from ECs, SMCs or both transfected with Hb siRNA in VCCCs. GAPDH served as a loading control ($n=3$). n.s. indicates not significant. All error bars represent s.e.m.
Figure 11B:
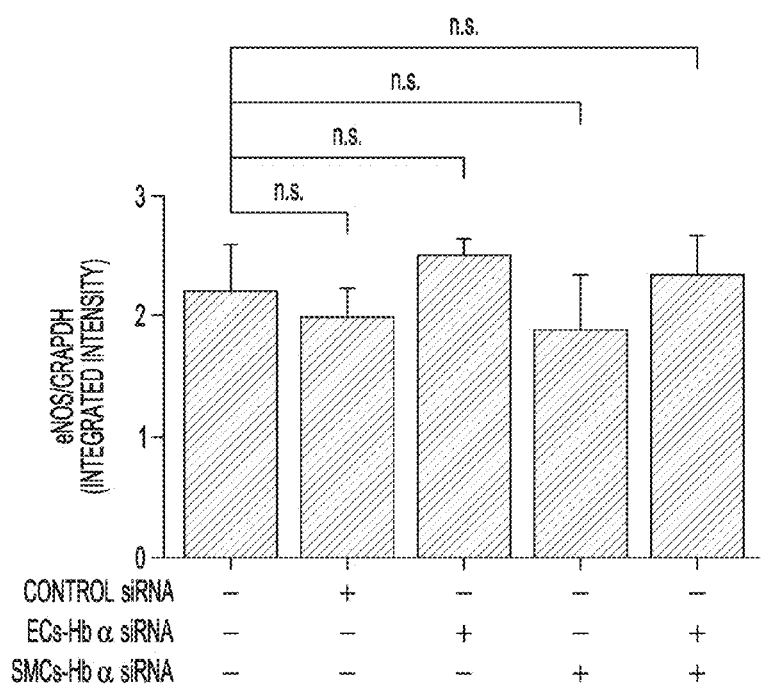
Figure 11C:
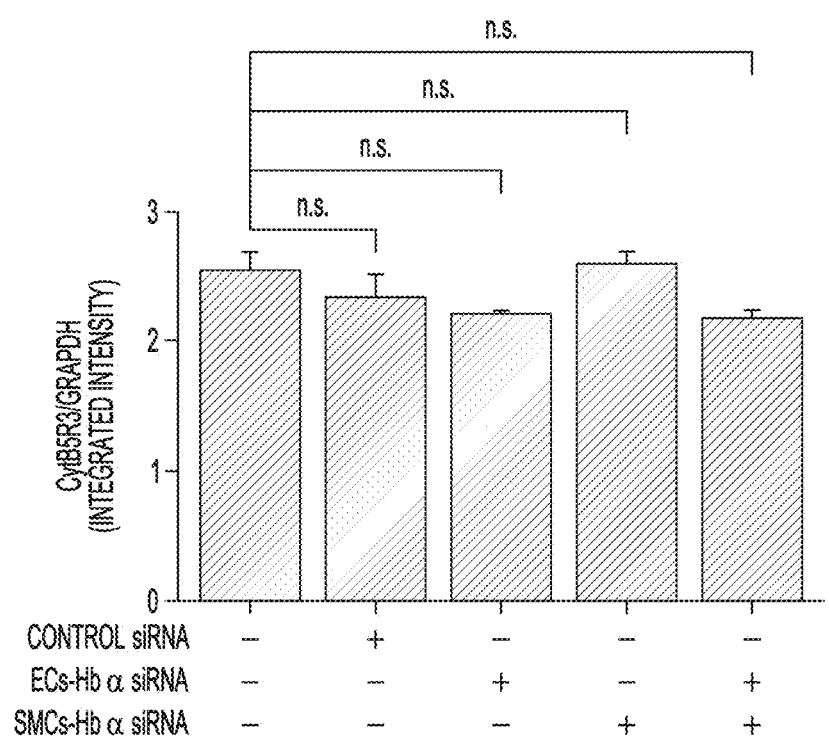

First, the proteomic data using immunoblot and immunofluorescence was confirmed. Hb α protein expression in the VCCC model, but no expression of Hb 13 was demonstrated (FIG. 1a). There was little Hb α expression in human ECs or SMCs grown separately, and there was no Hb α in the fibronectin or gelatin used to coat the VCCC transwells (FIG. 1a). Next, these results were confirmed in co-cultures of different types of ECs and SMCs where MEJs also expressed abundant Hb α (FIG. 8). The MEJ distribution of Hb α in situ was then examined. Gold particles labeling Hb α were abundant in the MEJ of mouse TD arteries visualized by transmission electron microscopy (TEM) (FIG. 1b). In contrast, carotid arteries—conduit arteries which have few MEJs—expressed little Hb α as observed by TEM (FIG. 1b), immunoblot (FIG. 1c), and immunofluorescence (FIG. 1d). These data were consistent in human skeletal muscle arterioles (FIG. 1d) and throughout multiple tissue beds (FIG. 9). Using en face immunofluorescence, punctuate Hb α staining primarily at paracellular junctions of TD—but not carotid—arteries was found, whereas little Hb β was observed (FIG. 1e). Chemical crosslinking analysis revealed that the Hb α was monomeric in TD arteries and the VCCC (FIG. 1f). Next, Hb α mRNA was measured using real-time PCR (FIG. 1g) and established that ECs transfected with Hb α siRNA had decreased protein expression at the MEJ (FIG. 20a) and in the monolayer (FIG. 10b). Loss of Hb α protein expression did not affect eNOS expression in the EC monolayer (FIG. 10b) or at the MEJ (FIG. 11).

Transcripts for other globins including myoglobin, neuroglobin, and cytoglobin were absent in ECs (FIG. 12a-c). Only cytoglobin mRNA and protein were expressed in SMCs (FIG. 12c-d), consistent with a previous report. In addition, Hb α stabilizing protein in the endothelium of TD arteries and in the VCCC was found (FIG. 13a-b). Taken together, these data show for the first time that arterial ECs express Hb α mRNA and protein and are responsible for enriched Hb α expression at the MEJ.

Figure 2B:
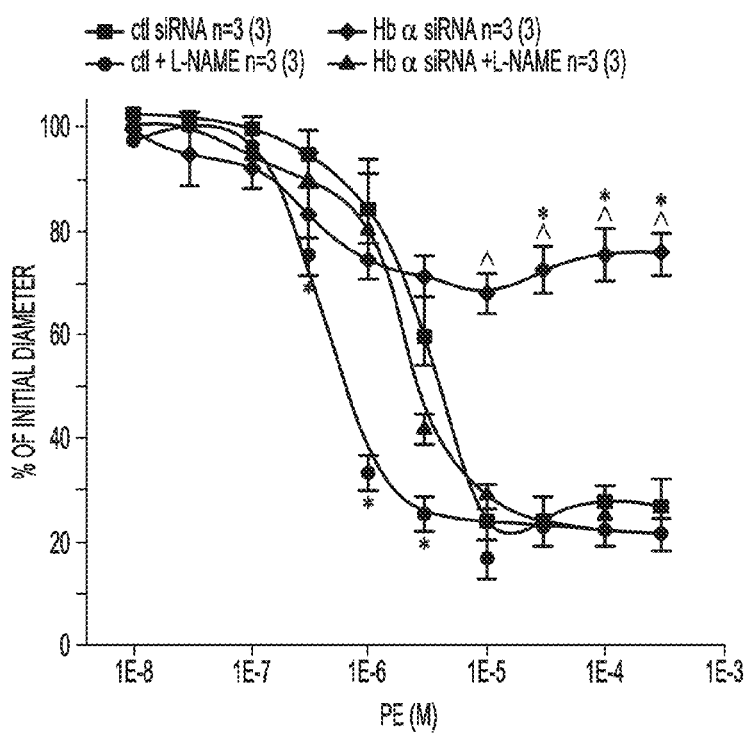
Figure 2C:
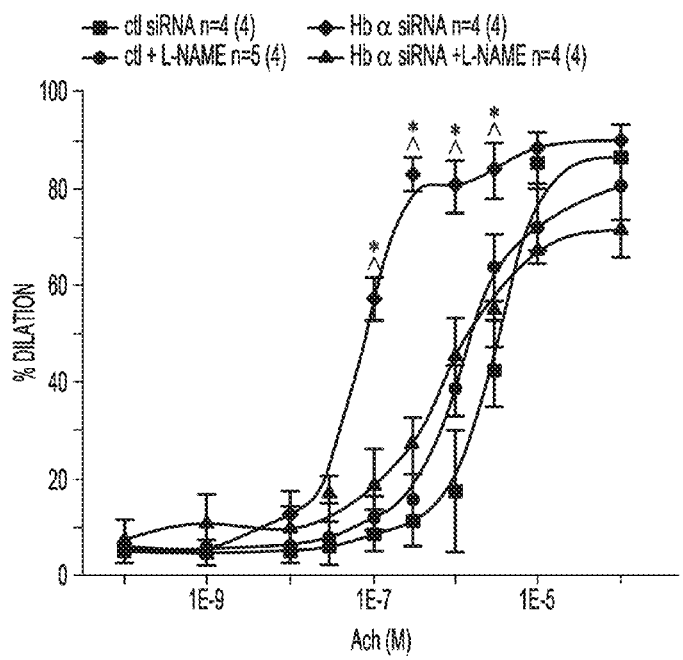
Figure 2D:
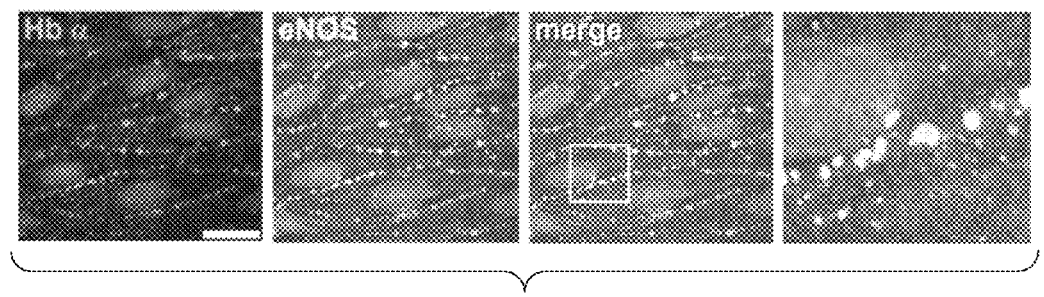
Figure 2E:
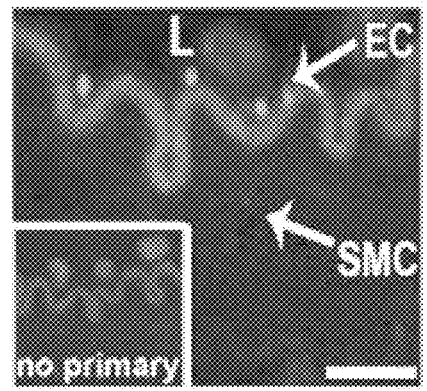
Figure 2F:
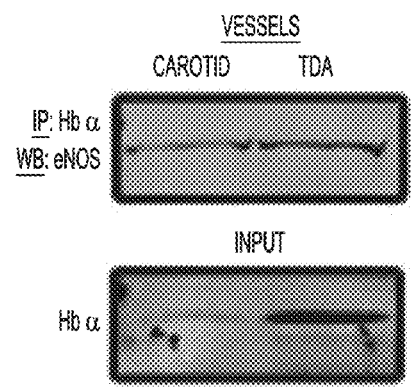
Figure 2G:
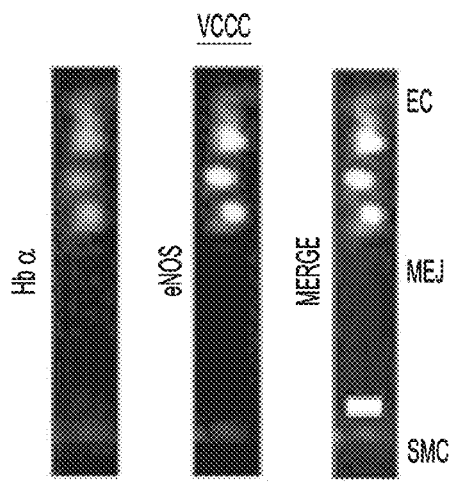
Figure 2H:
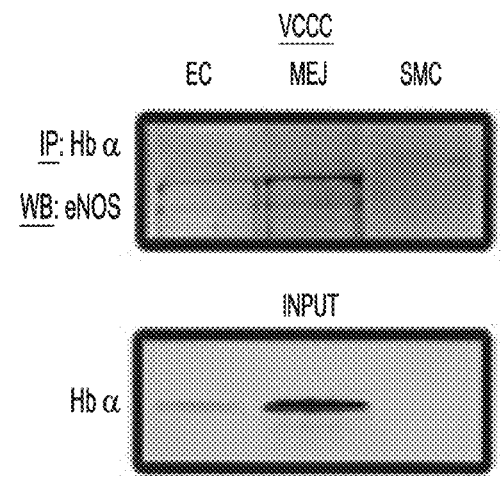
Figure 2I:
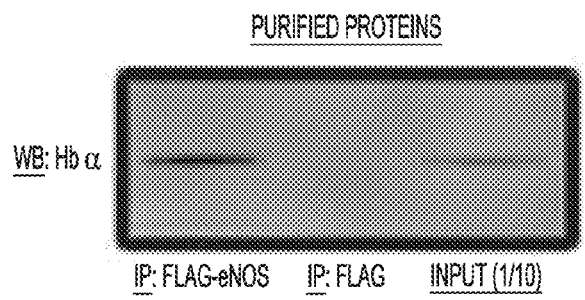
Figure 14:
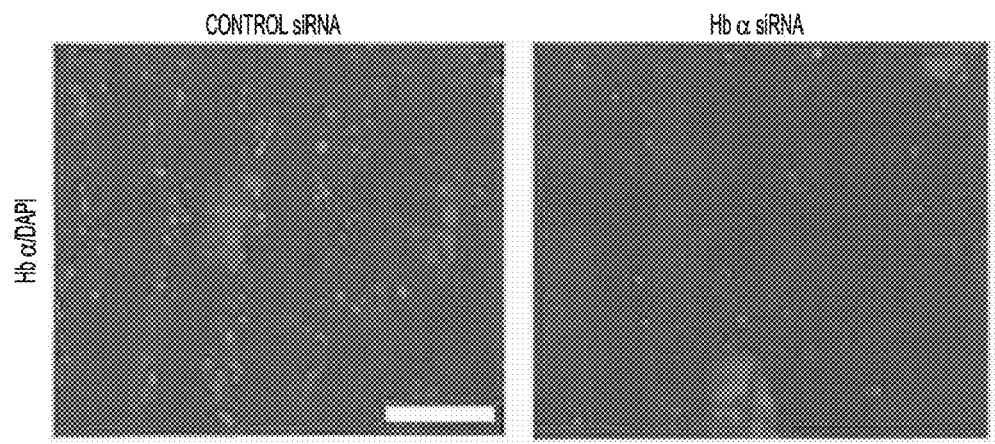
FIG. 14—Expression of HB α followed siRNA knockdown in TD arteries. En face immunofluorescence of Hb α expression following siRNA knockdown in ECs. Red indicates Hb α expression and blue shows labeled nuclei. Scale bar is 10 m.
Figure 15A:
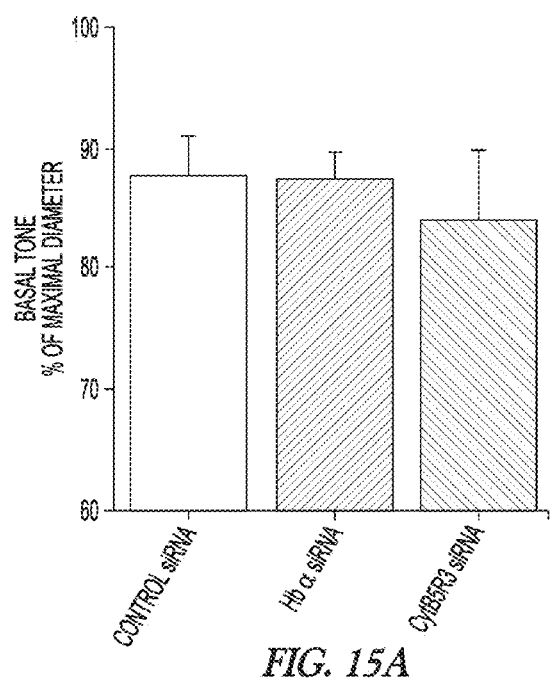
FIG. 15—Effect of basal tone after siRNA transfection or PTU treatment. a, Measurement of basal tone (initial diameter/maximal diameter×100) for arteries transfected with Hb α and CytB5R3 siRNA or b, PTU. $n≥4$.

To investigate the functional role of Hb α in ECs and its effect on eNOS signaling, ECs in isolated TD arteries were transfected with Hb α or control siRNA. Knockdown efficiency was 70-80% (FIG. 14). Loss of Hb α resulted in a dramatic loss in arterial reactivity following PE application in a single or cumulative doses (FIG. 2a-b) and increased reactivity to acetylcholine (Ach) (FIG. 2c), but there was no change in response to 5-hydroxytryptamine (5-HT) (Table 1). $EC_{50}$ and $E_{max}$ values are in Table 2. No difference was observed in basal tone (FIG. 15a). However, with the addition of the NOS inhibitor L-$N^G$-nitroarginine methyl ester (L-NAME), the effect of Hb α siRNA was comparable to control conditions for both PE and Ach responses (FIG. 2a-c). It was thus hypothesized that eNOS, the primary isoform in the vessel wall, may be in close spatial proximity to Hb α. This was investigated using four methods: co-localization studies by immunofluorescence (FIG. 2d,g), a proximity ligation assay (FIG. 2e), and co-immunoprecipitations from cell lysates (FIG. 2f,h) and purified proteins (FIG. 2i). These analyses revealed Hb α and eNOS are in a macromolecular complex and can form a direct protein-protein interaction.

Table 1

TABLE 1

Table 1 - The effect of 5-HT induced contraction on TD arteries with HB α or CYT5BR3 knockdown or PTU pretreatment in the presence or absence of L-NAME.
Contraction to 5-HT 50 nM Post 15 min

|  | % initial diameter |
|---|---|
| Control sirNa | 52.41 ± 7.4 |
| Control sirNa + L-NAME | 48.11 ± 4.69 n.s. |
| Hb α siRNA | 62.19 ± 1.82 n.s. |
| CytB5R3 siRNA | 63.2 ± 3.7 n.s. |

TABLE 1-continued

Table 1 - The effect of 5-HT induced contraction on TD arteries with HB α or CYT5BR3 knockdown or PTU pretreatment in the presence or absence of L-NAME.
Contraction to 5-HT 50 nM Post 15 min

|  | % initial diameter |
|---|---|
| Control | 63.3 ± 6.2 |
| Control + L-NAME | 57.0 ± 3.29 n.s. |
| PTU | 64.1 ± 4.5 n.s. |

Vessels transfected with HB α or CytB5R3 siRNA or pretreated with PTU (50 μM) in the presence or absence of L-NAME were stimulated with 5-HT (50 nm).
The % initial diameter was quantified 15 minutes after stimulation (n = 3).
n.s. indicates not significant.

Table 2

TABLE 2

Table 2 - Pharmacological properties for PE and Ach cumulative concentration response curves (CCRC) after siRNA knockdown with Hb α or CytB5R3 or pretreatment with PTU.

| PE CCRC $EC_{50}$ and $E_{max}$ | | |
|---|---|---|
|  | $EC_{50}$ (μM) | $E_{max}$ (% initial diameter) |
| Control siRNA | 2.577 ± 0.508 | 19.0 ± 2.9 |
| Hba siRNA | 0.196 ± 0.084* | 71.8 ± 4.2* |
| CyB5R3 siRNA | 0.416 ± 0.172* | 68.1 ± 4.0* |
| Control siRNA + L-NAME | 0.426 ± 0.038 | 23.1 ± 2.8 |
| Hba siRNA + L-NAME | 1.885 ± 0.397^ | 22.4 ± 1.9^ |
| CytB5R3 SiRNA + L-NAME | 0.531 ± 0.085 | 26.8 ± 4.0^ |

| Ach CCRC $EC_{50}$ and $E_{max}$ | | |
|---|---|---|
|  | $EC_{50}$ (μM) | $E_{max}$ (% Dilation) |
| Control siRNA | 2.7274 ± 0.496 | 88.6 ± 5.0 |
| Hba siRNA | 0.077 ± 0.010* | 86.8 ± 4.2 |
| CyB5R3 siRNA | 0.355 ± 0.235* | 93.9 ± 10.6 |
| Control siRNA + L-NAME | 1.185 ± 0.389 | 80.7 ± 6.3 |
| Hba siRNA + L-NAME | 0.882 ± 0.305 | 76.7 ± 2.7 |
| CytB5R3 SiRNA + L-NAME | 1.469 ± 0.282 | 83.7 ± 1.6 |

| PE CCRC $EC_{50}$ and $E_{max}$ | | |
|---|---|---|
|  | $EC_{50}$ (μM) | $E_{max}$ (% initial diameter) |
| Control | 1.206 ± 0.357 | 60.6 ± 1.9 |
| PTU | 6.623 ± 4.697 | 91.4 ± 2.5# |
| L-NAME | 1.534 ± 0.357 | 62.6 ± 6.1 |
| PTU + L-NAME | 0.454 ± 0.148 | 60.4 ± 7.8♦ |

| Ach CCRC $EC_{50}$ and $E_{max}$ | | |
|---|---|---|
|  | $EC_{50}$ (μM) | $E_{max}$ (% Dilation) |
| Control | 33.7 ± 6.4 | 97.4 ± 2.5 |
| PTU | 21.9 ± 7.7 | 94.9 ± 1.7 |

The left column represents each condition, the middle column shows the 50% of maximal effective concentration (($EC_{50}$)-in μM) for both PE and Ach and the right column indicates the maximum effective concentration ($E_{max}$) expressed as the % of initial diameter for PE and % dilation for Ach.
*indicates significance between control siRNA vs. Hb α/CytB5R3 siRNA and ^ shows significance between control siRNA vs. Hb α + L-NAME/CytB5R3 + L-AME siRNA for both $EC_{50}$ and $E_{max}$.
indicates significance between control vs. PTU and black diamond shows significance between PTU vs. PTU + L-NAME.

Figure 2J:
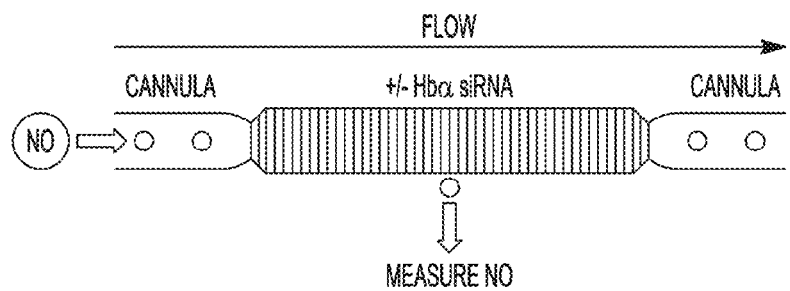

Without wishing to be bound by any particular theory, it is hypothesized herein that Hb α likely interacts with eNOS to regulate blood vessel tone by controlling NO diffusion through its scavenging by heme iron. The mechanism of interaction by measuring loss of NO radical in TD and carotid arteries, and in the VCCC model was studied. NO was lost in TD arteries, but not carotid arteries; and it was lost in MEJ fractions—but not EC or SMC—lysates (FIG. 16a-b). Next, endothelial Hb α in isolated arteries (FIG. 2j) or VCCCs (FIG. 2l) was knocked down using siRNA. Loss of Hb α increased NO diffusion across the vessel wall (FIG. 2k) and in the VCCC (FIG. 2m). Together, these results indicate that endothelial Hb α can regulate arterial tone through its effects on NO diffusion.

Figure 3:
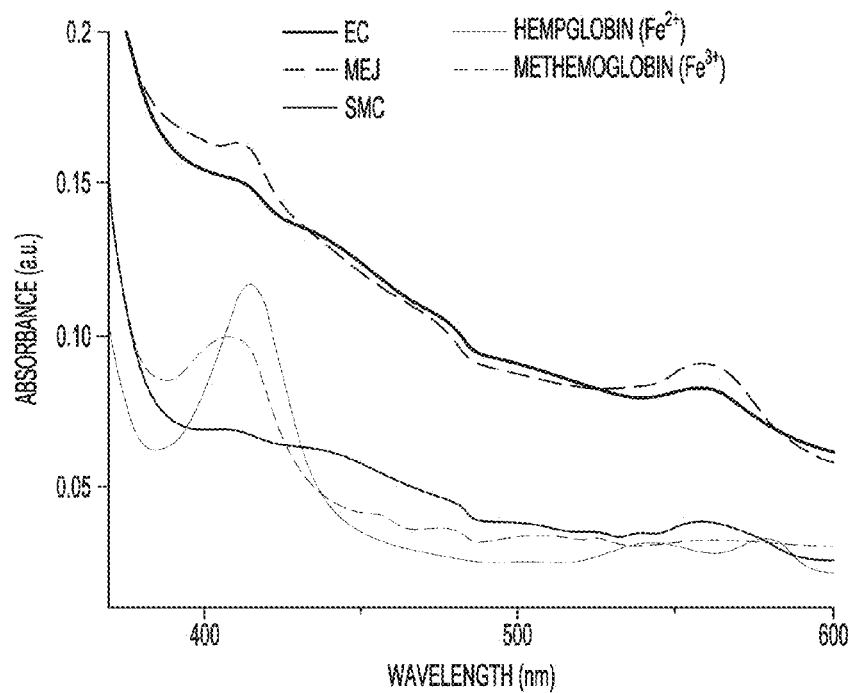
FIG. 3—The oxidation state of Hb α resides in a mixture of $Fe^{2+}$ and $Fe^{3+}$. a, Ultraviolet-visible spectroscopy analysis of TD arteries and c VCCC fractions. The inset in a indicates the region of interest (magenta box) of the Soret (~420 nm) and Q bands (~540-575 nm). b, measurement of Hb α oxidation state calculating the ratio of $Fe^{2+}$ to $Fe^{3+}$ in TD arteries (n=3) and d VCCC fractions (n=3) with and without Hb α siRNA. When MEJ fractions were studied, a Soret peak (~410 nm) characteristic of the $Fe^{3+}$ state (methemoglobin) was found (FIG. 3c). In b striped bars indicate ex vivo data and in d open bars represent in vitro data. p values are indicated for each comparison. All error bars represent s.e.m.
Figure 3D:
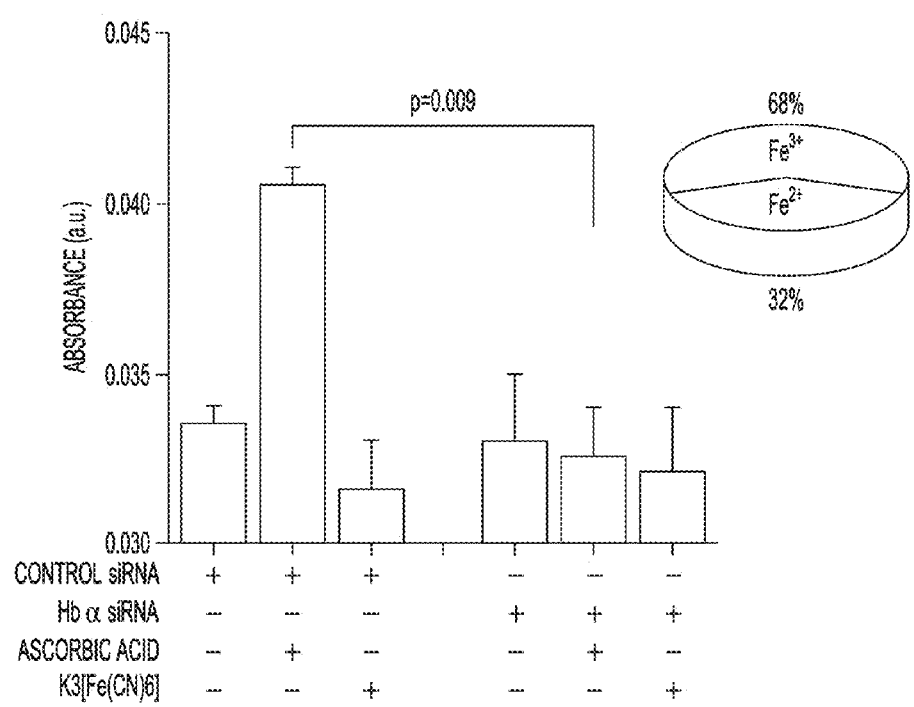
Figure 3A:
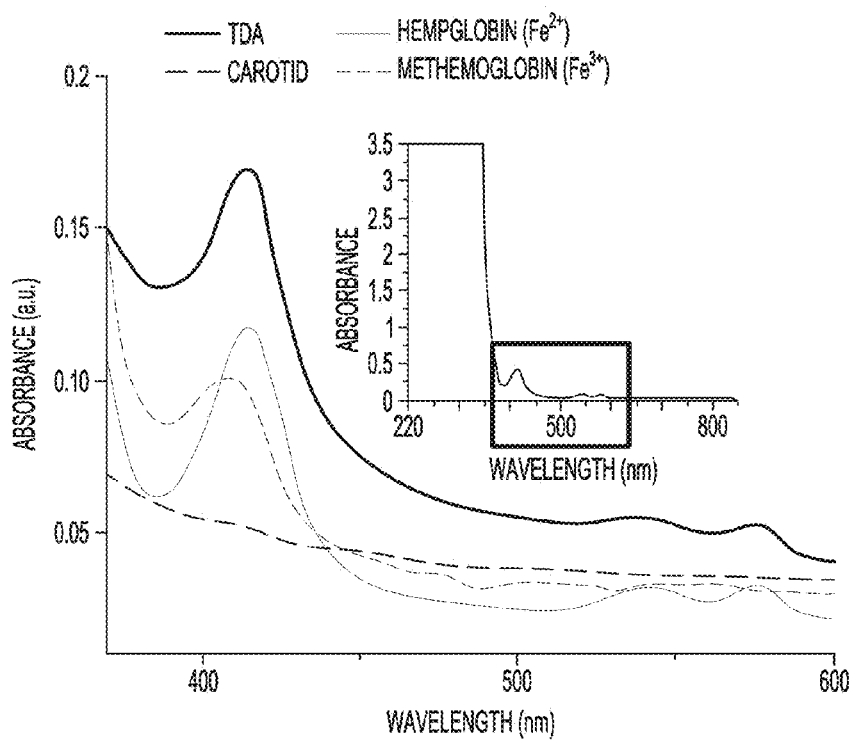
Figure 3B:
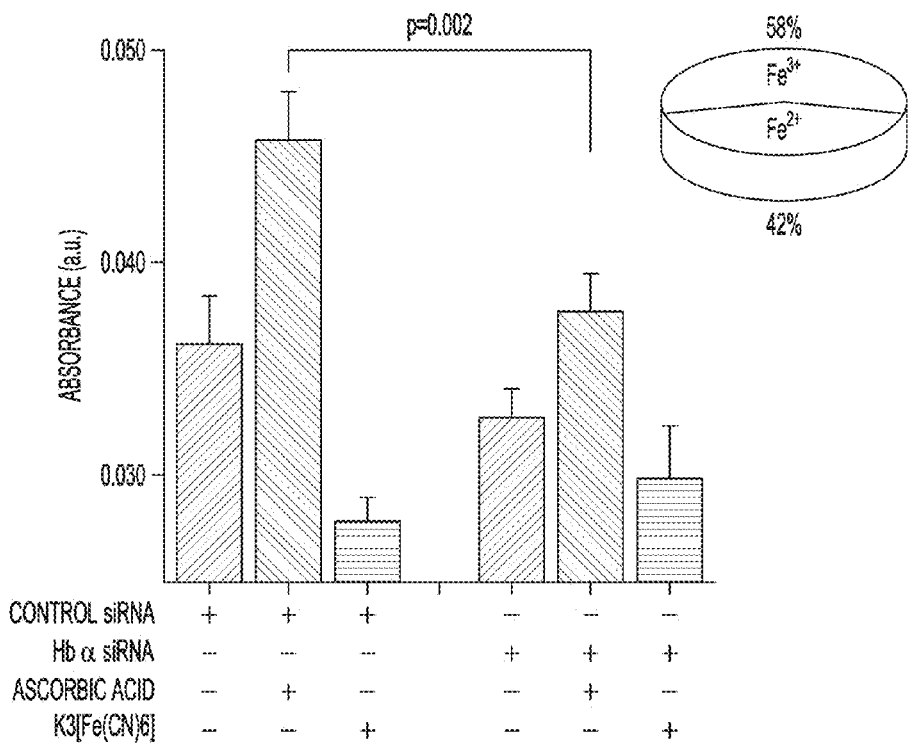
Figure 16D:
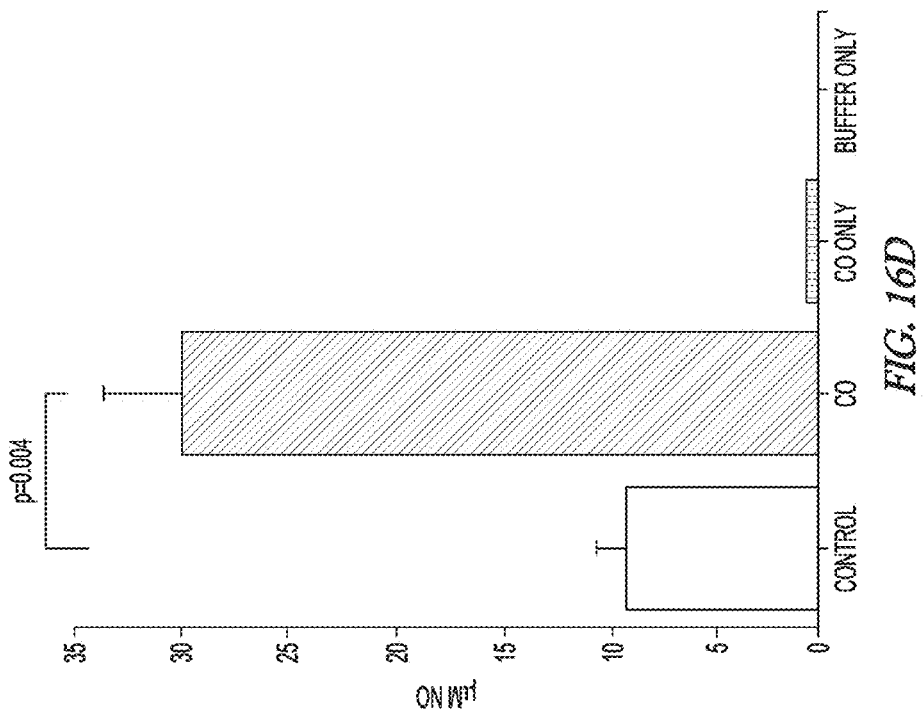
FIG. 16—NO is primarily consumed in TD arteries and MEJ lysates and NO diffusion is inhibited with CO. Measurement of NO consumption from isolated carotid or TD arteries (16A1 and 16A2) or EC MEJ, or SMCs lysates (16B1 and 16B2) ($n≥3$). The tracings in 16A1 and 16B1 show the differences in NO consumption measured by Seivers NO analyzer and 16A2 and 16B2 depict NO diffusion. 16C, NO diffusion in mouse TD arteries ($n≥3$) or 16D, VCCCs ($n=5$) that were pretreated with carbon monoxide. In 16A2 and 16C, striped bars represent ex vivo data an in 16B2 and 16D open bars indicate in vitro data. p values are indicated for each comparison. All error bars represent s.e.m.
Figure 16C:
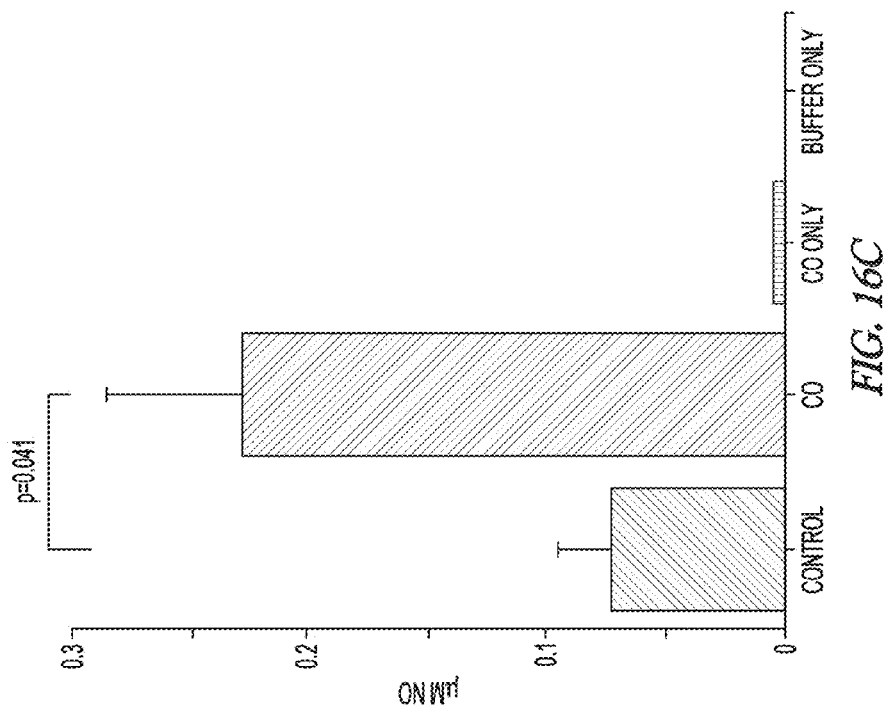
Figure 17:
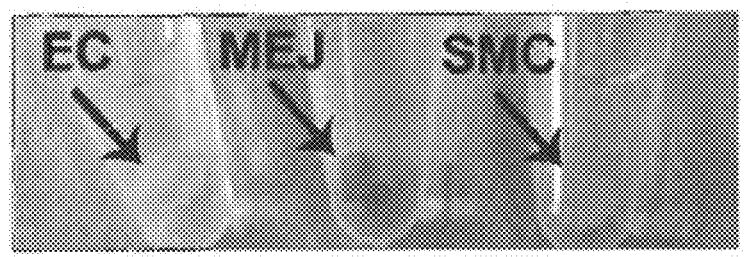
FIG. 17—Membrane precipitates from VCCC fractions. Image of membrane proteins showing a brown pellet characteristic of methemoglobin in the MEJ lysate.

Next, it was hypothesized that Hb α heme iron in the oxygenated $Fe^{2+}$ state should control NO diffusion through a fast reaction ($2.4 \times 10^7$ $M^{-1} \cdot sec-1$) resulting in dioxygenation, whereas $Fe^{3+}$ state should permit NO diffusion due to a slower reaction rate ($3.3 \times 10^3 M-1 \cdot sec^{-1}$). It was found that Hb α heme iron resides in both states. First, using UV-visible spectroscopy, a Soret peak (~420 nm) and Q bands (~540-575 nm) in isolated TD arteries was identified consistent with oxygen bound Hb $Fe^{2+}$, whereas there was no peak in carotid arteries (FIG. 3a). Next, the oxidation state of Fe was measured and found approximately 42% existed in the $Fe^{2+}$ and 58% in the $Fe^{3+}$ state (FIG. 3b). These measurements were sensitive to Hb α siRNA (FIG. 3b). Consistent with this observation, it was found that carbon monoxide (CO) ligated $Fe^{2+}$ heme, resulted in increased NO diffusion across isolated vessels (FIG. 16c). When MEJ fractions were studied, a Soret peak (~410 nm) characteristic of the $Fe^{3+}$ state (methemoglobin) was found (FIG. 3c). Interestingly, pelleted membranes from MEJ fractions were dark brown, consistent with $Fe^{3+}$ oxidation (FIG. 17). It was also found approximately 32% of Fe existed in the $Fe^{2+}$ and 68% in the $Fe^{3+}$ state (FIG. 3d), results that were also sensitive to Hb α siRNA (FIG. 3d). An increase in NO diffusion in VCCCs treated with CO was also observed (FIG. 16d).

Figure 18A:
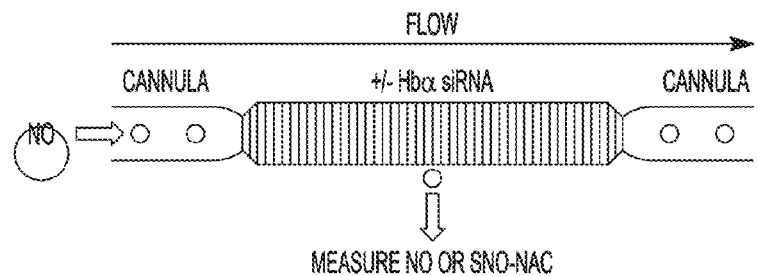
FIG. 18—Decreased Hb α expression in TD arteries or in the VCCC results in decreased S-nitrosothiol formation. a, Schematic diagram of experimental design illustrating a cannulated vessel with transfected HB α si RNA showing S-nitrosothiol formation as a readout. b, Effect of Hb α expression on S-nitrosothiol synthesis in isolated TD arteries (n=3). c, Illustration of experimental setup for VCCC experiments. d, Measure of S-nitrosothiol generation in the VCCC following knockdown of HB α (n=4). In b and d n.s. indicates not significant. p values are shown for each composition. All error bars represent s.e.m.
Figure 18B:
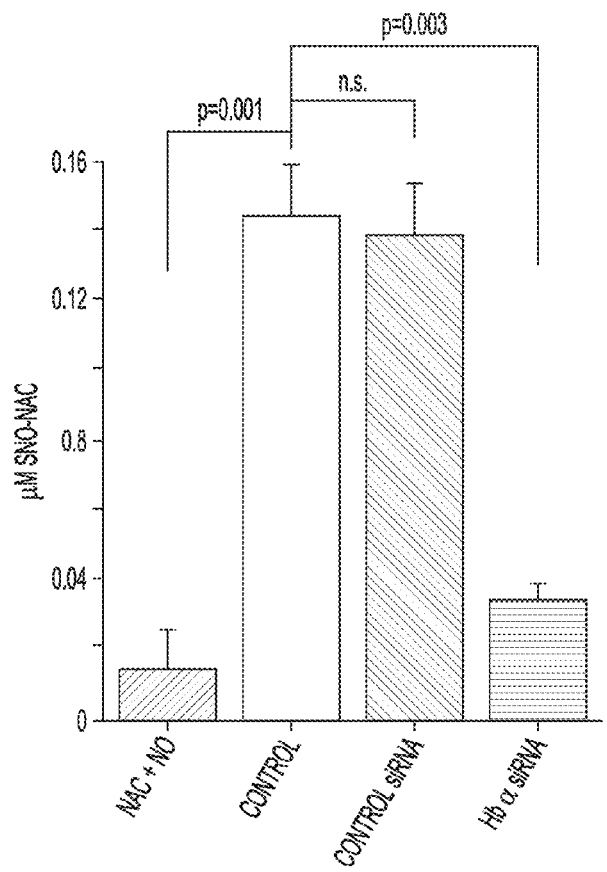
Figure 18C:
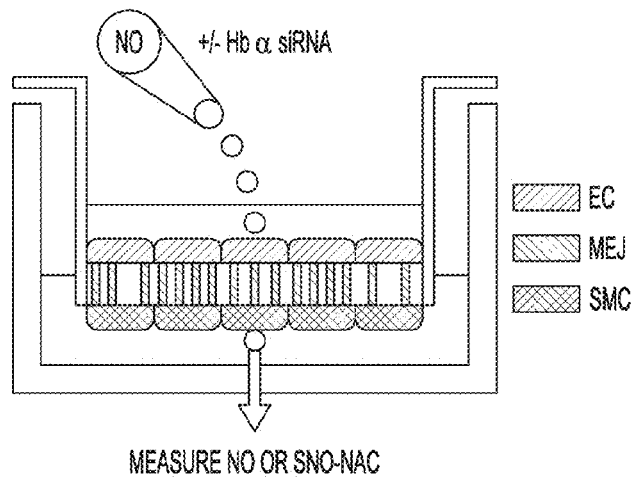
Figure 18D:
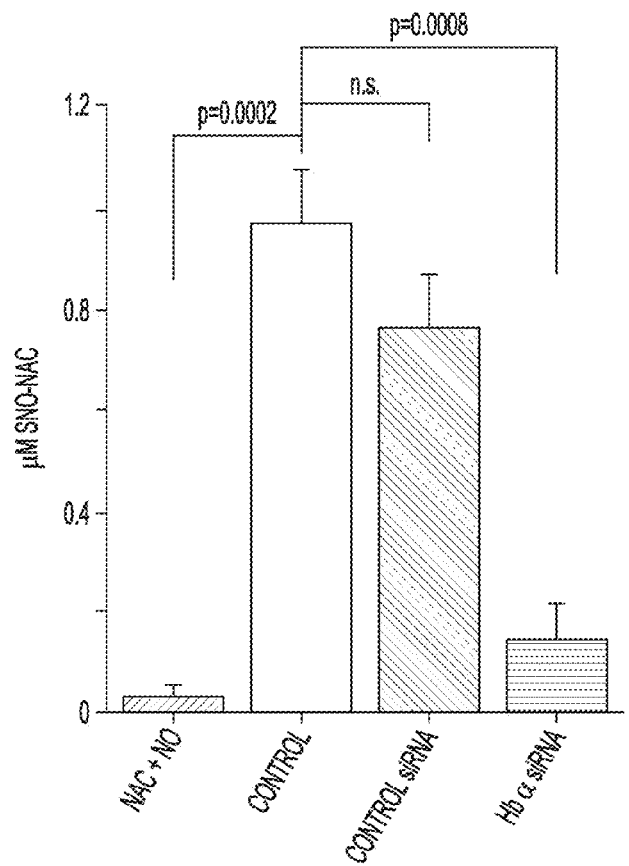

Previous work has demonstrated that NO-heme $Fe^{3+}$ interaction results in reductive nitrosylation, a mechanism known to generate S-nitrosothiols, which has been shown to have a role in gap junction regulation at the MEJ. Using N-acetylcysteine as a bait reactant on the abluminal side (FIG. 18a,c), a striking loss of S-nitrosothiol synthesis after Hb α knock down in TD arteries (FIG. 18b) and in the VCCC was found (FIG. 18d). Together, these results suggest that Hb α heme oxidation state regulates both NO diffusion and bioactivation.

Figure 4I:
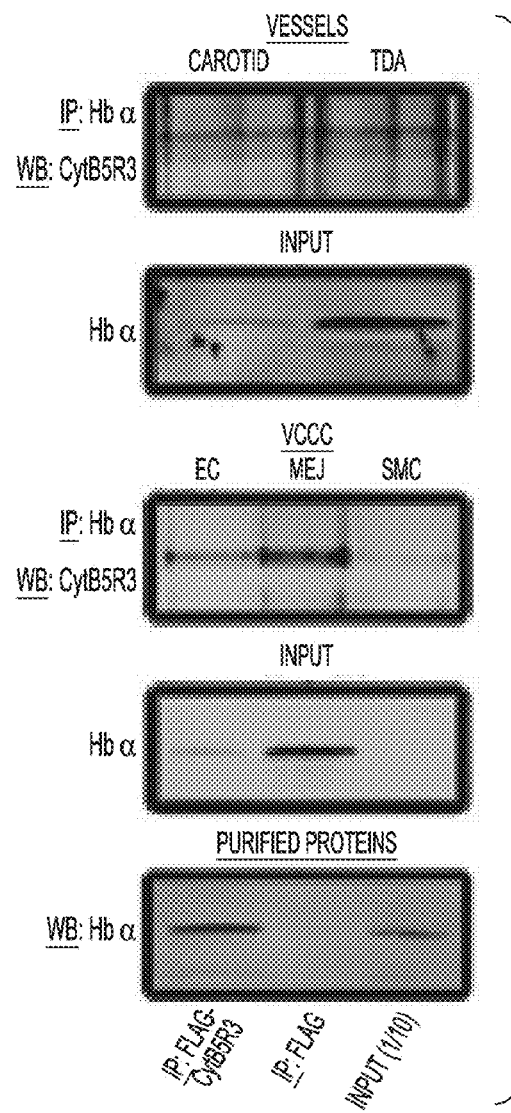
Figure 4J:
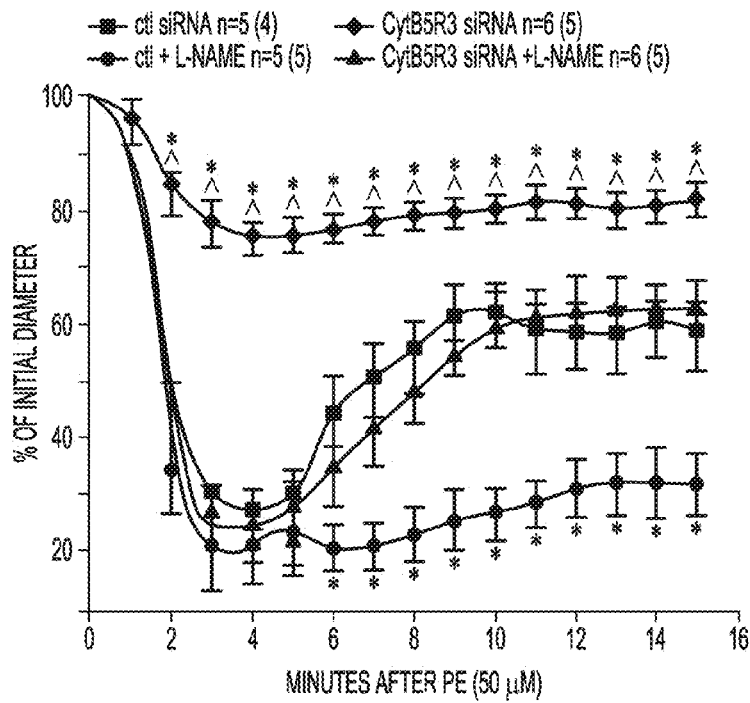
Figure 4K:
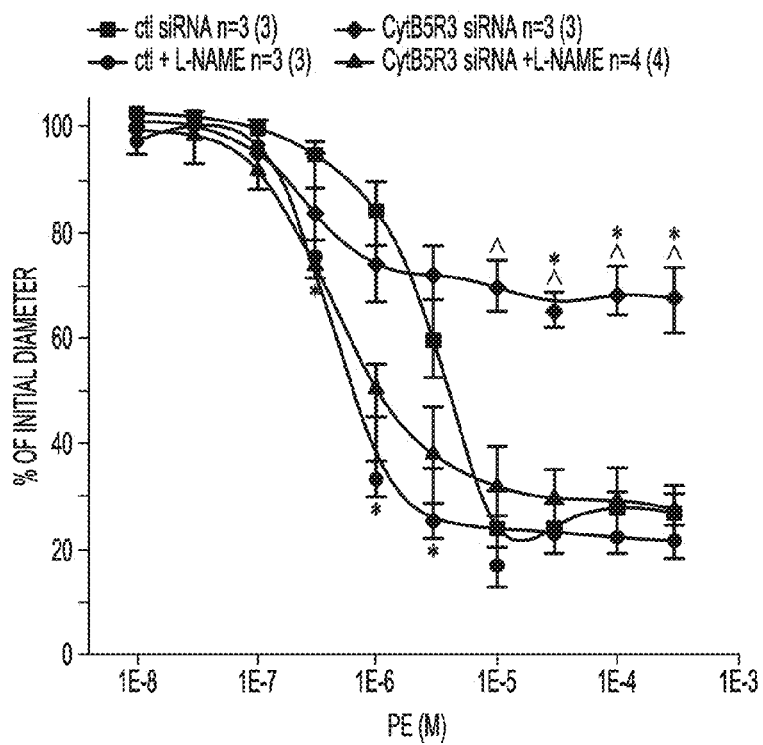
Figure 4L:
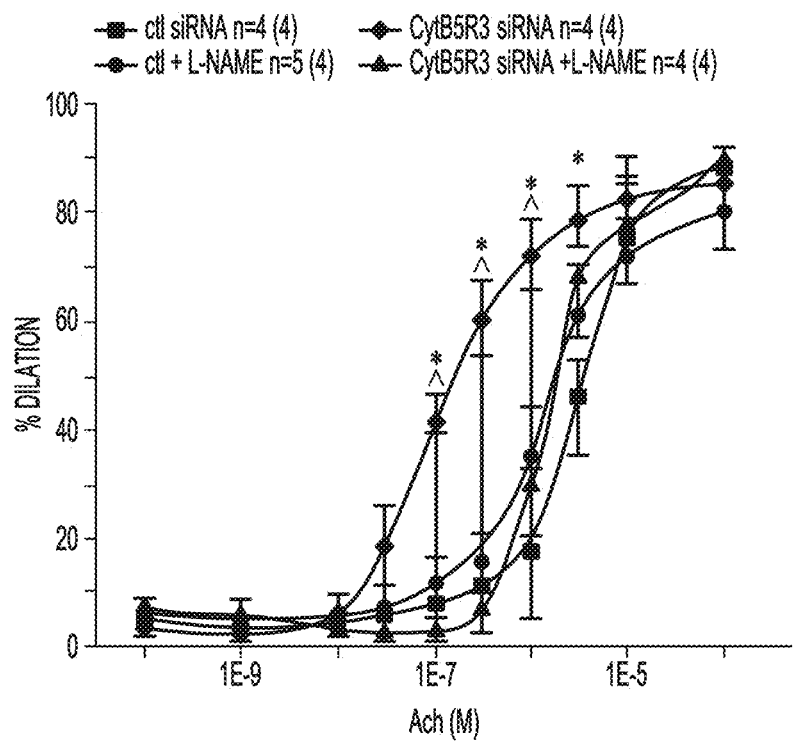
Figure 4M:
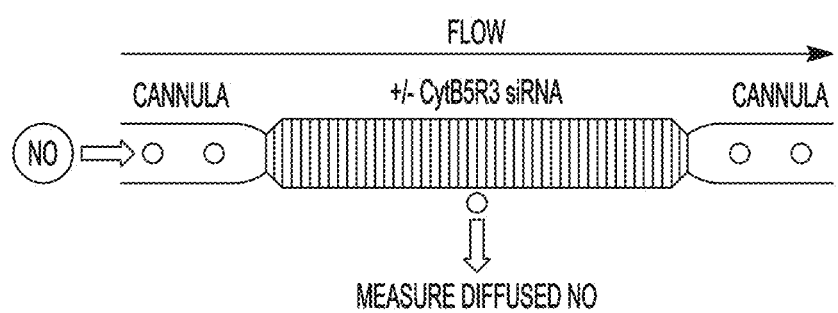
Figure 4P:
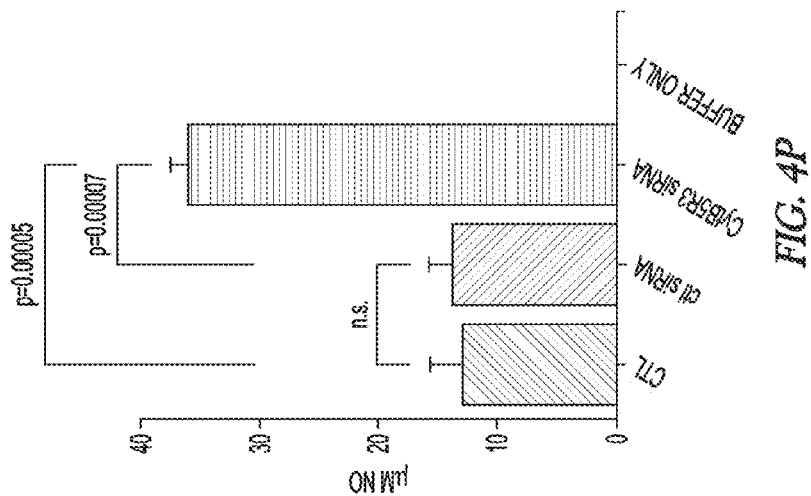
Figure 4O:
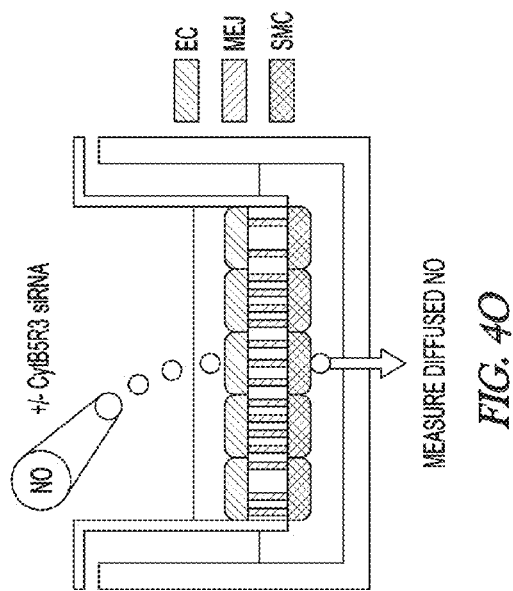
Figure 4N:
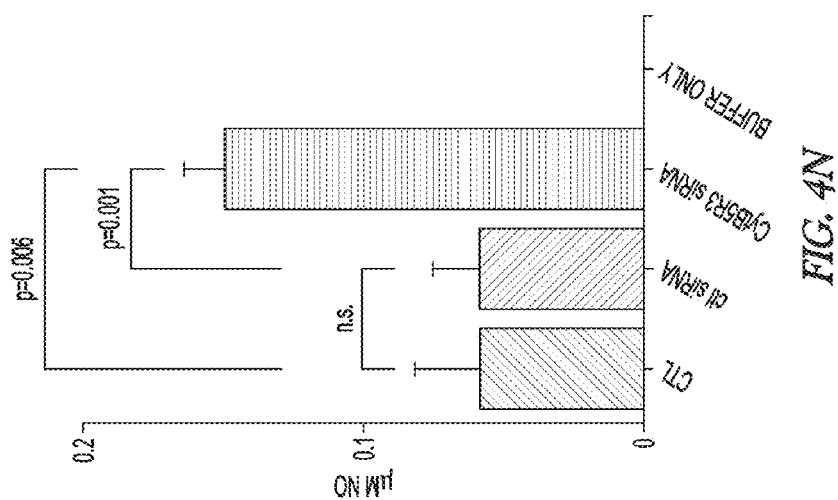
Figure 5A:
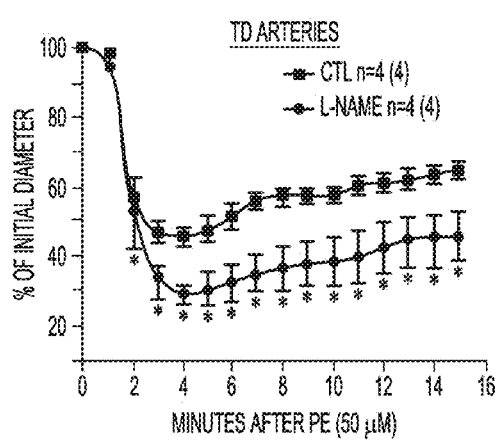
FIG. 5—NO diffusion is limited following PE stimulation. a, Vascular reactivity of TD arteries in the presence or absence of the NOS inhibitor L-NAME following 50 µM PE stimulation. n indicates the number of arteries; value in parenthesis shows number of mice. * represents significant differences of $p<0.05$. b, Measurement of cGMP accumulation after PE application in SMCs of VCCC in the presence or absence of L-NAME ($n≥4$). c-d, Time course for cGMP accumulation following PE stimulation ($n=4$). e, Schematic illustration showing PE application to TD arteries or f SMCs in a VCCC followed by f, measurements of NO release ($NO_x$). g, Time course evaluation of $NO_x$ accumulation in the extracellular milieu of TD arteries or h VCCCs following PE stimulation. In b, c, g, and h n.s. means not significant. In b, d and h open bars represent in vitro data and in c, g, striped bars indicate ex vivo data. P values are shown for each comparison. All error bars represent s.e.m.
Figure 5B:
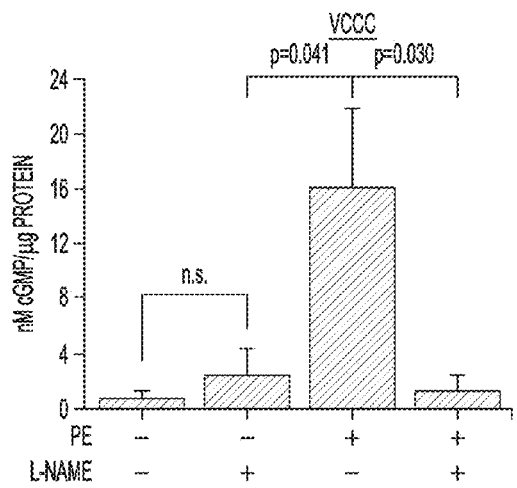
Figure 5C:
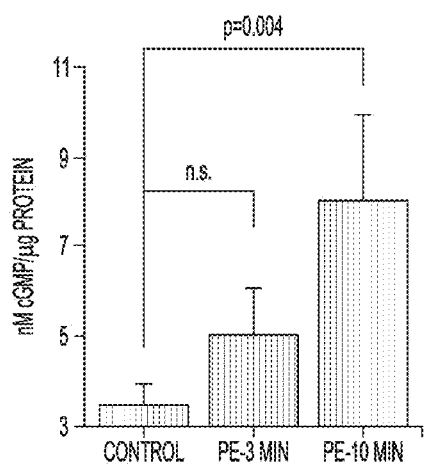
Figure 5D:
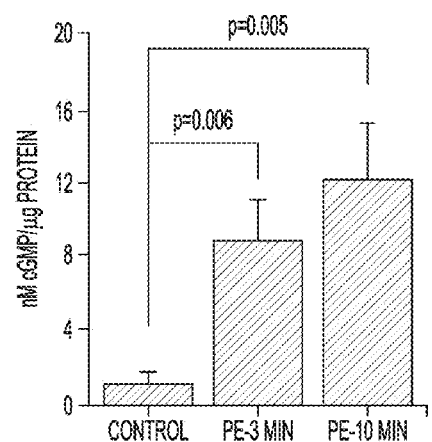
Figure 5E:
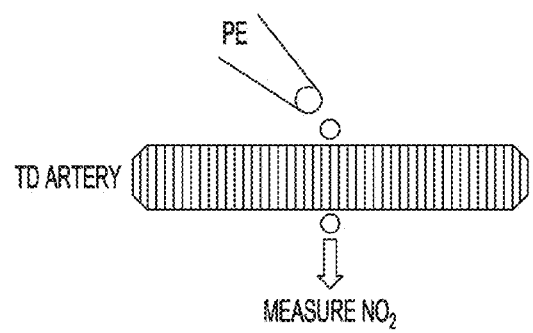
Figure 5F:
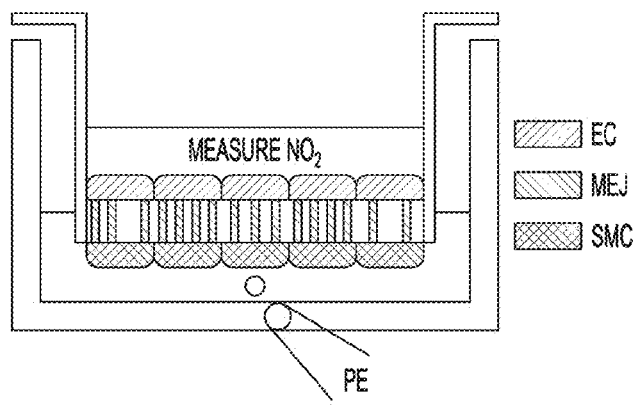
Figure 5G:
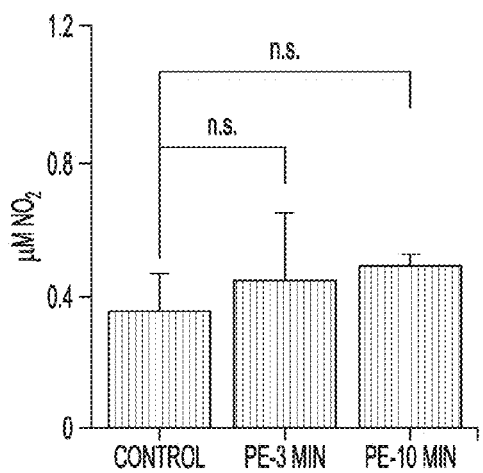
Figure 5H:
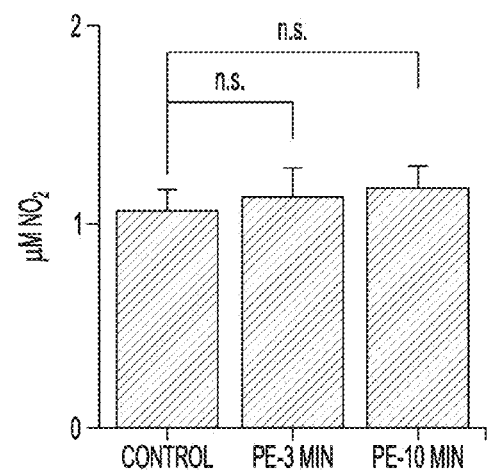
Figure 15B:
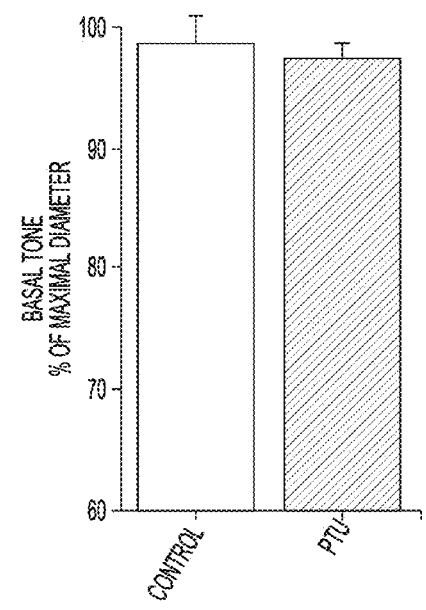
Figure 22A:
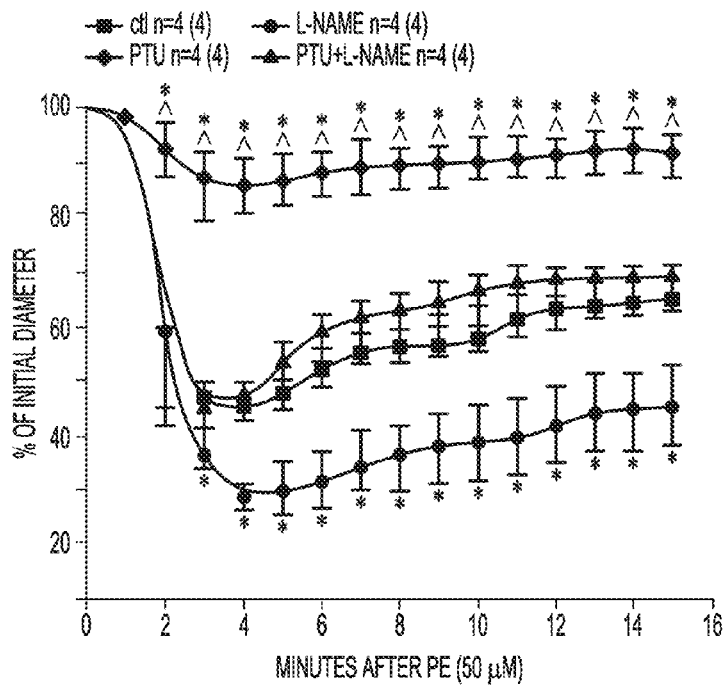
FIG. 22—Inhibited activity of CytB5R3 with PTU alters vascular reactivity and NO diffusion. a, Time course to PE, b dose response to PE or c dose response to ACH on TD arteries treated with control or PTU in the presence or absence of L-NAME. n indicates the number of arteries; value in parenthesis shows number of mice. The inset graph in b represents TD arteries treat with control, PTU or L-thyroxin (50 µM)+PTU followed by stimulation with 10 µM PE (n=4). d, Schematic diagram of experimental design illustrating a cannulated vessel treated with PTU showing NO diffusion as a readout. e, NO diffusion results from mouse TD arteries treated with PTU (n=4). f, Illustration of experimental setup for VCCC experiments with PTU. g, NO diffusion results from VCCCs incubated with PTU. (n≥3). In e striped bars represent ex vivo data and in m open bars indicate in vitro data. In a and b * shows significance between control vs. PTU, ˆ indicates significance between PTU vs. PTU+L-NAME and black diamond represents significance between control vs. L-NAME. p values are shown for each comparison. All error bars represent s.e.m.
Figure 22B:
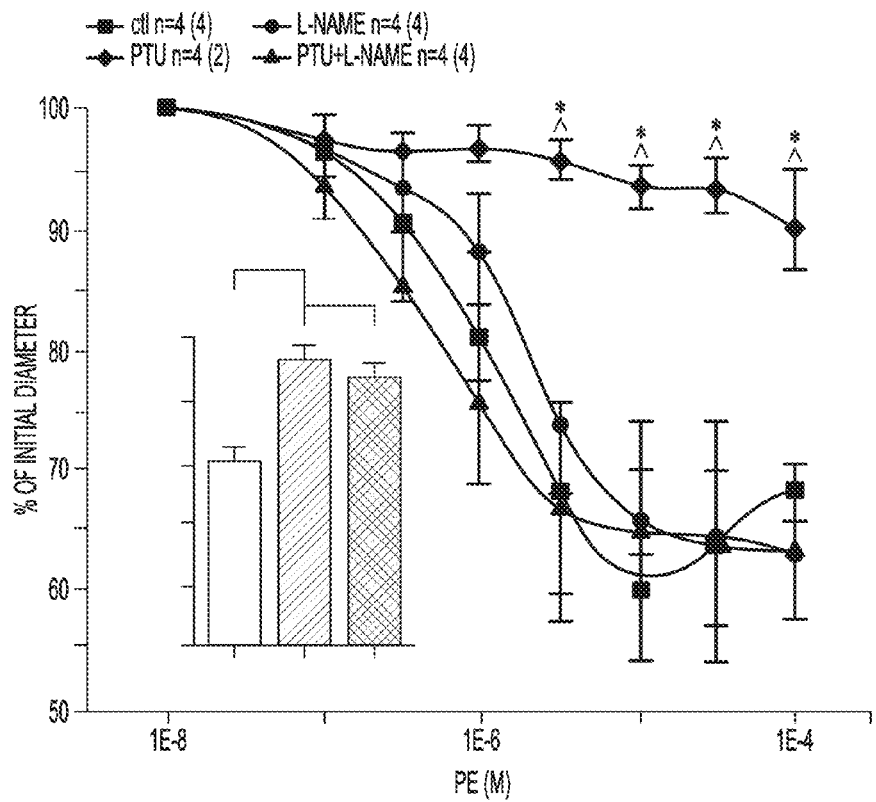
Figure 22C:
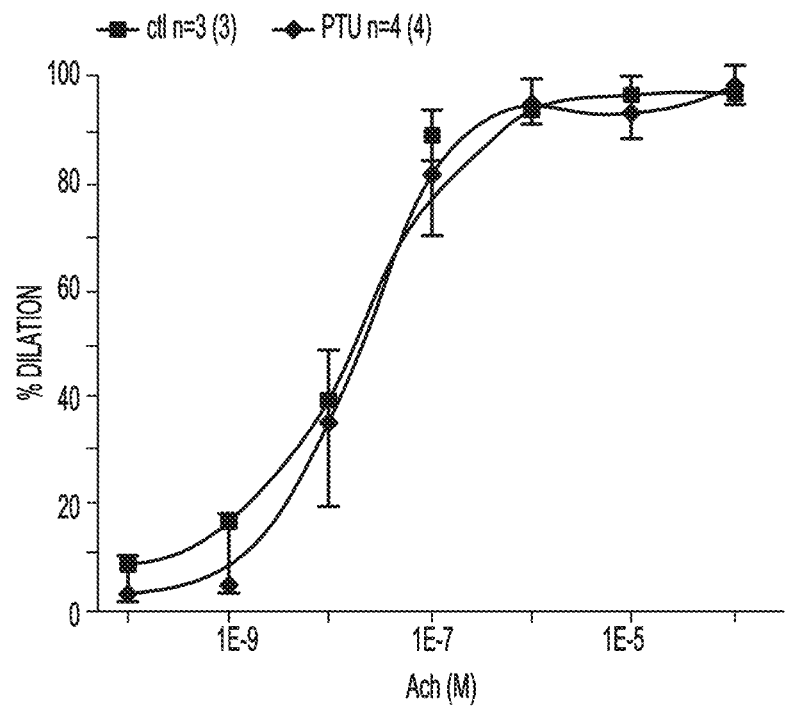
Figure 22D:
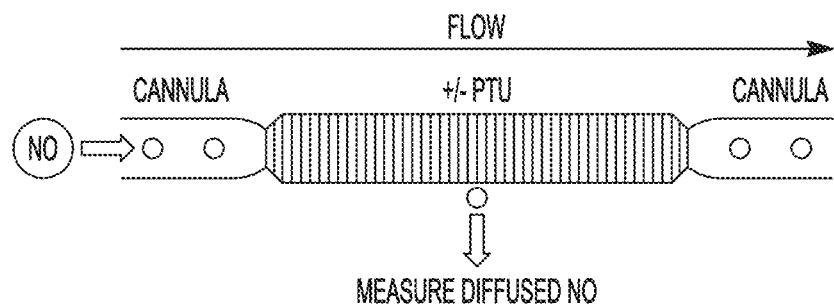

Next the mechanism regulating Hb α oxidation state was investigated. In erythrocytes, cytochrome B5 reductase 3 (CytB5R3) or diaphorase 1, a known methemoglobin reductase, controls the heme iron oxidation state through reduction of $Fe^{3+6}$. Using immunofluorescence (in vivo FIG. 4a, in vitro FIG. 4e), TEM (FIG. 4b), and Western blot analysis (in vivo FIG. 4c, in vitro 4d), it was identified that CytB5R3 was expressed in ECs and at the MEJ. In addition, it was established that CytB5R3 is in a complex with Hb α using four separate assays: immunofluorescence (FIG. 4f-g), proximity ligation assay (FIG. 4h), and co-immunoprecipitation from cell lysates and purified proteins (FIG. 4i). Indeed, molecular modeling of the crystal structures for Hb α, eNOS, and CytB5R3 revealed a discreet region of high probability where the proteins could interact (FIG. 19). Next, CytB5R3 siRNA (knockdown efficiency: ~50%, FIG. 20a) and overexpression was used to show that CytB5R3 regulates metHb α reduction. Time lapse UV-visible spectrometry demonstrated that loss of CytB5R3 inhibited metHb α reduction and that overexpression enhanced metHb α reduction (FIG. 20b-c). To determine if CytB5R3 expression or activity regulates arterial tone, both siRNA directed against endothelial CytB5R3 in TD arteries and a pharmacological inhibitor of CytB5R3, propylthiouracil (PTU) were tested. Knockdown efficiency was about 70% (FIG. 21a). A decrease in arterial reactivity in TD arteries transfected with CytB5R3 siRNA after PE stimulation with a single dose or cumulative concentrations (FIG. 4*j-k*) and increased reactivity with ACh dose response was observed (FIG. 4*l*). Vascular reactivity to PE or Ach in TD arteries pretreated with PTU is shown in (FIG. 22*a-c*). The effect with PTU was not reversible with L-thyroxine supplementation after PE stimulation (FIG. 22*b*, inset). However, no change was found with 5-HT (Table 1). $EC_{50}$ and $E_{max}$ values are in Table 2. However, with the addition of L-NAME, the effect of CytB5R3 siRNA was comparable to control conditions (FIG. 4*j-l*) or PTU treated arteries (FIG. 22*a-b*), results that were consistent with Hb α knockdown. No difference in basal tone for CytB5R3 siRNA or PTU was found (FIG. 15*a-b*). Next the effect of CytB5R3 on NO diffusion in vessels and VCCC was investigated (FIG. 4*m,o*). Knockdown of CytB5R3 siRNA was ~30% at the MEJ (FIG. 21*b*) and in the EC monolayer but not in SMCs (FIG. 21*c*). Both CytB5R3 siRNA and PTU treatment increased NO diffusion across both isolated vessels and in VCCC (FIG. 4*n, p*; FIG. 22*d-g*). Note that CytB5R3 knockdown did not alter MEJ eNOS or Hb α expression (FIG. 21*d*).

It is concluded that EC expression of Hb α plays a role in the regulation of NOS-mediated signaling and in the control of arterial vascular reactivity. These results have far reaching implications that can influence many aspects of vascular biology and disease. For example, endothelial Hb α expression may participate in blood pressure control, arteriogenesis and anti-inflammatory signaling, as well as impact other redox signaling molecules (e.g. superoxide and hydrogen peroxide). The present invention therefore encompasses methods for regulating these processes using the compositions and method of the invention. Indeed, the results disclosed herein correlate with diagnostic indices for human alpha thalassemia major (Hb $\alpha^{-/-\ -/-}$) fetuses, who show increased cerebral blood flow during development. Furthermore, these observations can explain why inhibition of CytB5R3 attenuates hypertension. Taken together, these data provide evidence for a novel paradigm in which somatic cell Hb oxidation is required for NO-dependent bioactivity.

BIBLIOGRAPHY

1. Lim, K. H., et al. Nature 452, 646-649, doi:nature06778 [pii] 10.1038/nature06778 (2008).
2. Hess, D. T., et al. Nat Rev Mol Cell Biol 6, 150-166, doi:nrm1569 [pii] 10.1038/nrm1569 (2005).
3. Bolotina, V. M., et al. Nature 368, 850-853, doi:10.1038/368850a0 (1994).
4. Shesely, E. G. et al. Proc Natl Acad Sci USA 93, 13176-13181 (1996).
5. Straub, A. C. et al. Arterioscler Thromb Vasc Biol 31, 399-407, doi:ATVBAHA.110.215939 [pii] 10.1161/ATVBAHA.110.215939 (2011).
6. Hultquist, D. E. & Passon, P. G. Nat New Biol 229, 252-254 (1971).
7. Newton, D. A., et al. J Biol Chem 281, 5668-5676, doi:M509314200 [pii] 10.1074/jbc.M509314200 (2006).
8. Nishi, H. et al. J Am Soc Nephrol 19, 1500-1508, doi:ASN.2007101085 [pii]10.1681/ASN.2007101085 (2008).
9. Liu, L., et al. Proc Natl Acad Sci USA 96, 6643-6647 (1999).
10. Schelshorn, D. W. et al. J Cereb Blood Flow Metab 29, 585-595, doi:jcbfm2008152 [pii] 10.1038/jcbfm.2008.152 (2009).
11. Halligan, K. E., et al. J Biol Chem 284, 8539-8547, doi:M808231200 [pii] 10.1074/jbc.M808231200 (2009).
12. Brunori, M. et al. Proc Natl Acad Sci USA 102, 8483-8488, doi:0408766102 [pii]10.1073/pnas.0408766102 (2005).
13. Flogel, U., et al. Proc Natl Acad Sci USA 98, 735-740, doi:10.1073/pnas.011460298 011460298 [pii] (2001).
14. Dora, K. A., et al. Proceedings of the National Academy of Sciences of the United States of America 94, 6529-6534 (1997).
15. Angelo, M., et al. Methods Enzymol 436, 131-168, doi:S0076-6879(08)36008-X [pii] 10.1016/S0076-6879(08)36008-X (2008).
16. Gladwin, M. T., et al. Nat Med 9, 496-500, doi:10.1038/nm0503-496 nm0503-496 [pii] (2003).
17. Palmer, R. M., et al. Nature 327, 524-526, doi:10.1038/327524a0 (1987).
18. Ignarro, L. J., et al. J Biol Chem 261, 4997-5002 (1986).
19. Ignarro, L. J., et al. Circ Res 61, 866-879 (1987).
20. Cassoly, R. & Gibson, Q. J Mol Biol 91, 301-313 (1975).
21. Doyle, M. P. & Hoekstra, J. W. J Inorg Biochem 14, 351-358, doi:50162-0134(00)80291-3 [pii] (1981).
22. Eich, R. F. et al. Biochemistry 35, 6976-6983, doi:10.1021/bi960442g bi960442g [pii] (1996).
23. Sharma, V. S., et al. Biochemistry 26, 3837-3843 (1987).
24. Tejero, J. et al. J Biol Chem, doi:M111.298927 [pii] 10.1074/jbc.M111.298927 (2012).
25. Angelo, M., et al. Proc Natl Acad Sci USA 103, 8366-8371, doi:0600942103 [pii]10.1073/pnas.0600942103 (2006).
26. Lee, E. & Kariya, K. FEBS Lett 209, 49-51, doi:0014-5793(86)81082-1 [pii] (1986).
27. Lam, Y. H. & Tang, M. H. Prenat Diagn 22, 56-58, doi:10.1002/pd.237 [pii] (2002).
28. Fregly, M. J. & Hood, C. I. Circ Res 7, 486-496 (1959).
29. Heberlein, K. R. et al. Circ Res 106, 1092-1102, doi:CIRCRESAHA.109.215723 [pii]10.1161/CIRCRESAHA.109.215723 (2010).
30. Davalos, A. et al. Mol Cell Proteomics 9, 2109-2124, doi:M110.001289 [pii] 10.1074/mcp.M110.001289 (2010).
1 Billaud, M. et al. *Circ Res* 109, 80-85, doi:CIRCRESAHA.110.237594 [pii] 10.1161/CIRCRESAHA.110.237594 (2011).
2 Isakson, B. E. & Duling, B. R. *Circ Res* 97, 44-51 (2005).
3 Heberlein, K. R et al. *Circ Res* 106, 1092-1102, doi:CIRCRESAHA.109.215723 [pii] 10.1161/CIRCRESAHA.109.215723 (2010).
4 Davalos, A. et al. *Mol Cell Proteomics* 9, 2109-2124, doi:M110.001289 [pii] 10.1074/mcp.M110.001289 (2010).
5 Johnstone, S. R. et al. *Am J Pathol* 175, 916-924, doi:S0002-9440(10)60602-5 [pii] 10.2353/ajpath.2009.090160 (2009).
6 Wamhoff, B. R, et al. *Arterioscler Thromb Vasc Biol* 28, 1454-1461, doi:ATVBAHA.107.159392 [pii] 10.1161/ATVBAHA.107.159392 (2008).
7 Billaud, M., et al. *PLoS One* 4, e6432, doi:10.1371/journal.pone.0006432 (2009).
8 Straub, A. C. et al. *Arterioscler Thromb Vasc Biol* 31, 399-407, doi:ATVBAHA.110.215939 [pii] 10.1161/ATVBAHA.110.215939 (2011).
9 Billaud, M. et al. *Microcirculation* 19, 360-372, doi:10.1111/j.1549-8719.2012.00172.x (2012).
10 Wang, X. et al. *Proc Nati Acad Sci USA* 101, 11477-11482, doi:10.1073/pnas.0402201101 0402201101 [pii] (2004).

11 Mollan, T. L., et al. *J Biol Chem*, doi:M111.313247 [pii] 10.1074/jbc.M111.313247.

12 Geraci, G., et al. *J Biol Chem* 244, 4664-4667 (1969).

13 Palmer, L. A. et al. *J Clin Invest* 117, 2592-2601, doi:10.1172/JCI29644 (2007).

14 Fang, K., et al. *Biochem Biophys Res Commun* 252, 535-540, doi:S0006-291X(98)99688-7 [pii] 10.1006/bbrc.1998.9688 (1998).

15 Arnold, K., et al. *Bioinformatics* 22, 195-201, doi:bti770 [pii]10.1093/bioinformatics/bti770 (2006).

16 Guex, N. & Peitsch, M. C. *Electrophoresis* 18, 2714-2723, doi:10.1002/elps.1150181505 (1997).

17 Katchalski-Katzir, E. et al. *Proc Natl Acad Sci USA* 89, 2195-2199 (1992).

18 Tovchigrechko, A. & Vakser, I. A. *Nucleic Acids Res* 34, W310-314, doi:34/suppl_2/W310 [pii] 10.1093/nar/gkl206 (2006).

19 Tovchigrechko, A. & Vakser, I. A. *Proteins* 60, 296-301, doi:10.1002/prot.20573 (2005).

20 Strittmatter, P., et al. *J Biol Chem* 265, 21709-21713 (1990).

Example 2

Introduction

Peripheral vascular resistance, a component of blood pressure regulation, is governed by arterial blood vessel tone. The regulation of vascular tone involves a complex set of cell-cell signaling mechanisms between endothelium and vascular smooth muscle, and it is documented that molecules released from the endothelium (e.g. nitric oxide (NO), endothelium derived hyperpolarizing factor, prostaglandins) influence this process[1-6]. For example, signals originating from vascular smooth muscle stimulate the release of endothelium-derived NO to modulate the contractile response during α1D-adrenergic-mediated vasoconstriction[7,8]. Thus, a balance between contractile and dilatory signaling events is maintained during vasoconstriction.

Recent work has demonstrated that endothelial cell expressed hemoglobin α (Hb α) at the myoendothelial junction (MEJ) is a key regulator of NO diffusion to vascular smooth muscle during vasoconstriction in isolated thoracodorsal arteries[9]. It was discovered that the Hb α heme iron oxidation state, controlled via cytochrome B5 reductase 3, operates as a switch to either permit NO diffusion or NO scavenging 9. From these studies, the role of Hb α at the MEJ both in small arteries and in a vascular cell co-culture (VCCC) was elucidated. Of particular interest, it was observed that Hb α and eNOS form a macromolecular protein complex at the myoendothelial junction and can bind directly to each other shown in small arteries, the VCCC or purified proteins[9]. These data provide a potential mechanism by which Hb α/eNOS protein-protein interaction can regulate NO signaling during vasoconstriction. Thus, it is believed that eNOS/Hb α coupling may play a role in NO signaling and a novel Hb α peptide mimetic was created to investigate this interaction on functional outputs such as vasoconstriction and blood pressure.

Materials and Methods

In Silico Modeling and Peptide Generation:

Modeling interactions of crystal structures between Hb α (PDB number 1Y01) and the oxygenase domain of eNOS (PDB number 3NOS) were performed using a GRAMMX server as previously described[9]. Visualization of molecular interactions and predicted sequence identification was performed using PyMOL software. To accomplish this, interface regions of Hb α with eNOS were identified by selectively removing non-interacting regions, which resulted in the identification of a specific Hb α peptide sequence. The identified sequence was blasted against other mammalian species to determine peptide conservation. Peptides analogous to the first ten amino acids of Hb α (LSFPTTKTYF; SEQ ID NO:2) or a scrambled peptide (FPYFSTKLTT; SEQ ID NO:40) were generated with the addition of an HIV-tat tag (YGRKKRRQRRR; SEQ ID NO:3) to the N-terminus for plasma membrane permeability required in subsequent studies. Peptides were named Hb α X and Scr X respectively. For internalization studies, a fluorescein isothiocyanate (FITC) tagged Hb α X peptide was generated. All peptides were synthesized and purchased from AnaSpec.

Purified eNOS and Hb α Protein Interaction Studies:

Purified Flag-eNOS was purchased from Origene and isolated Hb α chains were generated as previously described[9]. Co-immunoprecipitation studies were performed by incubating 1 μg of Flag-eNOS with 5 μmol/L of each peptide (tat-only, Scr X or Hb α X) for 30 minutes at 37° C. while shaking. Then, 1 μg of isolated Hb α chains were added to the Flag-eNOS/peptide complex for an additional 30 minutes at 37° C. shaking. Anti-Flag nickel beads, blocked with 1% bovine albumin serum for 1 hour, were added to each condition for an additional hour with agitation. Proteins were washed 3x with PBS for 15 minutes and purified protein-protein complexes were precipitated using a strong magnet. The nickel beads were incubated with 5×SDS PAGE buffer to elute proteins off the beads. Samples were subjected to Western blot analysis to determine peptide-induced disruption of Hb α and eNOS binding.

Mice:

Male C57BL/6 mice or eNOS$^{-/-}$ between the ages of 10-12 weeks were purchased from Taconic Farms or Jackson Labs and were used according to the University of Virginia Animal Care and Use Committee guidelines.

Coronary Endothelial Cell Culture and Stimulation:

Primary coronary endothelial cells (Lonza) were cultured on plastic 6-well dishes as previously described[9]. For studies involving basal NO release, endothelial cells were incubated with 5 μmol/L of Scr X or Hb α X for 20 minutes followed by medium collection and nitrite measurements as described below. For bradykinin studies, coronary endothelial cells were grown to confluence followed by serum starvation overnight in a cocktail of Lonza EGM-2 medium supplemented with EGM-2 bullet kit and Opti MEM reduced growth medium using a ratio of 1:9 respectively. The next day, endothelial cells were incubated with Scr X or Hb α X peptide for 20 minutes followed by the addition of 10 μM bradykinin (Sigma) for 5 minutes followed by medium collection for nitrite measurements as described below.

Visualization of HbX-FITC Peptide and Hbα in the Holes of the Internal Elastic Lamina:

Thoracodorsal arteries were isolated from C57BL/6 mice and immediately placed in Krebs-HEPES buffer. Each artery was cannulated in the chamber of a pressure myograph (Danish Myo Technology) filled with Krebs-HEPES and the lumen was perfused and pressurized at 80 mmHg with Krebs-HEPES containing 1% BSA. After a 30 minute equilibration period, the lumen was perfused with the HbX peptide-FITC (5 μmol/L) for 20 minutes. The lumen was then washed with calcium-free Krebs-HEPES and fixed with PFA 4% for 30 minutes. After washing with Krebs-HEPES, the lumen was perfused for 30 minutes with blocking solution (5% goat serum, 0.5% BSA, and 0.25% Triton X in PBS) while the pressure myograph chamber was filled with the same blocking solution. The primary antibody (rabbit anti-Hbα, Abcam, 1/100 in blocking solution) was perfused through the lumen for 10 minutes and the TD arteries were removed from the cannula and placed in an individual well of a 96 well-plate filled with blocking solution and the primary antibody and incubated overnight at 4° C. Next the TD arteries were cannulated again to wash out excess primary antibody. After the washes, Rhodamine Red-conjugated goat anti-rabbit (Jackson ImmunoResearch, 1/50 in blocking solution) was perfused luminally and abluminally. The TD artery was placed in a well of a 96 well-plate containing the secondary antibody in blocking solution for 30 minutes at room temperature. The TD arteries were cannulated again in the pressure myograph to wash out excess secondary antibody luminally and abluminally with calcium-free Krebs-HEPES. Lastly, the lumen was perfused with AlexaFluor633-conjugated sodium hydrazide (Molecular Probes, 0.2 µM in calcium-free Krebs-HEPES) to mark elastin for 20 minutes and the excess dye was further washed for 10 minutes. This technique was based upon previously published methods for protein visualization within the holes of the IEL[10,11]. At the end of the experiment, the TD artery was removed from the cannula at one end while the other end was still secured and the vessel still pressurized. The TD artery was then cut longitudinally from the unattached end and placed on a glass slide with the luminal side facing down and the excess saline solution removed. A single drop of DAPI mounting medium (ProLong Gold, Invitrogen) was placed next to the vessel and a coverslip was positioned on the vessel. The mounting medium was allowed to diffuse between the slide and the coverslip for 10 minutes while a weight was placed on the coverslip to ensure flattening of the artery for microscopy. The coverslip was sealed with nail polish and viewed on an Olympus FV1000 confocal microscope. For quantification purposes, the peptide and Hb α were each determined to be present in the holes of the IEL if fluorescence was >50% maximal intensity, and only within or on the physical boundaries of the hole as determined by the AlexaFluor633 sodium hydrazide.

Proximity Ligation Assay and Quantitation on Thoracodorsal Arteries:

Isolated thoracodorsal arteries were perfused with Scr X or Hb α X peptide (5 µmol/L) for 20 minutes and immediately immersed in 4% paraformaldehyde, paraffin-embedded and sectioned as previously described[12]. Next, sections were de-paraffinized, blocked and incubated with 1:500 mouse anti-eNOS (BD Biosciences), 1:500 rabbit anti-Hb α and 1:500 mouse anti-caveolin-1 (BD Biosciences) primary antibodies overnight at 4° C. The following day, secondary antibodies conjugated with oligonucleotide PLA probes were added, ligated and rolling circle amplification with fluorescent oligonucleotides identified positive interaction sites as previously described[9]. All images were visualized and captured using an Olympus Fluoview 1000 confocal microscope. For proximity ligation assay quantitation, positive interactions indicated by red punctates on the endothelium were counted and divided by the circumference of the lumen using Metamorph software.

Western Blot Analysis of Coronary Endothelial Cell Lysates:

Endothelial cells were harvested in lysis buffer, sonicated and subjected to electrophoresis using 10% Bis-Tris gels (Invitrogen) as previously described[13]. Proteins were transferred to nitrocellulose, incubated with phospho-eNOS 51177 (BD Biosciences) or total eNOS (Sigma) and visualized and quantitated using Li-Cor Odyssey Imager as previously described[14].

Nitrite Measurements from Media of Coronary Endothelial Cells:

Quantitation of nitrite in culture medium was measured by chemiluminescence using a Sievers nitric oxide analyzer according to manufacturer's instructions. Quantitation of peaks was analyzed using Origin Pro 6.0 as previously described[9].

cGMP Assay on Thoracodorsal Arteries:

Isolated thoracodorsal arteries were cannulated and pressurized to 80 mmHg as previously described[13]. Arteries were perfused with 5 µM Scr X or Hb α X with addition of 0.5 mmol/L of the phosphodiesterase inhibitor 3-isobutyl-1-methylxanthine (IBMX) (all conditions) or 100 µmol/L the nitric oxide synthase inhibitor L-NG-Nitroarginine Methyl Ester (L-NAME) for 20 minutes. Arteries were then stimulated with 50 µM phenylephrine for 10 minutes and immediately immersed in lysis buffer provided in the cGMP XP assay Kit (Cell Signaling) according to manufactures instructions. Briefly, a competition enzyme-linked immunoassay was used to generate a standard curve of known cGMP concentrations followed by calculating cGMP concentrations of experimental samples. The cGMP concentration in experimental samples was normalized to total protein concentration.

Pressure Myography on Thoracodorsal Arteries:

Thoracodorsal arteries were isolated, cannulated and pressurized in a Danish Myo Technology (DMT) pressure myograph as previously described[13]. Following 10 minutes of equilibration, vessels were perfused luminally with Scr X or Hb α X peptide and incubated for an additional 20 minutes. Contractile responses were studied using cumulative concentrations ($10^{-9}$-$10^{-3}$ mol/L) of phenylephrine in the presence or absence of 100 µmol/L of L-NAME. After completion of dose response to phenylephrine, potassium chloride (40 mmol/L) was added to ensure vessels could contract equally. Following constriction, the maximum diameter was measured by incubating the vessel in a Krebs calcium free, ethylene glycol tetraacetic acid (EGTA, 1 mmol/L) and sodium nitroprusside (10 µmol/L) solution. Quantitation of vessel diameter was performed using DMT vessel acquisition software and data are expressed as the percentage of initial diameter. Half maximal effective concentration ($EC_{50}$) and maximum drug concentration ($E_{max}$) were calculated at previously described[15].

Abdominal Aorta Ring Assay:

Abdominal aortas were isolated, cut into 2 mm wide rings and mounted on a DMT myograph system with low bath volumes as previously described[16]. Briefly, rings were stretched at 1.2× resting length in Krebs solution and allowed to equilibrate for 30 min at 37° C. prior to depolarization with 154 mm $K^+$ [i]. Following the high $K^+$ contraction, rings were returned to Krebs solution and incubated with 5 µmol/L Scr X or Hb α X peptide for 20 minutes. Cumulative concentrations of phenylephrine (PE) ($10^{-10}$-$10^{-4}$ mol/L) were added to the rings and the magnitude of the tension response measured in milli-newtons.

Blood Pressure Analysis:

Blood pressure was measured in conscious wildtype or eNOS$^{-/-}$ mice under unrestrained conditions using implanted radio telemetry units. Continuous blood pressure measurements were recorded using Dataquest A.R.T. 20 software (DSI). To do so, mice were anesthetized with isoflurane and the catheters (TA11PA-C10, Data Sciences International (DSI)) were implanted in the left carotid artery. The catheter was tunneled through to the radiotransmitter, which was placed in a subcutaneous pouch along the flank. Mice were allowed to recover for seven days after surgery to regain normal circadian rhythms before arterial pressure measurements and experiments were initiated. Thirty minutes prior to peptide injection, continuous blood pressure readings were recorded. Then, a bolus injection of Scr X or Hb α X peptide, or saline was administered via an intraperitoneal injection at 0.125 mg/kg. One hour post-injection, blood pressure was recorded for a 30 minute duration. The change in blood pressure was calculated by subtracting the average pre injection blood pressure from the average post-injection blood pressure.

Statistics:

Statistics on individual comparisons were performed using Student's t-test. For multiple comparisons a one-way ANOVA was used and for dose response curves a two-way ANOVA followed by a Bonferroni's post-hoc test was used. All statistics were computed using GraphPad Prism 5.

Results

Hb α X Peptide Disrupts the Interaction Between eNOS and Hb α.

Figure 23:
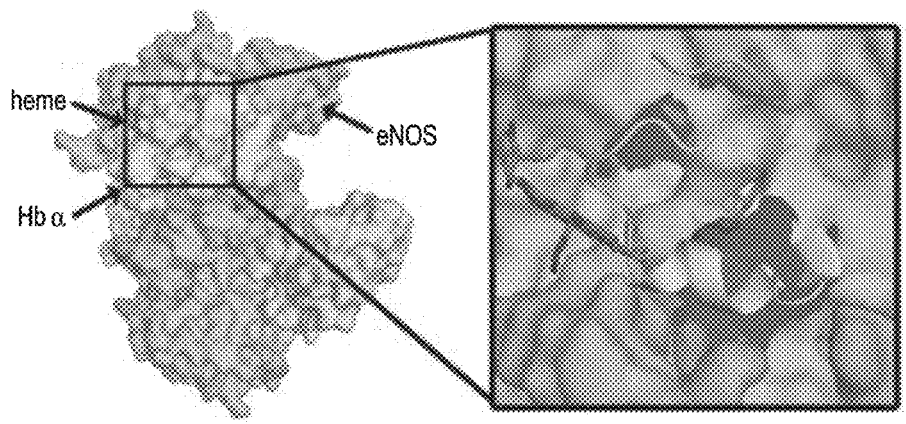
FIG. 23—In silico modeling of human eNOS and Hb α crystal structures and identification of a conserved interaction sequence on Hb α. In silico modeling of the PDB crystal structures for eNOS (gray; 3NOS) and Hb α (orange; 1Y01) using GRAMMX server. The magnified image on right shows the interacting region of Hb α (ribbon structure) that interacts with eNOS (dark gray region). The identified Hb α sequence is below and was blasted against other mammalian species showing conserved sequences highlighted in yellow.

Previous work demonstrated that eNOS and Hb α form a macromolecular complex and can directly interact[9]. Therefore, in silico modeling of the known crystal structures for the oxygenase domain of eNOS and Hb α was used to determine potential interactions based on geometric, electrostatic and hydrophobic indices. From this analysis, a discreet Hb α sequence (LSFPTTKTYFPHFDLSHGSA; SEQ ID NO:1) was found that interacted with eNOS (FIG. 23). Sequences were subjected to homology analysis among several mammalian species revealing a conserved peptide fragment (FIG. 23). Therefore, a peptide (LSFPTTKTYF; SEQ ID NO:2) linked to an HIV tat sequence along with a scrambled control (FPYFSTKLTT; SEQ ID NO:40) were synthesized. The peptides were named Hb α X and Scr X respectively.

Figure 24A:
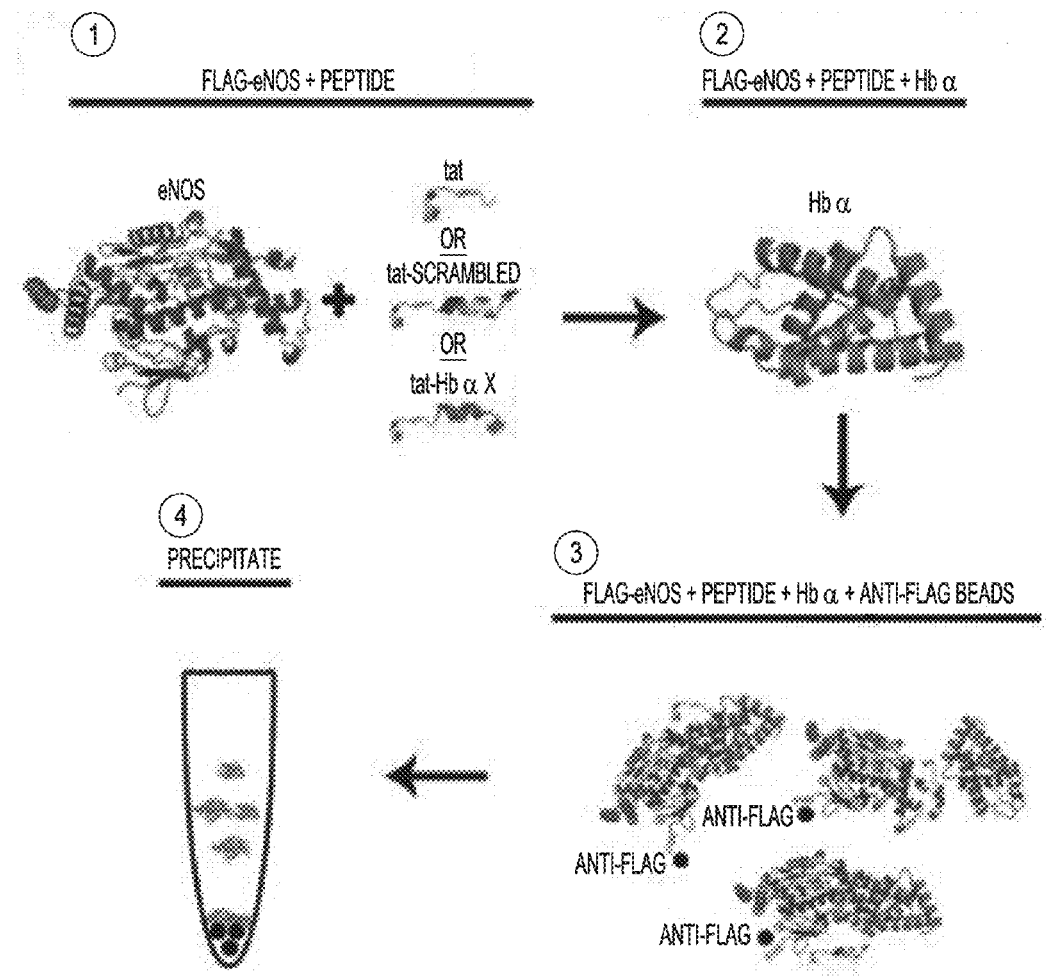
FIG. 24—Hb α X peptide disrupts the interaction between eNOS and Hb α. 24A Schematic of experimental set up testing Hb α X specificity using purified proteins: 1) Flag-eNOS was incubated with tat, Scr X, or Hb α X, 2) Flag-eNOS+peptide complexes were incubated with purified Hb α chains, 3) anti-Flag beads were mixed with Flag-eNOS+peptides, and 4) complexes were precipitated. 24B1 and 24B2, Western blot analysis of Flag-eNOS input, Hb α input and Hb α precipitated with Flag-eNOS (n=3).
Figure 25A:
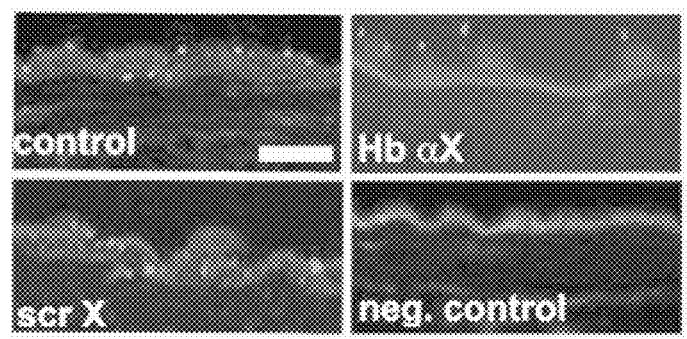
FIG. 25—Hb α X peptide disrupts the eNOS and Hb α complex in thoracodorsal arteries. 25A Proximity ligation assay for eNOS and Hb α (red punctuates) on transverse sections of a mouse thoracodorsal artery. Green shows internal elastic lamina autofluorescence. 25B, The graph on right shows quantitation of red punctates from the proximity ligation assay (n=3). 25C, En face immunofluorescence of Alexa hydrazide 633 (magenta), FITC labeled Hb α X (green) and Hb α (red) on mouse thoracodorsal arteries. Graphs (25D1 and 25D2) show quantitation of colocalized FITC labeled Hb α X and Hb α in IEL holes. Scale bar is 10 µm in 25A and 25C. L indicates lumen and IEL is internal elastic lamina. In 25B * indicates significance between conditions and all error bars represent s.e.m.
Figure 25B:
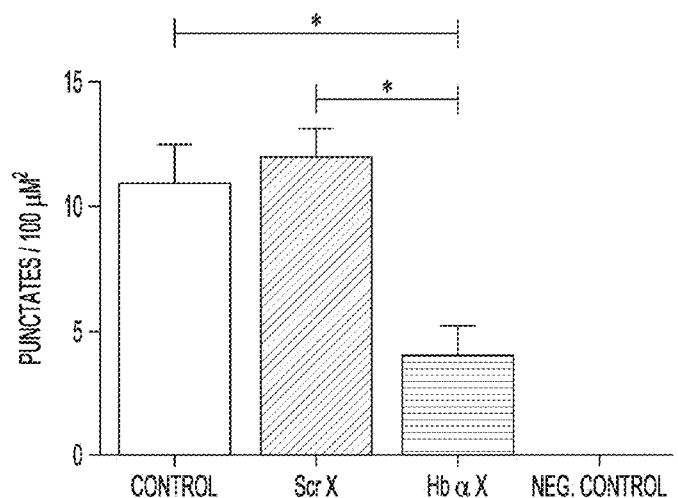
Figure 25C:
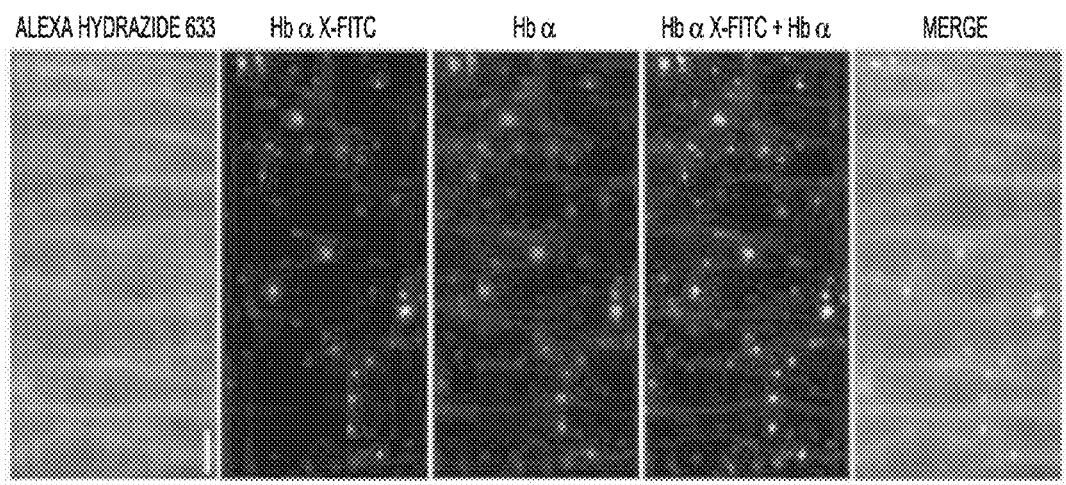

To determine if these peptides competitively inhibited eNOS and Hb α binding, Flag-eNOS was incubated with tat only, Scr X or Hb α X, followed by the addition of purified Hb α chains (FIG. 24a). Complexes were precipitated and subjected to Western blot analysis, demonstrating that only Hb α X peptide significantly disrupted the eNOS/Hb α interaction (FIG. 24b). To test this ex vivo, thoracodorsal arteries were incubated with peptides and measured colocalization of eNOS and Hb α on transverse sections using a proximity ligation assay (FIG. 25a). These studies demonstrate decreased colocalization and a significant loss of protein-protein interaction between eNOS and Hb α (FIG. 25b). Next, FITC-tagged Hb α X peptide was perfused into thoracodorsal arteries followed by fixation and immunolabeling for Hb α (FIG. 25c), which resulted in marked colocalized FITC-tagged Hb α X peptide and Hb α in holes where MEJs are found (FIG. 25d).

Hb α X Peptide Alters NO Signaling in the Vessel Wall.

Following α1$_D$ adrenergic-mediated stimulation, it is known that NO binds to its receptor soluble guanylyl cyclase, resulting in increased cGMP[7-9,17]. To determine the effects of Hb α X peptide on cGMP accumulation during vasoconstriction, thoracodorsal arteries were incubated with Scr X or Hb α X peptides and stimulated with the alp adrenergic agonist phenylephrine. A significant increase in cGMP accumulation with Hb α X compared to the Scr X peptide was observed, which was reversed with the nitric oxide synthase inhibitor, L-NAME (FIG. 26a). Previous work demonstrated that a monolayer of endothelial cells, in the absence of contact with smooth muscle cells, express very little Hb α[9]. Therefore, it was tested whether Scr X or Hb α X altered basal eNOS phosphorylation on serine 1177 (FIG. 27a) or the accumulation of the NO metabolite, nitrite (FIG. 27b) in the culture medium of human microvascular coronary endothelial cells. In these experiments, there were no differences in nitrite or eNOS phosphorylation. In addition, there was no change in nitrite accumulation between Scr X and Hb α X treatments following stimulation of human microvascular coronary endothelial cells with bradykinin (FIG. 27c). The sum of these results indicates that the Hb α X peptide applied ex vivo alters cGMP levels presumably by loss of interaction between Hb α and eNOS resulting in increase NO; however, the Hb α X peptide when applied to endothelial cells lacking protein expression of Hb α does not alter key components of eNOS metabolism.

Figure 26B:
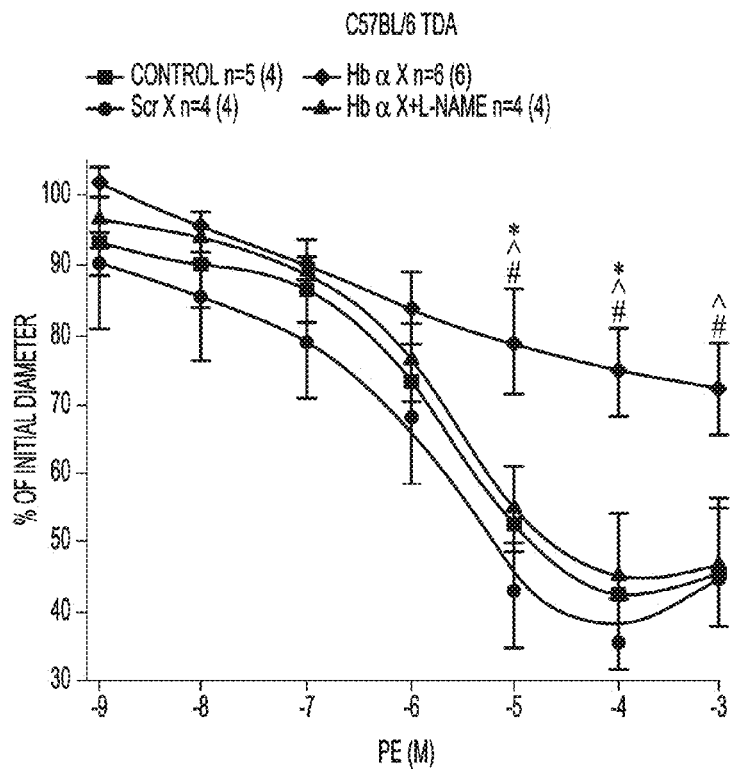
FIG. 26—Hb α X peptide increases nitric oxide signaling in the vessel wall of wildtype but not eNOS$^{-/-}$ mice. a, Measurement of cGMP accumulation following phenylephrine stimulation in thoracodorsal arteries pretreated with Scr X or Hb α X peptide in the presence of L-NAME (n=3). b, Dose response to phenylephrine on arteries treated with Scr X or Hb α X in the presence or absence of L-NAME. c, Cumulative dose response curve on thoracodorsal arteries from eNOS' animals with Scr X or Hb α X. In b and c, n indicates the number of arteries; value in parenthesis shows number of mice. In b and c, * shows significance between Scr X vs. Hb α X, ˆ indicates significance between Hb α X vs. Hb α X+L-NAME analyzed using 1-way ANOVA. All error bars represent s.e.m.
Figure 26C:
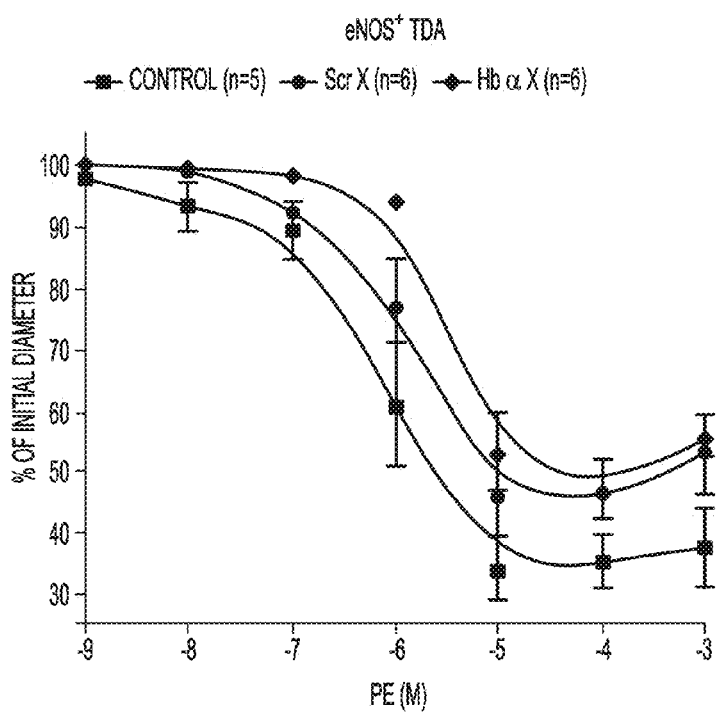
Figure 28:
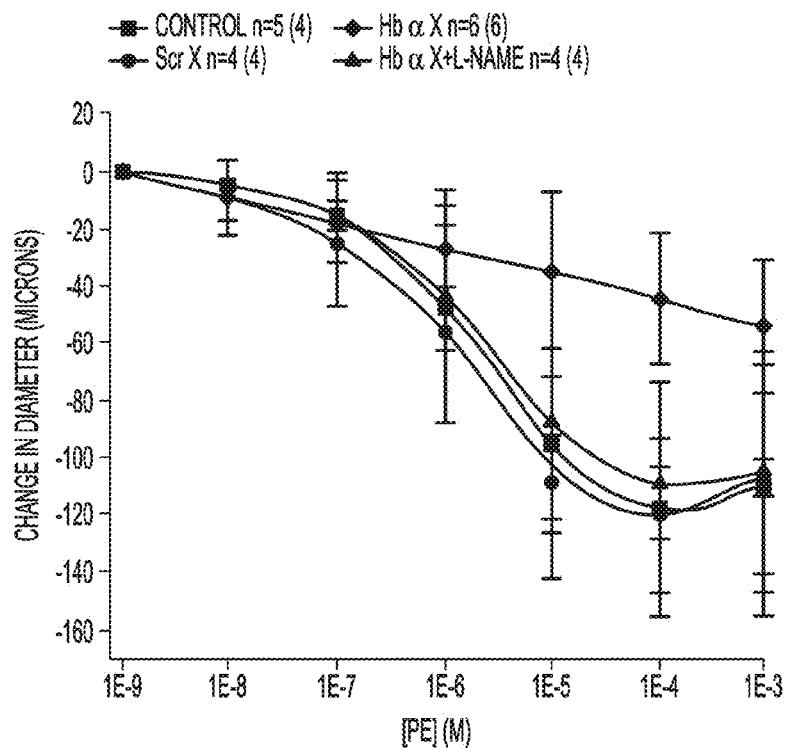
FIG. 28—Dose response to phenylephrine presented as a change in microns on arteries treated with Scr X or Hb α X in the presence or absence of L-NAME. n indicates the number of arteries; value in parenthesis shows number of mice. All error bars represent s.e.m.
Figure 29:
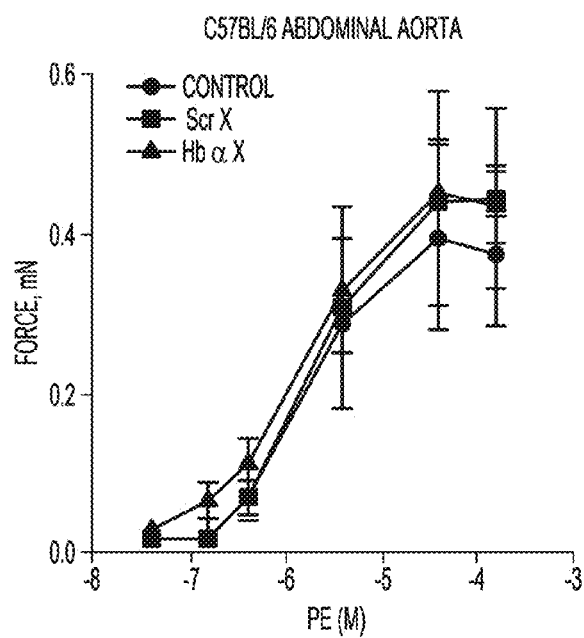
FIG. 29—Effects of Hb α X peptide on wildtype abdominal aortas. Cumulative dose response curve to PE from murine C57BL/6 abdominal aortic rings treated with control, Scr X or Hb α X. All error bars represent s.e.m.

Next, vasoreactivity was performed to determine the effect of the peptide in response to phenylephrine. In thoracodorsal arteries, phenylephrine dose response curves with the Hb α X peptide revealed a significant decrease in constriction compared to untreated arteries, which was reversed with L-NAME (FIG. 26b). Differences are also presented as change in inner diameter measured in micrometers (FIG. 28a). The Scr X peptide showed no difference from control. Both the $EC_{50}$ and $E_{max}$ are shown in Table 7 and demonstrate a significant difference only in the presence of Hb α X. The peptides did not alter basal tone of the arteries (FIG. 28b). Previous work has demonstrated that conduit arteries (e.g. aorta, carotid) exhibit no Hb α expression[9,18]. Therefore, the effect of Hb α peptide on abdominal aortic arteries was investigated, which showed no significant change in phenylephrine dose response curves compared to untreated aortas or aortas treated with Scr X (FIG. 29). Lastly, because it has been shown above that the Hb α X peptide disrupts Hb α/eNOS interaction, it was proposed that eNOS$^{-/-}$ mice should not have an altered phenotype when Hba X is applied. Indeed, when eNOS$^{-/-}$ mice were treated with Hb α X, there was no alteration of the magnitude of phenylephrine induced constriction (FIG. 26c). Together, these results demonstrate that the Hb α X peptide induces significant changes in contractility due to increased NO production that is confined to the small arteries expressing Hb α, but not in mice lacking eNOS or conduit arteries where Hb α is absent.

TABLE 7

$E_{max}$ and $EC_{50}$ comparisons for vascular reactivity dose response curves. $E_{max}$ is expressed as % initial diameter and $EC_{50}$ is the [PE] producing half of the maximum effect, expressed in µmol/L.

|  | Control | Hb α X | Scr X | Hbα X + L-NAME |
| --- | --- | --- | --- | --- |
| $E_{max}$ | 44.0 ± 7.6 | 68.0 ± 5.3 | 38.3 ± 2.4 | 45.9 ± 3.0 |
| $EC_{50}$ | 2.1 ± 0.8 | 6.8 ± 0.7 | 2.0 ± 1.3 | 1.9 ± 0.2 |

Hb α X Peptide Alters Systemic Blood Pressure.

The results above indicated the Hb α X peptide had a confined and significant effect on small artery NO release, but not conduit arteries. This provided initial evidence that the peptide could possibly also alter blood pressure regulation through a change in the peripheral resistance. Therefore, radio transmitters were implanted into C57Bl/6 mice to elucidate the effect of Scr X or Hb α X peptide on systemic blood pressure changes. Administration of a single bolus of peptide (0.125 mg/kg) into C57BL/6 mice induced a significant decrease in systolic, diastolic and mean arterial blood pressure in mice injected with the Hb α X peptide, but not mice injected with saline or Scr X peptide (FIG. 30a). The over or under expression of eNOS protein significantly contributes to systemic blood pressure regulation[19-21] and because of this it was tested whether Hba X could alter blood pressure in eNOS$^{-/-}$ mice. Similar to the results with vasoreactivity, there were no alterations in blood pressure in eNOS$^{-/-}$ mice injected with saline or either of the peptides (FIG. 30b). Together, these results provide in vivo evidence that the Hb α X peptide can alter blood pressure homeostasis.

Discussion

Fluctuations in peripheral vascular resistance affecting blood pressure require regulation of blood vessel diameter through highly orchestrated cell signaling cascades and cell-cell communication events between endothelial and smooth muscle cells[3, 4, 22-24]. The known mechanisms regulating resistance arterial tone involve a multifaceted palate of inputs including vasodilators such as endothelial derived hyperpolarizing factor, prostaglandins and nitric oxide[1, 2, 6]. The recent discovery of endothelial cell expressed Hb α as a key regulator of NO diffusion to smooth muscle provides insight into how small arteries regulate NO signaling during vasoconstriction[9]. The work presented herein reveals several novel findings: (i) identification of a conserved sequence where eNOS and Hb α interface, (ii) development of a novel mimetic peptide inhibitor for disruption of eNOS/Hb α protein-protein binding, (iii) identification of a novel mechanism by which coupling of eNOS/Hb α is used for NO scavenging and vascular reactivity, and (iv) the first line of evidence suggesting that the eNOS/Hb α interaction is used for blood pressure regulation. The aggregate of these results offers new mechanistic insight by which Hb α regulates NO signaling in the vessel wall.

Based on previous work[9], it was hypothesized that the strong association and complex formation between Hb α and eNOS may be needed for the functional role of Hb α as a NO scavenger. The first step to test this hypothesis was to perform an in-depth protein-protein interaction analysis using in silico modeling of the known crystal structures for Hb α and eNOS. One limitation to this analysis is that eNOS, comprised of both an oxygenase and reductase domain, only has the oxygenase domain crystallized thereby constraining the modeling to this region. Despite this restriction, a highly conserved Hb α sequence across multiple mammalian species was identified, which prompted the development of mimetic peptides to this motif for competitive inhibitor studies.

Studies using purified Hb α and eNOS protein as well as ex vivo studies with the peptide show greater that 90% inhibition of binding and association with the Hb X peptide, confirming the in silico modeling. Although this data does not identify where Hb α interacts with eNOS, it does provide direct evidence of a specific sequence of Hb α for binding to eNOS.

Functionally, it was shown that Hb α X disrupts NO-dependent signaling as shown in cGMP and vasoreactivity studies. This work provides the first line of evidence demonstrating the importance of the protein-protein interaction between Hb α and eNOS, possibly similar to the mechanism by which caveolin-1 regulates eNOS[30-32]. The possibility of non-specific effects of Hb α X was ruled out assessed by basal phosphorylation of eNOS S1177, NO release measured by nitrite accumulation in basal and stimulated conditions, the lack of effect in abdominal aortas (where Hb cc is not expressed) and in eNOS$^{-/-}$ animals. Even though the functional effects of the peptide are apparent, it is still unclear at this point how the Hb α/eNOS complex assembles. The complex may be pre-constructed and assembled similar to that of NADPH oxidase subunits[33]. Based on previous work[30] and this study, it is tempting to speculate that caveolin-1 maintains eNOS inactive until stimulation, where eNOS then dissociates and recruits met-Hb α and possibly cytochrome B5 reductase 3 to form a macromolecular complex allowing tight NO regulation.

Studies demonstrating an effect of the Hb α X peptide on blood pressure places the purified protein studies and in vitro and ex vivo experiments into a physiological context where NO signaling is significant.

Lastly, this discovery of a conserved Hb α sequence and the development of a novel Hb α mimetic inhibitor provide initial steps for understanding the basic physiological mechanisms that arterial blood vessels use to regulate NO signaling. This work may provides a platform for strategic development of small molecule inhibitors to treat hypertension and possibly other related cardiovascular diseases.

BIBLIOGRAPHY

1. Furchgott R F, Zawadzki J V. *Nature*. 1980; 288:373-376
2. Bunting S, et al. *Prostaglandins*. 1976; 12:897-913
3. Segal S S, Duling B R. *Science*. 1986; 234:868-870
4. Heberlein K R, et al. *Microcirculation*. 2009; 16:307-322
5. Emerson G G, Segal S S. *Circulation research*. 2000; 87:474-479
6. Edwards G, et al. *Nature*. 1998; 396:269-272
7. Dora K A, et al. *Proceedings of the National Academy of Sciences of the United States of America*. 1997; 94:6529-6534
8. Straub A C, et al. *Arterioscler Thromb Vasc Biol*. 2011; 31:399-407
9. Straub A C, et al. *Nature*. 2012; 491:473-477
10. Bagher P, et al. *Proceedings of the National Academy of Sciences of the United States of America*. 2012; 109: 18174-18179
11. Sandow S L, et al. *Circ Res*. 2005; 97:44-51
13. Billaud M, et al. *The American journal of pathology*. 2009; 175:916-924
15. Billaud M, et al. *Microcirculation*. 2012; 19:360-372
16. Somlyo A V, et al. *The Journal of biological chemistry*. 1992; 267:22316-22322
17. Dora K A, et al. *British journal of pharmacology*. 2000; 129:381-387
18. Burgoyne J R, et al. *Hypertension*. 2012; 60:1301-1308
19. Shesely E G, et al. *Proceedings of the National Academy of Sciences of the United States of America*. 1996; 93:13176-13181
20. Van Vliet B N, et al. *J Physiol*. 2003; 549:313-325
21. Ohashi Y, et al. *The Journal of clinical investigation*. 1998; 102:2061-2071
22. Budel S, Bartlett I S, Segal S S. Homocellular conduction along endothelium and smooth muscle of arterioles in hamster cheek pouch: Unmasking an no wave. *Circ Res*. 2003; 93:61-68
23. Segal S S. *Microcirculation*. 2005; 12:33-45
24. Sandow S L, et al. *Microcirculation*. 2012; 19:403-415
25. Kavanaugh J S, et al. *Biochemistry*. 1993; 32:2509-2513
26. Dahmane-Arbane M, et al. *Nouv Rev Fr Hematol*. 1987; 29:317-320
27. Miyashita H, et al. *Hemoglobin*. 1992; 16:1-10
28. Ohba Y, et al. *Hemoglobin*. 1989; 13:637-647
29. Ohba Y, et al. *Biochim Biophys Acta*. 1975; 405:155-160
30. Garcia-Cardena G, et al. *The Journal of biological chemistry*. 1997; 272:25437-25440
31. Michel J B, et al. *The Journal of biological chemistry*. 1997; 272:15583-15586
32. Ju H, et al. *The Journal of biological chemistry*. 1997; 272:18522-18525

33. Lassegue B, et al. *Circulation research.* 2012; 110:1364-1390
34. Schelshorn D W, et al. *Journal of cerebral blood flow and metabolism: official journal of the International Society of Cerebral Blood Flow and Metabolism.* 2009; 29:585-595
35. Nishi H, et al. *J Am Soc Nephrol.* 2008; 19:1500-1508

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

What is claimed is:

1. A peptide consisting of amino acid sequence LSFPTTKTYFPHFDLSHGSA (SEQ ID NO:1) or a peptide consisting of amino acid sequence LSFPTTKTYF (SEQ ID NO:2), said peptide further comprising a plasma membrane permeability sequence.

2. The peptide of claim 1, wherein the plasma membrane permeability sequence comprises an HIV-tat tag sequence of YGRKKRRQRRR (SEQ ID NO:3).

3. A pharmaceutical composition comprising a peptide consisting of amino acid sequence LSFPTTKTYFPHFDLSHGSA (SEQ ID NO:1) or a peptide consisting of amino acid sequence LSFPTTKTYF (SEQ ID NO:2), and a physiologically acceptable carrier, wherein said amino acid sequence further comprises a plasma membrane permeability sequence.

4. The pharmaceutical composition of claim 3, wherein the plasma membrane permeability sequence comprises an HIV-tat tag sequence of YGRKKRRQRRR (SEQ ID NO:3).

\* \* \* \* \*

SEQUENCE LISTING

```
<160> NUMBER OF SEQ ID NOS: 40

<210> SEQ ID NO 1
<211> LENGTH: 20
<212> TYPE: PRT
<213> ORGANISM: Artificial Sequence
<220> FEATURE:
<223> OTHER INFORMATION: A synthetic peptide

<400> SEQUENCE: 1

Leu Ser Phe Pro Thr Thr Lys Thr Tyr Phe Pro His Phe Asp Leu Ser
1               5                   10                  15

His Gly Ser Ala
            20

<210> SEQ ID NO 2
<211> LENGTH: 10
<212> TYPE: PRT
<213> ORGANISM: Artificial Sequence
<220> FEATURE:
<223> OTHER INFORMATION: A synthetic peptide

<400> SEQUENCE: 2

Leu Ser Phe Pro Thr Thr Lys Thr Tyr Phe
1               5                   10

<210> SEQ ID NO 3
<211> LENGTH: 11
<212> TYPE: PRT
<213> ORGANISM: Artificial Sequence
<220> FEATURE:
<223> OTHER INFORMATION: A synthetic peptide

<400> SEQUENCE: 3

Tyr Gly Arg Lys Lys Arg Arg Gln Arg Arg
1               5                   10

<210> SEQ ID NO 4
<211> LENGTH: 20
<212> TYPE: PRT
<213> ORGANISM: Artificial Sequence
<220> FEATURE:
<223> OTHER INFORMATION: A synthetic peptide

<400> SEQUENCE: 4

Leu Ser Phe Pro Thr Thr Lys Thr Tyr Phe Pro His Phe Asp Leu Ser
1               5                   10                  15

His Gly Ser Ala
            20

<210> SEQ ID NO 5
<211> LENGTH: 20
<212> TYPE: PRT
<213> ORGANISM: Bos taurus
```

```
<400> SEQUENCE: 5

Leu Ser Phe Pro Thr Thr Lys Thr Tyr Phe Pro His Phe Asp Leu Ser
1               5                   10                  15

His Gly Ser Ala
            20

<210> SEQ ID NO 6
<211> LENGTH: 20
<212> TYPE: PRT
<213> ORGANISM: Equus caballus

<400> SEQUENCE: 6

Leu Gly Phe Pro Thr Thr Lys Thr Tyr Phe Pro His Phe Asp Leu Ser
1               5                   10                  15

His Gly Ser Ala
            20

<210> SEQ ID NO 7
<211> LENGTH: 20
<212> TYPE: PRT
<213> ORGANISM: Homo sapiens

<400> SEQUENCE: 7

Leu Ser Phe Pro Thr Thr Lys Thr Tyr Phe Pro His Phe Asp Leu Ser
1               5                   10                  15

His Gly Ser Ala
            20

<210> SEQ ID NO 8
<211> LENGTH: 20
<212> TYPE: PRT
<213> ORGANISM: Mus musculus

<400> SEQUENCE: 8

Ala Ser Phe Pro Thr Thr Lys Thr Tyr Phe Pro His Phe Asp Val Ser
1               5                   10                  15

His Gly Ser Ala
            20

<210> SEQ ID NO 9
<211> LENGTH: 20
<212> TYPE: PRT
<213> ORGANISM: Rattus norvegicus

<400> SEQUENCE: 9

Ala Ala Phe Pro Thr Thr Lys Thr Tyr Phe Ser His Ile Asp Val Ser
1               5                   10                  15

Pro Gly Ser Ala
            20

<210> SEQ ID NO 10
<211> LENGTH: 19
<212> TYPE: DNA
<213> ORGANISM: Artificial Sequence
<220> FEATURE:
<223> OTHER INFORMATION: A synthetic primer

<400> SEQUENCE: 10
tggacccggt caacttcaa                                              19

<210> SEQ ID NO 11
<211> LENGTH: 22
```

```
<212> TYPE: DNA
<213> ORGANISM: Artificial Sequence
<220> FEATURE:
<223> OTHER INFORMATION: A synthetic primer

<400> SEQUENCE: 11
gaggctccag cttaacggta tt                                        22

<210> SEQ ID NO 12
<211> LENGTH: 20
<212> TYPE: DNA
<213> ORGANISM: Artificial Sequence
<220> FEATURE:
<223> OTHER INFORMATION: A synthetic primer

<400> SEQUENCE: 12
tgctctctgg ggaagacaaa                                           20

<210> SEQ ID NO 13
<211> LENGTH: 20
<212> TYPE: DNA
<213> ORGANISM: Artificial Sequence
<220> FEATURE:
<223> OTHER INFORMATION: A synthetic primer

<400> SEQUENCE: 13
gagccgtggc ttacatcaaa                                           20

<210> SEQ ID NO 14
<211> LENGTH: 20
<212> TYPE: DNA
<213> ORGANISM: Artificial Sequence
<220> FEATURE:
<223> OTHER INFORMATION: A synthetic primer

<400> SEQUENCE: 14
tcggccaagc agtacttcag                                           20

<210> SEQ ID NO 15
<211> LENGTH: 20
<212> TYPE: DNA
<213> ORGANISM: Artificial Sequence
<220> FEATURE:
<223> OTHER INFORMATION: A synthetic primer

<400> SEQUENCE: 15
acctccagaa tgaccccaga                                           20

<210> SEQ ID NO 16
<211> LENGTH: 20
<212> TYPE: DNA
<213> ORGANISM: Artificial Sequence
<220> FEATURE:
<223> OTHER INFORMATION: A synthetic primer

<400> SEQUENCE: 16
tcctggacca catcaggaag                                           20

<210> SEQ ID NO 17
<211> LENGTH: 20
<212> TYPE: DNA
<213> ORGANISM: Artificial Sequence
<220> FEATURE:
<223> OTHER INFORMATION: A synthetic primer

<400> SEQUENCE: 17
```

-continued tcacccactg tcgagaagga                                          20

<210> SEQ ID NO 18
<211> LENGTH: 20
<212> TYPE: DNA
<213> ORGANISM: Artificial Sequence
<220> FEATURE:
<223> OTHER INFORMATION: A synthetic primer

<400> SEQUENCE: 18
tcctggacca catcaggaag                                          20

<210> SEQ ID NO 19
<211> LENGTH: 20
<212> TYPE: DNA
<213> ORGANISM: Artificial Sequence
<220> FEATURE:
<223> OTHER INFORMATION: A synthetic primer

<400> SEQUENCE: 19
caggcacttc tccagcatgt                                          20

<210> SEQ ID NO 20
<211> LENGTH: 20
<212> TYPE: DNA
<213> ORGANISM: Artificial Sequence
<220> FEATURE:
<223> OTHER INFORMATION: A synthetic primer

<400> SEQUENCE: 20
ggctctttaa gggtcaccca                                          20

<210> SEQ ID NO 21
<211> LENGTH: 20
<212> TYPE: DNA
<213> ORGANISM: Artificial Sequence
<220> FEATURE:
<223> OTHER INFORMATION: A synthetic primer

<400> SEQUENCE: 21
ggggcttaat ctctgcctca                                          20

<210> SEQ ID NO 22
<211> LENGTH: 19
<212> TYPE: DNA
<213> ORGANISM: Artificial Sequence
<220> FEATURE:
<223> OTHER INFORMATION: A synthetic primer

<400> SEQUENCE: 22
ctgaatgtct gggggaggt                                           19

<210> SEQ ID NO 23
<211> LENGTH: 20
<212> TYPE: DNA
<213> ORGANISM: Artificial Sequence
<220> FEATURE:
<223> OTHER INFORMATION: A synthetic primer

<400> SEQUENCE: 23
ttgggctaga ggctggatct                                          20

<210> SEQ ID NO 24
<211> LENGTH: 21
<212> TYPE: RNA
<213> ORGANISM: Artificial Sequence

```
<220> FEATURE:
<223> OTHER INFORMATION: A synthetic primer
<221> NAME/KEY: misc_feature
<222> LOCATION: 20, 21
<223> OTHER INFORMATION: n = t

<400> SEQUENCE: 24
gcaugccucu cuggacaaan n                                              21

<210> SEQ ID NO 25
<211> LENGTH: 21
<212> TYPE: RNA
<213> ORGANISM: Artificial Sequence
<220> FEATURE:
<223> OTHER INFORMATION: A synthetic primer

<400> SEQUENCE: 25
uuuguccaga gagccaugca c                                              21

<210> SEQ ID NO 26
<211> LENGTH: 20
<212> TYPE: RNA
<213> ORGANISM: Artificial Sequence
<220> FEATURE:
<223> OTHER INFORMATION: A synthetic primer
<221> NAME/KEY: misc_feature
<222> LOCATION: 19, 20
<223> OTHER INFORMATION: n =t

<400> SEQUENCE: 26
gaccuacuuc ccucauuunn                                                20

<210> SEQ ID NO 27
<211> LENGTH: 21
<212> TYPE: RNA
<213> ORGANISM: Artificial Sequence
<220> FEATURE:
<223> OTHER INFORMATION: A synthetic primer
<221> NAME/KEY: misc_feature
<222> LOCATION: 20, 21
<223> OTHER INFORMATION: n = t

<400> SEQUENCE: 27
aaagugaggg aaguaggucn n                                              21

<210> SEQ ID NO 28
<211> LENGTH: 21
<212> TYPE: RNA
<213> ORGANISM: Artificial Sequence
<220> FEATURE:
<223> OTHER INFORMATION: A synthetic primer
<221> NAME/KEY: misc_feature
<222> LOCATION: 20, 21
<223> OTHER INFORMATION: n =- t

<400> SEQUENCE: 28
caaauaccgu uaagcuggan n                                              21

<210> SEQ ID NO 29
<211> LENGTH: 21
<212> TYPE: RNA
<213> ORGANISM: Artificial Sequence
<220> FEATURE:
<223> OTHER INFORMATION: A synthetic primer

<400> SEQUENCE: 29
uccagcuuaa cgguauuugg a                                              21
```

<210> SEQ ID NO 30
<211> LENGTH: 21
<212> TYPE: RNA
<213> ORGANISM: Artificial Sequence
<220> FEATURE:
<223> OTHER INFORMATION: A synthetic primer
<221> NAME/KEY: misc_feature
<222> LOCATION: 20, 21
<223> OTHER INFORMATION: n = t

<400> SEQUENCE: 30
acuucaagcu ccuaagccan n                                              21

<210> SEQ ID NO 31
<211> LENGTH: 21
<212> TYPE: RNA
<213> ORGANISM: Artificial Sequence
<220> FEATURE:
<223> OTHER INFORMATION: A synthetic primer
<221> NAME/KEY: misc_feature
<222> LOCATION: 20
<223> OTHER INFORMATION: n = t

<400> SEQUENCE: 31
uggcuuagga gcuugaagun g                                              21

<210> SEQ ID NO 32
<211> LENGTH: 21
<212> TYPE: RNA
<213> ORGANISM: Artificial Sequence
<220> FEATURE:
<223> OTHER INFORMATION: A synthetic primer
<221> NAME/KEY: misc_feature
<222> LOCATION: 20, 21
<223> OTHER INFORMATION: n = t

<400> SEQUENCE: 32
agggcuucgu gaaugaggan n                                              21

<210> SEQ ID NO 33
<211> LENGTH: 21
<212> TYPE: RNA
<213> ORGANISM: Artificial Sequence
<220> FEATURE:
<223> OTHER INFORMATION: A synthetic primer

<400> SEQUENCE: 33
uccucauuca cgaagcccug g                                              21

<210> SEQ ID NO 34
<211> LENGTH: 21
<212> TYPE: RNA
<213> ORGANISM: Artificial Sequence
<220> FEATURE:
<223> OTHER INFORMATION: A synthetic primer
<221> NAME/KEY: misc_feature
<222> LOCATION: 20, 21
<223> OTHER INFORMATION: n = t

<400> SEQUENCE: 34
ggacacccau cccaaguuun n                                              21

<210> SEQ ID NO 35
<211> LENGTH: 21
<212> TYPE: RNA
<213> ORGANISM: Artificial Sequence
<220> FEATURE:
<223> OTHER INFORMATION: A synthetic primer

```
<221> NAME/KEY: misc_feature
<222> LOCATION: 20, 21
<223> OTHER INFORMATION: n = t

<400> SEQUENCE: 35
aaacuuggga uggguguccn n                                              21

<210> SEQ ID NO 36
<211> LENGTH: 21
<212> TYPE: RNA
<213> ORGANISM: Artificial Sequence
<220> FEATURE:
<223> OTHER INFORMATION: A synthetic primer
<221> NAME/KEY: misc_feature
<222> LOCATION: 20, 21
<223> OTHER INFORMATION: n = t

<400> SEQUENCE: 36
ggaggaacuc aggaacaaan n                                              21

<210> SEQ ID NO 37
<211> LENGTH: 21
<212> TYPE: RNA
<213> ORGANISM: Artificial Sequence
<220> FEATURE:
<223> OTHER INFORMATION: A synthetic primer

<400> SEQUENCE: 37
uuuguuccug aguuccucca g                                              21

<210> SEQ ID NO 38
<211> LENGTH: 20
<212> TYPE: RNA
<213> ORGANISM: Artificial Sequence
<220> FEATURE:
<223> OTHER INFORMATION: A synthetic primer
<221> NAME/KEY: misc_feature
<222> LOCATION: 19, 20
<223> OTHER INFORMATION: n = t

<400> SEQUENCE: 38
gacaaaaagu ccaaccuann                                                20

<210> SEQ ID NO 39
<211> LENGTH: 21
<212> TYPE: RNA
<213> ORGANISM: Artificial Sequence
<220> FEATURE:
<223> OTHER INFORMATION: A synthetic primer

<400> SEQUENCE: 39
uaggguugga cuuuuuguca g                                              21

<210> SEQ ID NO 40
<211> LENGTH: 10
<212> TYPE: PRT
<213> ORGANISM: Artificial Sequence
<220> FEATURE:
<223> OTHER INFORMATION: A synthetic peptide

<400> SEQUENCE: 40

Phe Pro Tyr Phe Ser Thr Lys Leu Thr Thr
  1               5                  10
```